(12) United States Patent
Harvey et al.

(10) Patent No.: US 8,383,399 B2
(45) Date of Patent: Feb. 26, 2013

(54) NUCLEIC ACID CONSTRUCT HAVING AN OVALBUMIN PROMOTOR

(75) Inventors: Alex J. Harvey, Athens, GA (US); Jeffrey C. Rapp, Athens, GA (US)

(73) Assignee: Synageva BioPharma Corp., Lexington, MA (US)

( * ) Notice: Subject to any disclaimer, the term of this patent is extended or adjusted under 35 U.S.C. 154(b) by 0 days.

(21) Appl. No.: 13/179,281

(22) Filed: Jul. 8, 2011

(65) Prior Publication Data

US 2012/0083033 A1 Apr. 5, 2012

Related U.S. Application Data

(60) Division of application No. 11/978,360, filed on Oct. 29, 2007, now abandoned, and a continuation-in-part of application No. 11/699,257, filed on Jan. 26, 2007, now Pat. No. 7,541,512, and a continuation-in-part of application No. 11/799,253, filed on May 1, 2007, now abandoned, which is a continuation-in-part of application No. 11/210,165, filed on Aug. 23, 2005, now abandoned.

(60) Provisional application No. 60/930,491, filed on May 16, 2007, provisional application No. 60/994,203, filed on Sep. 18, 2007, provisional application No. 60/640,203, filed on Dec. 29, 2004.

(51) Int. Cl.
*C12N 15/00* (2006.01)
*C12N 5/00* (2006.01)
*C12N 5/02* (2006.01)

(52) U.S. Cl. .................................. 435/320.1

(58) Field of Classification Search ............... 435/320.1, 435/325
See application file for complete search history.

(56) References Cited

U.S. PATENT DOCUMENTS

| | | | |
|---|---|---|---|
| 4,496,537 A | 1/1985 | Kwan et al. | |
| 4,959,317 A | 9/1990 | Sauer et al. | |
| 4,997,763 A | 3/1991 | Hughes et al. | |
| 5,162,215 A | 11/1992 | Bosselman et al. | |
| 5,304,489 A | 4/1994 | Rosen et al. | |
| 5,364,783 A | 11/1994 | Ruley et al. | |
| 5,367,054 A | 11/1994 | Lee et al. | |
| 5,378,618 A | 1/1995 | Sternberg et al. | |
| 5,464,764 A | 11/1995 | Capecchi et al. | |
| 5,487,992 A | 1/1996 | Capecchi et al. | |
| 5,595,886 A * | 1/1997 | Chapman et al. | 435/69.6 |
| 5,677,177 A | 10/1997 | Wahl et al. | |
| 5,714,353 A | 2/1998 | Pathak et al. | |
| 5,741,957 A | 4/1998 | Deboer et al. | |
| 5,784,992 A | 7/1998 | Petitte et al. | |
| 6,069,133 A | 5/2000 | Chiou et al. | |
| 6,825,396 B2 | 11/2004 | MacArthur et al. | |
| 7,335,761 B2 | 2/2008 | Harvey et al. | |
| 7,511,120 B2 | 3/2009 | Ivarie et al. | |
| 7,524,626 B2 | 4/2009 | Harvey et al. | |
| 7,541,512 B2 | 6/2009 | Rapp et al. | |
| 7,585,963 B2 | 9/2009 | Leavitt et al. | |
| 2006/0015960 A1 | 1/2006 | Ivarie et al. | |

FOREIGN PATENT DOCUMENTS

| | | |
|---|---|---|
| EP | 1548114 A1 | 6/2005 |
| JP | 2006262875 A | 10/2006 |
| WO | WO00/17376 A1 | 9/1999 |
| WO | WO00/11151 | 3/2000 |
| WO | WO03/022040 A2 | 3/2003 |
| WO | WO03/081993 A2 | 10/2003 |
| WO | WO2006/212045 A2 | 11/2006 |
| WO | WO2008/020960 A1 | 2/2008 |

OTHER PUBLICATIONS

Yu, PNAS, 1986, vol. 83, p. 3194-3198.*
Stover (Molecular Therapy, Apr. 2001, vol. 3, No. 4, p. 543-550).*
Ilves (Gene, Jun. 1, 1996, vol. 171, No. 2, p. 203-208).*
Flamant (Gen. Virol., Jan. 1993, vol. 74, part 1, p. 39-46).*
Zufferey (J. Virol., 1998, vol. 72, No. 12, p. 9873-9880).*
Ginn (Human Gene Therapy, Aug. 10, 2003, vol. 14, No. 12, p. 1127-1137).*
Nakajima (FEBS letters, Jan. 4, 1993, vol. 315, No. 2, p. 129-133).*
Bosselman et al., Replication-Defective Vectors of Reticuloendotheliosis Virus Transduce Exogenous Genes into Somatic Stem Cells of the Unincubated Chicken Embryo, Journal of Virology, 2680-2689 (1989).
Catterall et al., The chick ovomucoid gene contains at least six intervening sequences, Nature 278:323-327 (Mar. 1979).
Cosset et al., "Improvement of avian leucosis virus (ALV)-based retrovirus vectors by using different cisacting sequences from ALVs," Journal of Virology, 65:3388-3394 (1991).
Cosset et al., "Use of helper cells with two host ranges to generate high-titer retroviral vectors," Virology 193:385-395 (1993).
Dierich et al., Cell-specificity of the chicken ovalbumin and conalbumin promoters, EMBO Journal, vol. 6 No. 8, pp. 2305-2312 (1987).
Etches et al., "Contributions to somatic and germline lineages of chicken blastodermal cells maintained in culture," Molecular Reproduction and Development, 45:291-298 (1996).
Flamant et al., Importance of 3' non-coding sequences for efficient retrovirus-mediated gene transfer in avian cells revealed by self-inactivating vectors, Journal of Virology, 74:39-46 (1993).
Gannon et al., "Organization and sequences at the 5' end of a cloned complete ovalbumin gene," Nature, 276:428-434 (1979).
Gibbins et al., Gene Constructs for Testing Transgenic Poultry, The Thirty-Seventh Annual National Breeders' Roundtable (1988).
Gordon et al., Production of Human Tissue Plasminogen Activator in Transgenic Mouse Milk, Biotechnology, 5:1183-1187 (1987).
Harvey et al., Expression of exogenous protein in the egg white of transgenic chickens, Nature Biotechnology, 19:396-99 (2002).

(Continued)

*Primary Examiner* — Michael C. Wilson
(74) *Attorney, Agent, or Firm* — Hak J. Chang; Eugene J. Kim

(57) ABSTRACT

A transgenic avian containing in its genome an exogenous nucleotide sequence which includes a promoter component and a vector with reduced promoter interference wherein the exogenous nucleotide sequence is integrated into the genome and the avian.

7 Claims, 14 Drawing Sheets

OTHER PUBLICATIONS

Jung et al., Exons encode functional and structural units of chicken lysozyme, PNAS USA,77:5759-5763 (1980).
Kato et al., "A far upstream estrogen response element of the ovalbumin gene contains several half-palindromic 5'- TGACC-3' motifs acting synergistically," Cell, 68:731-742 (1992).
Kaye et al., "A close association between sites of Dnase I hypersensitivity and sites of enhanced cleavage by micrococcal nuclease in the 5'-flanking region of the actively transcribed ovalbumin gene," The EMBO Journal, 3:1127-1144 (1984).
Lai et al., "The ovalbumin gene: structural sequences in native chicken DNA are not contiguous," Proc. Natl. Acad. Sci. USA, 75:2205-2209 (1978).
Love et al., "Transgenic birds by DNA microinjection," Bio/Technology, 12:60-63 (1994).
Park et al., "Modulation of transcriptional activity of the chicken ovalbumin gene promoter in primary cultures of chicken oviduct cells: effects of putative regulatory elements in the 5'-flanking region," Biochemistry and Molecular Biology International, 36:811-816 (1995).
Roop et al., "Definition of the 5' and 3' ends of transcripts of the ovalbumin gene," Cell, 19:63-68 (1980).
Royal et al., "The ovalbumin gene region: common features in the organization of three genes expressed in chicken oviduct under hormonal control," Nature, 279:324-331 (1997).
Sanders et al., "Positive and negative regulatory elements control the steroid-responsive ovalbumin promoter," Biochemistry, 27:6550-6557 (1988).
Sambrook et al., "Molecular Cloning: A Laboratory Manual", 2nd ed., Cold Spring Harbor (1989).
Scott et al., "Generation of tissue-specific transgenic birds with lentiviral vectors", PNAS USA, vol. 102, No. 5, pp. 16443-16447 (2005).
Scott et al., Ovoinhibitor Introns Specify Functional Domains as in the Related and Linked Ovomucoid Gene, Journal of Biol. Chemistry, 262:5899-5907(1987).
Scott et al., Deoxyribonuclease I Sensitivity of the Ovomucoid-Ovoinhibitor Gene Complex in Oviduct Nuclei and Relative Location of CR1 Repetitive Sequences, Biochemistry 26:6831-6840 (1987).
Shuman et al., Production of transgenic birds, Experientia 47, 897-905 (1991).
Thoraval et al., "Germline transmission of exogenous genes in chickens using helper-free ecotropic avian leucosis virus-based vectors," Transgenic Research, 4:369-376 (1995).
Vick et al., "Transgenic birds from transformed primordial germ cells," Proc. R. Soc. Lond. B., 179-183 (1993).
Wilmut et al., Methods of Gene Transfer and Their Potential Use to Modify Milk Composition, Theriogenology, 33:113-123 (1990).
Yee et al., "Generation of high-titer pseudotyped retroviral vectors with very broad host range," Methods in Cell Biology, 43:99-112 (1994).
Zhu et al., Production of human monoclonal antibody in eggs of chimeric chickens, Nature Biotechnology, 23:(9) 1159-69 (2005).
Bosselman et al., Germline Transmission of Exogenous Genes in the Chicken, Science, vol. 243, p. 533-535, (1989).
Chen et al., Production and Design of More Effective Avian Replication-Incompetent Retroviral Vectors, Developmental Biology 214: 370-384 (1999).
Watanabe et al., Encapsulation sequences for spleen necrosis virus, an avian retrovirus, are between the 5' long terminal repeat and the start of the gag gene, Proc. Natl. Acad. Sci USA, 79:5986-5990 (1982).
Office Action, U.S. Appl. No. 11/978,360 dated Jun. 26, 2009.
Office Action, U.S. Appl. No. 11/978,360 dated Jan. 22, 2010.
Office Action, U.S. Appl. No. 11/978,360 dated Jun. 22, 2010.
Office Action, U.S. Appl. No. 11/978,360 dated Feb. 11, 2011.
International Search Report and Search Report, PCT/US2007/022828, Mail date: Apr. 28, 2009.

* cited by examiner

```
ctgcagccca ggcagcacac tagagcagag aaatctagtt agcagcaacc actggcagac      60
agaaatgatt atatagatta catactgacc ctagcctctt acactgccta ctgcatcact     120
gaaaggactg ggaagaagag agtgcaataa cgaagctgaa gctaggagga aggcaaggag     180
aactgaagct gactagggaa aaggggatt aaaggtttaa gtgtctattc catagtttgc      240
tggtttgttt tttgtcaatt cctgaatcag taatttttat gttaattagc aaaaaattac     300
aaacactccc caagtcagga ctgttaccta caacagaagc tcagatcagc tgagccttag     360
tcttttggtc cctccctagg gaatgctgta tgtgtctctc tctccaggcc tgctcaaaat     420
tgacctcaga cccaaacttt tgctgaatct ccagtaccac ctcttttgct cctaactaga     480
taacaaagcc ctgagcgctt tgcttttagc aaagctttaa gtgccattac caactgcacc     540
tggagccttt acctacccct atggacccag gctctatatt taagctctgc cctgaacctt     600
cacttctttc ctgtcctaag ttagatgtac tagtatggtg tgtactatgt ctccagttca     660
aacacagctg tgcccatacc tggccaagga ctcctagtat gacctgggct gtgccttgct     720
gctaaggacc tgctgggtga ttgctggacc tgatcctaat cctgaattaa gaaatgattt     780
cttggcttga ctggatgtgc cctgtggtat gatactgcct tatgatttgg actcttgttt     840
gcagctgtgc aaatccctaa ggagcccagt ctctggccac ctggaatctt gtcactacca     900
aacttcctga gggactggtc ttgctctggg ttctgatctc tggacagtac tcacccttta     960
ctcagcccag gctcccagtt aagccccttt ccaccctgcc aggctctccg ctccatccct    1020
agcaggggct ctcatgacag tgtgaccccc ccttactcag gtcagggcca cttgtgccac    1080
gttcctttcc tgtcttctgt ccctgccttg gctctaaagc agtgtgctac catccacaac    1140
cactgcatct ctctaaagta agcctctcct gagccgcatg ctctgtaacg aggaaggatg    1200
cactttgctc agaaggatgc gaggctgctg ctgagcctg agggcactga cctcccatga    1260
ggtacacccc atacccagga ccacaattca gcctgctgga accatcaact cctgccgag    1320
taaggccata gcaagaccag catccacctc cctgcagccc tgccctgccc agatattggg    1380
cctgctgatc tcaggatgca gacttgcttc tcagcttgac ctaagcattg ccctgtcttt    1440
atggacccac ctggttagca agttcagtgc agaaggaggc tgttggcatc tagctaattt    1500
tccacccaca ttactgtctg ctgactcatt ctacgtctct cccatcttgt tacaataata    1560
atttgggaga tcatattgaa ggtcttaata aagtcaaggc atgtgatatt ctctgctttg    1620
cctttgtttc tagaataagc cacttcatca tagaagatga aaatgctgat cagcagagat    1680
ctgtgcttga taaatccatg ctggcttttc ctatcacctt atattccttc atatgccttg    1740
agacacccaa ggaggccttg gatcagagct gtctgtagca gtcctaactg gtatacaatt    1800
agttgtacaa caggtagtga tccgcataat agttggcgtg agaaagtggg cctgtgctgt    1860
gtcaagcata gagtttgggt tccagtcctg ttctgatgg cacatatgcc tgagcagctg    1920
ggtaatctct gcattccaat tggaaggcag gggcctgtag gcagttccca cttggcatgg    1980
gtgattgtac cacctgtgtc ctcatctgtg aagcatcatg ttttcattca aatatccttt    2040
tgtttgacag tagaaatgaa cagaattgtt ttttttttcct aagcaaattc tgcaagagct    2100
ctgaagaaca aggtgtcagt gaacttctag ctccatagat aggacttgca tcacatgtca    2160
tgccttgatt ggaggtctat ccgatactga acaacttgtg gttccctgag ggaatgtaag    2220
attactgata ctactctctc tttatgttag ctacaataaa tggtaggtta agcaatagat    2280
acagagtttg agtgcctttc ttacaagcat catagtgaac aaatccactg gtgatctacc    2340
ttttcaataa ctacagagaa ttgtaatctc ttggattctc ctccttcccc gttctgaaaa    2400
tgtgttcttt ttttccaaat cagaaacctt cctcaaccac cctgactatt ctttggacat    2460
tgttttgttc ttgctcctaa ataggcttta aatttttgt aagtgaaagg cttttgcatgc    2520
aggtgaggct acaactcatt cagtaacaat gaggaagact gtcagattt ggggaaaatt     2580
ctcccaccca acctttttgct agccagtaag atgtaagcac tgaatgtcat gccacacaga    2640
ccataccaac atcagaccac atatctacag gaagctttaa ggaatcattg actgtacagt    2700
gaagggtaaa tcaaattaaa atgaatgtga ggtctgatac gagatatcct catgggaatc    2760
aagagcaaag acaaatagtt tttcacagtc ttgtcatgat ctgtcacaga ccaaggcagc    2820
acagcaggca acaatgttgg tctcttcaga atggcacagc accgctgcag aaaaatgcca    2880
ggtggactat gaactcacat ccaaggagc ttgacctgat acctgatttt cttcaaacag      2940
gggaaacaac acaatcccac aaaatagctc agagagaaac catcactgat ggctacagca    3000
ccaaggtatg caatggcaat ccattcgaca ttcatctgtg acctgagcaa aatgatttat    3060
ctctccatga atggttgctt ctttccctca tgaaaaggca atttccacac tcacaatatg    3120
caacaaagac aaacagagaa caattaatgt gctccttcct aatgtcaaaa ttgtagtggc    3180
aaagaggaga acaaaatctc aagttctgag taggttttag tgattggata gaggctttg    3240
acctgtgagc tcacctggac ttcatatcct tttggataaa agtgctttt ataactttca    3300
ggtctccgag tctttattca tgagactgtt ggtttaggga cagaccaaca atgaaatgcc    3360
tggcatagga aagggcagca gagcctgagc tgaccttttc ttgggacaag cattgtcaaa    3420
caatgtgtga caaaactatt tgtactgctt tgcacagctg tgctgggcag ggcaatccat    3480
tgccacctat cccaggtaac cttccaactg caagaagatt gttgcttact ctctctagac    3540
ccccagtca aaccaactat gcaggtatgc tgacaacgct atgatgacag cctgttctga    3600
tcaagatctc atttgttcat ggacaatttt tgttgcttgc agctggtctt ccattgggaa    3660
agagtgtagt atatccttct catctgacag aaaagcagaa attctcatgc tccacactta    3720
atctacattg tttttaaacca ccagctactt cttggagagg aaaaatggct tttataagac    3780
tcacaaaaca aagctctgca agtcaaatgc atacaaaact gttctgtagg tctggaatca    3840
```

FIG. 8a

```
ggacactatg tggaagtcaa atagagaagc tttaaaaaaa cctttgggat cattctcatc    3900
ttatatttgc agcacgatac tatgacagtg ataactgaca taactgcatc aatttccttg    3960
atattttatt tgtcttaaag tacaagacat agagatggac gtaaagatgg acatatgact    4020
caggtctgga caggtccgtg gtccatgtat gataaaagag atgaaggaa ggagaatgga     4080
gactgtctaa gaagggcttc agggacgttc tgaaggcaga tttgactgaa tcagatgtac    4140
tgtccaagtc tcatatgtag caatggaaga ctgatattgg agaaatataa agaaatggct    4200
gtgaactcaa agtgaccctg aacagaaaag ggatatggag ttaaaataat ggcacagaac    4260
tgaggtttat atgatatacc atgggctgca gagggtcaga gtgctccacc atgggcctct    4320
cttgggctgc agggaacttc tgttctacac ctggaacacc tcctgccctc ctccgcactg    4380
acctcagtgt catcagggct gtttctctca catttttctca ctcacctctc ccaactacca   4440
ttgtacagca gttgttctta catcttgctc ctcctgaggt gcatctagca tcgatcactg    4500
gctcagctct ggccagtggc agctcccttt tgaggacacg ggacagctgc tgggctctgt    4560
tcacagaggc cactccagca gacctccact accacaactt gtagtgtaaa tccactacaa    4620
ctttctgagc tacagaaatg aaatggagac cctctctgct atgggataca aagaggaaa     4680
cgtggcgttt agtgctctgg ctcactggta cacccaacca cagggtgaga agcagcctgt    4740
tgttattcac tactcttagg acagattatg gtgaattgtt aataaaagca tttcttcata    4800
acatccaaag gaggaaatac actaaattat attttttatt tattaattac acatgcttaa    4860
ttatatatgg catggttgct ttgaaagaac cttgtcctta ctgaccagat ctgctgtttg    4920
ctgagacaaa atggctgaca attttggcca tgtggatac cttccccctt ttctgtagca     4980
ttaggacaga agttattctg gagcctgtct gacaagtcag acttgataac tttaagtatt    5040
tggaagtgtg cttttcatgc tggatgtcat ctccagaacc tccctgtctg gtaagcagtt    5100
ccctgcctta gtaagagccg aaacggtctc tcttttcctt gttatctcac caggatatta    5160
caatgtgaca ggactatctg aactacgcca acctgcaaat tccaaatata tatatatata    5220
tgtaagatat ctatacacaa attattagtg tttgattgac accagatgac agagaagtgc    5280
atctgagaaa acctattccc aatctccttt ctctttctgc agactgacat gcatttcata    5340
ggtagagata acatttactg ggaagcacat ctatcatcat aaaaagcagg caagattttc    5400
agactttctt agtggctgaa ataagagcaa aagcagtgat taaaacaaa atgaaacaaa     5460
aaaaatcagt tgatacctgt ggtgtagaca tccagcaaaa aatattatt tgcactacca     5520
tcttgtctta agtcctcaga cttggcaagg agaatgtaga tttctacagt atatatgttt    5580
tcacaaaagg aaggagagaa acaaaagaaa atggcactga ctaaacttca gctagtggta    5640
taggaaagta attctgctta acagagattg cagtgatctc tatgtatgtc ctgaagaatt    5700
atgttgtact ttttccccc attttttaaat caaacagtgc tttacagagg tcagaatggt    5760
ttcttactg tttgtcaatt ctattatttc aatacagaac aatagcttct ataactgaaa     5820
tatatttgct attgtatatt atgattgtcc ctcgaaccat gaacactcct ccagctgaat    5880
ttcacaattc ctctgtcatc tgccaggcca ttaagtatt catggaagat ctttgaggaa     5940
cactgcaagt tcatatcata aacacatttg aaattgagta ttgttttgca ttgtatggag    6000
ctatgttttg ctgtatcctc agaaaaaag tttgttataa agcattcaca cccataaaaa     6060
gatagattta aatattccag ctataggaaa gaaagtgcgt ctgctcttca ctctagtctc    6120
agttggctcc ttcacatgca tgcttcttta tttctcctat tttgtcaaga aaataatagg    6180
tcacgtcttg ttctcactta tgtcctgcct agcatggctc agatgcacgt tgtagataca    6240
agaaggatca aatgaaacag acttctggtc tgttactaca accatagtaa taagcacact    6300
aactaataat tgctaattat gttttccatc tctaaggttc ccacattttt ctgtttttctt   6360
aaagatccca ttatctggtt gtaactgaag ctcaatggaa catgacaat atttcccagt     6420
cttctctccc atccaacagt cctgatggat tagcagaaca ggcagaaaac acattgttac    6480
ccagaattaa aaactaatat ttgctctcca ttcaatccaa aatggaccta ttgaaactaa    6540
aatctaaccc aatcccatta aatgattttct atggcgtcaa aggtcaaact tctgaaggga   6600
acctgtgggt gggtcacaat tcaggctata tattccccag ggctcagcca gtgtctgtac    6660
atacagctag aaagctgtat tgcctttagc agtcaagctc gaaagtaag caactctctg     6720
gaattacctt ctctctatat tagctcttac ttgcacctaa actttaaaa attaacaatt     6780
attgtgctat gtgttgtatc tttaagggtg aagtacctgc gtgataccc ctataaaaac     6840
ttctcacctg tgtatgcatt ctgcactatt ttattatgtg taaagctttt gtgtttgttt    6900
tcaggaggct tattctttgt gcttaaaata tgttttaat ttcagaacat cttatcctgt     6960
cgttcactat ctgatatgct ttgcagtttg cttgattaac ttctagccct acagagtgca    7020
cagagagcaa aatcatggtg ttcagtgaat tctggggagt tatttaatg tgaaaattct     7080
ctagaagttt aattcctgca aagtgcagct gctgatcact acacaagata aaaatgtggg    7140
gggtgcataa acgtatattc ttacaataat agatacatgt gaacttatat acagaaaaga   7200
aaatgagaaa aatgtgtgtg tgtatactca cacactgtgt cagtaaaaac ttttgagggg    7260
tttaatacag aaaatccaat cctgaggccc cagcactcag tacgcatata aagggctggg    7320
ctctgaagga cttctgactt tcacagatta tataaatctc aggaaagcaa ctagattcat    7380
gctggctcca aaagctgtgc tttatataag cacactggct atacaatagt tgtacagttc    7440
agctctttat aatagaaaca gacagaacaa gtataaatct tctattggtc tatgtcatga    7500
acaagaattc attcagtggc tctgttttat agtaaacatt gctattttat catgtctgca    7560
tttctcttct gtctgaatgt caccactaaa atttaactcc acagaaagtt tatactacag    7620
tacacatgca tatctttgag caaagcaaac catacctgaa agtgcaatag agcagaatat    7680
```

FIG. 8b

```
gaattacatg cgtgtctttc tcctagacta catgacccca tataaattac attacttatc   7740
tattctgcca tcaccaaaac aaaggtaaaa atactttga agatctactc atagcaagta   7800
gtgtgcaaca aacagatatt tctctacatt tattttagg gaataaaaat aagaaataaa   7860
atagtcagca agcctctgct ttctcatata tctgtccaaa cctaaagttt actgaaattt   7920
gctctttgaa tttccagttt tgcaagccta tcagattgtg tttaatcag aggtactgaa   7980
aagtatcaat gaattctagc tttcactgaa caaaaatatg tagaggcaac tggcttctgg   8040
gacagtttgc tacccaaaag acaactgaat gcaaatacat aaatagattt atgaatatgg   8100
ttttgaacat gcacatgaga ggtggatata gcaacagaca cattaccaca gaattacttt   8160
aaaactactt gttaacattt aattgcctaa aaactgctcg taatttactg ttgtagccta   8220
ccatagagta ccctgcatgg tactatgtac agcattccat ccttacattt tcactgttct   8280
gctgtttgct ctagacaact cagagttcac catgggctcc atcggtgcag caagcatgga   8340
attttgtttt gatgtattca aggagctcaa agtccaccat gccaatgaga acatcttcta   8400
ctgccccatt gccatcatgt cagctctagc catggtatac ctgggtgcaa agacagcac   8460
caggacacaa ataataagg tgagcctaca gttaaagatt aaaacctttg ccctgctcaa   8520
tggagccaca gcacttaatt gtatgataat gtcccttgga aactgcatag ctcagaggct   8580
gaaaatctga aaccagagtt atctaaaagt gtggccacct ccaactccca gagtgttacc   8640
caaatgcact agctagaaat cttgaaactg gattgcataa cttctttttg tcataaccat   8700
tatttcagct actattattt tcaattacag gttgttcgct ttgataaact tccaggattc   8760
ggagacagta ttgaagctca ggtacagaaa taatttcacc tccttctcta tgtcccttc   8820
ctctggaagc aaaatacagc agatgaagca atctcttagc tgttccaagc cctctctgat   8880
gagcagctag tgctctgcat ccagcagttg ggagaacact gttcataaga acagagaaaa   8940
agaaggaagt aacaggggat tcagaacaaa cagaagataa aactcaggac aaaaataccg   9000
tgtgaatgag gaaacttgtg gatatttgta cgcttaagca agacagctag atgattctgg   9060
ataaatgggt ctggttggaa aagaaggaaa gcctggctga tctgctggag ctagattatt   9120
gcagcaggta ggcaggagtt ccctagagaa aagtatgagg gaattacaga agaaaaacag   9180
cacaaaattg taaatattgg aaaaggacca catcagtgta gttactagca gtaagacaga   9240
caggatgaaa aatagttttg taaacagaag tatctaacta ctttactctg ttcatacact   9300
acgtaaaact tactaagtaa taaaactaga ataacaacat cttctttct ctttgtattc   9360
agtgtggcac atctgtaaac gttcactctt cacttagaga catcctcaac caaatcacca   9420
aaccaaatga tgtttattcg ttcagccttg ccagtagact ttatgctgaa gagagatacc   9480
caatcctgcc agtaagttgc tctaaaatct gatctgagtg tattccatgc caaagctcta   9540
ccattctgta atgcaaaaac agtcagagtt ccacatgttt cactaagaaa atttcttttt   9600
ctcttgtttt tacaaatgaa agagaggaca aataacattt ctctatcacc gacctgaaac   9660
tctacagtct tcagagaatg aatggcttgc taaaagaatg tcaaatctta ctatacagct   9720
atttcatatt acactactaa atacactata aggcatagca tgtagtaata cagtgtaaaa   9780
tagcttttta cactactata ttattaatat ctgttaattc cagtcttgca tttcacattt   9840
gcaaaacgtt ttgaaattcg tatctgaaag ctgaatactc ttgctttaca ggaatacttg   9900
cagtgtgtga aggaactgta tagaggaggc ttggaaccta tcaactttca aacagctgca   9960
gatcaagcca gagagctcat caattcctgg gtagaaagtc agacaaatgg taaggtagaa   10020
catgctttgt acatagtgag agttggttca ccctaatact gagaacttgg atatagctca   10080
gccagcgtgc tttgcgttca agcttaccag agctgttgta tgcctgttaa gcagggcata   10140
cagtcatgag gctcttgaaa aatcttaaca gacaaaggc aatggaaaat cggagttaag   10200
ggatggtagg gataaaatgc atagaaagag gtaccacaat tttgattttt gccctaatgc   10260
ctctctgcgt ggttcctcaa ttttttctact tcattcctca tctcctcaga gcattccttt   10320
ccctcatgct tgaaacacag atgaaagact gtgaattcta actgagatga aaacatccac   10380
aaccacacaa cctctggtgt ggagtcacat tctgtgaagg caaaaactag gccacgtaat   10440
ctatgcgtgc aagctacgcg taagctatgt gtgtgacagg acaatgtgag gaacatacta   10500
tgtgcacaag gactgcagaa taaacaggag caaagttttt gaagaaaaca gagtaaaatc   10560
ctgttttcct cttttgttac attctttaca tatatctcaa atttcctctt tggttagaag   10620
caagtaatat ttatgtttct tggtactgtt tgggttgaag accattctgg gataagagaa   10680
attccagtgg ttcttcccct aatcataaaa tgtcaggttt agttttttg taacacagaa   10740
atctcttcat cttttatctt ttgttgtgat tcttgataga gagagaaaca agacttactg   10800
acaatagcag caagaaaatc aatcttggaa gaacaagatt gcaattgcaa aaacaacca   10860
atgtccttgc ccctacatcc tcttccccat aattctacat ttctctatct accttgtgct   10920
tgccaacatg atatacgtaa actctctttt cctattcatt cttaaggaa ttatcagaaa   10980
tgtccttcag ccaagctccg tggattctca aactgcaatg gttctggtta atgccattgt   11040
cttcaaagga ctgtgggaga aagcatttaa ggatgaagac acacaagcaa tgcctttcag   11100
agtgactgag gtatatgggc ataccttaga gatgtaatct agaatttatg aagagagtag   11160
acatgttgtt atatgaacac tgcattagcg tatctgctca tttgtctgca tctctttcag   11220
acactgtgtt aaaagcaggg aattttcctt atgtctctct cgtcacaata ttcctgacat   11280
tgcaaagctc ctgagaaata acttcagatt ccacttttcc taggaaggct tctggatgag   11340
aactaatcat cttaactgta actagacatt tctgcatcca agaataatct ttgttaaaac   11400
tatattctct ctctcttttt tttttttttt tggttctcca gcaagaaagc aaacctgtgc   11460
agatgatgta ccagattggt ttatttagag tggcatcaat ggcttctgag aaaatgaaga   11520
```

FIG. 8c

```
tcctggagct tccatttgcc agtgggacaa tgagcatgtt ggtgctgttg cctgatgaag  11580
tctcaggcct tgagcaggta tggccctaga agttggcttc agaatattaa aaacacatgg  11640
aaatttagct gttgtaaagc tcttttcaac acagttatcc taaaacattt aaccagcaca  11700
aatttcatca tgattcaata tgtgattgtt gcatagaagt gtagatttgt cccactgggt  11760
cctgcaatag cccatgctga gcatggcttg ctgaaagaac tgctttagag ggtgaaaagt  11820
ttgacacagc agacaagatg attctcacct aagcagctgt tactgtagtg gcttgaactc  11880
taaaggtctt gtatctccat tcctgtgcac tgaggagctt cttggaaagt tcatataagg  11940
tttactagtt ctaactatta tctcatttgg tggcactcaa tgtgctttgt tcacgtcttc  12000
ataaattaat ctatctaaaa attggatgtg gttaaagcaa tttcagaaat aacatgtaca  12060
taatgtacaa ttattgatat gaacagaaca caggcatagc atattgtaat taggaggact  12120
gtagttattt tgaataggaa acacaatgta ataaatgaga attcattgaa atgttagtat  12180
gctaactcaa tctaaattat aaagataaag aggcatttaa tcacagctag atttccatca  12240
cttgtgacag acaggcatat gaatgattat gtacagctct aggaaaaaaa gtatgtagga  12300
aaactagtac attttgatta gaaagtctga aatgaggtg ccttgatcaa agagaatacg  12360
tgtgtttgag aaaaaaaaag tttggataga ggtggtaaga gagaatatat tgaaatggtg  12420
tttctacaaa ctgccatggc cagatttgtg taagagacat tcagtaagta ggcaaggaaa  12480
gaaatattac taggtacaaa gcaacatcag taataccaaa agaaaccaat tattccagat  12540
gccaatctcg taataggqtt aagagatttc caccccctcta gtggtcacca gtgcaaccag  12600
taactttgct aatttacatt ttctttttt aaatgcagaa tagactttg aactgagtga  12660
tcatgaactg gtactgtgta atagatgaag acatacttga cgactaaact tctgatttt  12720
aaaaactcaa attctcttga aagatcagtt cccagtctag taacagctga tagtttaagt  12780
atcagtaatt ggctaccatt aacaactggc tcctgagagg tcttaaatgt agagacagct  12840
ttaaactcaa aagcacagag tgattttag aatagatttc ccaagcaaag aaaataaaca  12900
gggaggagct ttaagggagt agccatctca ttattattat tatttaaaga aatggcagca  12960
agcctacaaa agaaaaataa gacagagcag agaagaaaga gtcatggtat gcttttctat  13020
cttagcaaaa ttaatctcta catgcctagg aaaaagccat gacaagagca atcagttcaa  13080
aagtgtatg caaaaaacca cataatagta actagtactg cattgccagg aaggaagtta  13140
tgtcgccatt ccatggatct cattctcatt tcctgctgac ttgagagtat aatcaactct  13200
gaaaaactga ctgaatggac cagttctaat gttatggaag agaggaagat caaagtgtac  13260
ttacctcgca tgaagatgga ggaaaaatac aacctcacat ctgtcttaat ggctatgggc  13320
attactgacg tgtttagctc ttcagccaat ctgtctggca tctcctcagc agagagcctg  13380
aagatatctc aagctgtcca tgcagcacat gcagaaatca atgaagcagg cagagaggtg  13440
gtagggtcag cagaggctgg agtggatgct gcaagcgtct ctgaagaatt tagggctgac  13500
catccattcc tcttctgtat caagcacatc gcaaccaacg ccgttctctt ctttggcaga  13560
tgtgtttccc cttaaaaaga agaaagctga aaaactctgt cccttccaac aagacccaga  13620
gcactgtagt atcaggggta aaatgaaaag tatgttatct gctgcatcca gacttcataa  13680
aagctggagc ttaatctaga aaaaaatca gaaagaaatt acactgtgag aagcaggtgca  13740
attcactttt cctttacaca gagtaatact ggtaactcat ggatgaaggc ttaagggaat  13800
gaaattggac tcacagtact gagtcatcac actgaaaaat gcaacctgat acatcagcag  13860
aaggtttatg ggggaaaaat gcagccttcc aattaagcca gatatctgta tgaccaagct  13920
gctccagaat tagtcactca aaatctctca gattaaatta tcaactgtca ccaaccattc  13980
ctatgctgac aaggcaattg cttgttctct gtgttcctga tactacaagg ctcttcctga  14040
cttcctaaag atgcattata aaaatcttat aattcacatt tctccctaaa ctttgactca  14100
atcatggtat gttggcaaat atggtatatt actattcaaa ttgttttcct tgtacccata  14160
tgtaatgggt cttgtgaatg tgctctttg ttcctttaat cataataaaa acatgtttaa  14220
gcaaacactt ttcacttgta gtatttgaag tacagcaagg ttgtgtagca gggaaagaat  14280
gacatgcaga ggaataagta tggacacaca ggctagcagc gactgtagaa caagtactag  14340
tgggtgagaa gttgaacaag agtcccctac aagcaactta atctaataag ctagtggtct  14400
acatcagcta aaagagcata gtgagggatg aaattggttc tcctttctaa gcatcacctg  14460
ggacaactca tctggagcag tgtgtccaat ctgccgctgc cctgatctcg gctggggtga  14520
tgggacagac cttggctgcc actgagacat ctgagacact gagatctgtc tcaactcaga  14580
tttacccaag aacagctcat tgccaacaga acaaaatctc aaacttatgg ctagtgatga  14640
cagcagtcag ttgtcccatc tgtgacccac caaggctggc atgctggaat gagcaggctt  14700
tggtggcatg tagttactgg acagcaccac tgacatgggc aggggaaaaa ctgagcatgg  14760
tgtaaatcac tgcctcaaag ccacttctct gtgcctgcac catgcttgaa agctcttcta  14820
caggagctgg gtttgttcaa gaaagcttct gtttctccca tctgcttctt gtaccttcac  14880
aggacagagg ttagaaggggt acagccatga ctgagggaaga ctgactttca aatgtgccta  14940
attttccttt ggttgctgct gcagccctgcag aagaagggg tcagaagcca agagctttga  15000
gataaggatg cctaacctat gttgaagaca tttgtgctga cacctcaggc cccaggatag  15060
gacaactgct ggattgtggc taacccacta gctacagaac ctaatttata ttaccagatt  15120
aggaagagca aaagaacatg tatttataac aggaggtctt ctgtgcttct ctactaaaag  15180
gtgctgtgaa ggagcccaca gtgcagcagt tatgaggcc tgaaagaggc cgcagcacac  15240
gaaagagcccct ggtaggagca gcacacagag gggcaggagg gctggggaa ctgccacccca  15300
tgggacctg tgtgaagcag tgcactcctg aggggtggac tgcgtgggaa aggaaaagaa  15360
```

FIG. 8d

```
agcaaacaga cctgtgatga actgtcacac agactgcaga gtgacagagg agggcacgag    15420
gcagtgcgcc cactgcaggg agtggcgctc cttcctcaca gcagcgctaa cagcttggca    15480
ccaatattca gtagtctgtg gtgatacttt ttccagtttc accacacagc atttcgcttg    15540
ttctacttgt tttagctttc cccctccaca agataacaca tactttgcca gtcagtccct    15600
aagaccttaa cttaacagtt agcaaacagg atcttgcaaa agaaggaaga taacatgaca    15660
ccaccttcac tggtgtataa atagttcaaa tactttcctt cactttcccg taaattagtt    15720
gattgcaggt caggagataa caggggaact tactgcaaga gagaaaatga tgtttaatat    15780
tgtcttggac tttctggtgg tctgggcatg aaaatggggt actcaaaatc ctcgggacgt    15840
ttatttttca cctgatttat tcccaaactg cactatttct aggccattgg agttcttatc    15900
aattaaatta tactttggct ctctgctatc tcactccctt tcatcttcag catcactttc    15960
agcacaatta caggagaaga cttagactca gagctttagg actcatcata agaggctttc    16020
attgctctgt caccacaccc catatagatc t                                    16051
```

FIG. 8e

AATTGAGGAGCTTTGTTCCTTGGGTTCTTGGGAGCAGCAGGAAGCACTATGGGCGCAGC
GTCAATGACGCTGACGGTACAGGCCAGACAATTATTGTCTGGTATAGTGCAGCAGCAGA
ACAATTTGCTGAGGGCTATTGAGGCGCAACAGCATCTGTTGCAACTCACAGTCTGGGGC
ATCAAGCAGCTCCAGGCAAGAATCCTGGCTGTGGAAAGATACCTAAAGGATCAACAGCT
CCTGGTAC

FIG. 9a

AATGTGGGGAGGGCAAGGCTTGCGAATCGGGTTGTAACGGGCAAGGCTTGACTGAGGGG
ACAATAGCATGTTTAGGCGAAAAGCGGGGCTTCGGTTGTACGCGGTTAGGAGTCCCCTC
AGGATATAGTAGTTTCGCTTTTGCATAGGGAGGGGGAAAT

FIG. 9b

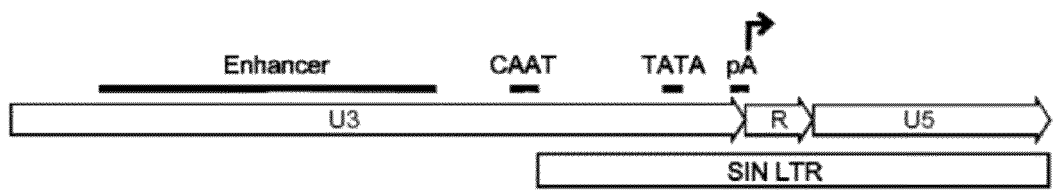

FIG. 10 a

```
AATGTAGTCTTATGCAATACTCTTGTAGTCTTGCAACATGCTTATGTA
ACGATGAGTTAGCAACATGCCTTATAAGGAGAGAAAAAGCACCGT
GCATGCCGATTGGTGGGAGTAAGGTGGTATGATCGTGGTATGATC
GTGCCTTGTTAGGAAGGCAACAGACGGGTCTAACACGGATTGGAC
GAACCACTGAATTCCGCATTGCAGAGATATTGTATTTAAGTGCCTAG
CTCGATACAATAAACGCCATTTGACCATTCACCACATTGGTGTGCA
CCTGGGTTGATGGCCGGACCGTTGATTCCCTGRCGACTACGAGC
ACATGCATGAAGCAGAAGGCTTCATT
```

FIG. 10 b

NUCLEIC ACID CONSTRUCT HAVING AN OVALBUMIN PROMOTOR

RELATED APPLICATION INFORMATION

This application is Divisional of U.S. patent application Ser. No. 11/978,360 filed Oct. 29, 2007, now abandoned which claims the benefit of U.S. provisional application Nos. 60/930,491, filed May 16, 2007 and 60/994,203, filed Sep. 18, 2007 and is a continuation-in-part of U.S. patent application Ser. No. 11/699,257, filed Jan. 26, 2007, now U.S. Pat. No. 7,541,512, issued Jun. 2, 2009, and is also a continuation-in-part of U.S. patent application Ser. No. 11/799,253, filed May 1, 2007, now abandoned, which is a continuation-in-part of U.S. patent application Ser. No. 11/210,165, filed Aug. 23, 2005, now abandoned which claims the benefit of U.S. provisional application No. 60/640,203, filed Dec. 29, 2004. The disclosures of each of these US patent applications and provisional applications are incorporated in their entirety herein by reference.

FIELD OF THE INVENTION

The present invention relates generally to the use of promoters which function in cells of a transgenic avian (e.g., oviduct cells) such as a transgenic chicken and vectors which contain such promoters. More specifically, the invention relates to recombinant nucleic acids and expression vectors, transfected cells and transgenic animals, for example, transgenic avians such as transgenic chickens, that contain vectors with gene expression controlling regions operably linked to coding sequences.

BACKGROUND

The field of transgenics was initially developed to understand the action of a single gene in the context of the whole animal and the phenomena of gene activation, expression and interaction. Transgenics technology has also been used to produce models for various diseases in humans and other animals and is among the most powerful tools available for the study of genetics, and the understanding of genetic mechanisms and function. From an economic perspective, the use of transgenic technology to convert animals into "protein factories" for the production of specific proteins or other substances of pharmaceutical interest (Gordon et al., 1987, Biotechnology 5: 1183-1187; Wilmut et al., 1990, Theriogenology 33: 113-123) offers significant advantages over more conventional methods of protein production by gene expression.

One system useful for expressing foreign proteins is the avian reproductive system. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized, if sperm are present, and then moves into the magnum of the oviduct, which is lined with tubular gland cells. These cells secrete the egg-white proteins, including ovalbumin, lysozyme, ovomucoid, conalbumin and ovomucin, into the lumen of the magnum where they are deposited onto the avian embryo and yolk. In the past exogenous protein production has been performed in the avian reproductive system specifically targeting the avian oviduct.

Advantages of targeting the avian oviduct for exogenous protein expression can include proper folding and post-translation modification of the target protein, the ease of product recovery, and a shorter developmental period of birds such as chickens compared to other animal species.

Directing expression of a heterologous gene product in the oviduct of a transgenic avian can be significantly advantageous over ubiquitous expression in the bird. That is, the consequences of ubiquitous expression of a bioactive gene product in a host animal may be undesirable. For example, in certain instances the ubiquitous presence of the recombinant protein may be harmful to the development of the avian which can kill the bird. Additionally, the bird's health may be negatively effected leading to reduced levels of protein production.

By weight, approximately 60% of an avian egg is composed of albumen which is composed of four major protein components; ovalbumin, ovomucoid, lysozyme and ovotransferrin with ovalbumin and ovomucoid being present in the greatest quantities.

The ovalbumin promoter, ovomucoid promoter and lysozyme promoter have been successfully employed for the production of heterologous (exogenous) protein in the oviduct of transgenic avians in the past. See, for example, U.S. Pat. No. 6,875,588, issued Apr. 5, 2005; U.S. Pat. No. 7,176,300, issued Feb. 13, 2007; U.S. Pat. No. 7,199,279, issued Apr. 3, 2007; and US patent publication No. 2006/0130170, published Jun. 15, 2006 (the disclosures of each of these three issued patents and one published patent application are incorporated in their entirety herein by reference) which discloses the production of exogenous protein in the avian oviduct facilitated by various avian promoters which are primarily or exclusively expressed in the oviduct. Though expression levels in avians using the promoters and fragments of the promoters disclosed in these issued patents and published application have been at useful levels, the yields have typically been well below 0.1 mg/ml of egg white.

What is needed is a system that will provide for high level expression of an exogenous coding sequence in the cells of a transgenic avian, in particular, in the oviduct cells (e.g., tubular gland cells) of a transgenic avian.

SUMMARY OF THE INVENTION

The present invention meets this need and more. After years of exogenous protein production in transgenic avian oviduct tissue with modest yield the inventors of the present invention have discovered that such production levels can be boosted by about 10 fold to about 100 fold and more by employing new compositions and methods as disclosed herein.

In one aspect, the invention is directed to transgenic avians (e.g., chicken, turkey, quail) containing in their genome an exogenous nucleotide sequence which includes a promoter component and a SIN vector. Typically, the promoter component is linked to a coding sequence exogenous to the avian, i.e., the coding sequence is not normally or naturally present in the avian. Typically, the exogenous nucleotide sequence is integrated into the genome of the avian. In one particularly useful embodiment, the promoter component functions or expresses primarily in the oviduct (e.g., tubular gland cells) of an avian. For example, the promoter component may be an oviduct specific promoter. For example, the promoter component may be one of an avian ovomucoid promoter component, an avian ovalbumin promoter component, an avian lysozyme promoter component and an avian ovoinhibitor promoter component (i.e., conalbumin promoter component).

SIN vectors have been shown by the inventors to be particularly useful for increasing the quantity of exogenous protein produced in the avian oviduct. This effect can be further enhanced when the SIN vector is also an SC negative vector (i.e., a vector not containing a selectable marker cassette with a functional promoter).

The invention also includes methods of making the transgenic avians of the invention and methods of producing an exogenous protein using transgenic avians of the invention. In one embodiment, the transgenic avian has a nucleotide sequence in its genome comprising a vector which is at least one of a SIN vector and an SC negative vector. Typically, the nucleotide sequence includes a promoter component linked to an exogenous coding sequence.

In one useful embodiment, the exogenous coding sequence is expressed in avian oviduct cells and is secreted from the oviduct cells. For example, the exogenous coding sequence may be expressed in tubular gland cells. In one embodiment, the exogenous protein is deposited in a hard shell egg laid by the transgenic avian. In one embodiment, the exogenous protein is a human protein. In one embodiment, the exogenous protein is a therapeutic protein, e.g., a cytokine.

In one embodiment, the transgenic avian contains an exogenous nucleotide sequence in its genome which has a SC negative vector and a promoter component linked to an exogenous coding sequence encoding an exogenous protein. In one embodiment, the SC negative vector is also a SIN vector.

In one aspect, avian leukosis virus vector (ALV), a murine leukemia virus (MLV) retroviral vector, moloney murine leukemia Virus (MMLV) and a lentiviral vector can be used in accordance with the invention.

The invention includes chimeric transgenic avians and fully transgenic germline avians which can be obtained from germline chimeras as is understood by a practitioner of skill in the art of poultry breeding.

The invention also includes gene expression controlling regions or promoters having a nucleotide sequence (i.e., DNA sequence) similar or identical to the following sequences numbered 1 to 8. In a particularly useful embodiment of the invention, the fragments are listed top to bottom in the 5' to 3' linear order in which they are present on a single DNA molecule. For example, the 3' end of the 3.5 kb OV fragment of sequence 1 would be covalently linked to the 5' end of the 5' UTR-5' portion and the 3' end of the 5' UTR-5' portion would be covalently linked to the 5' end of 5' UTR-3' portion. However, the invention is not limited to any particular order of the fragments and intervening nucleotide sequences may be present between the fragments.

1. 3.5 kb OV fragment (includes DHS I, II & III)
   5' UTR-5' portion (from Exon L)
   5' UTR-3' portion (from Exon 1);
2. 3.5 kb OV fragment (includes DHS I, II & III)
   5' UTR-5' portion (from Exon L)
   Intron A
   5' UTR-3' portion (from Exon 1)
   3' UTR;
3. 3.5 kb OV fragment (includes DHS I, II & III)
   5' UTR-5' portion (from Exon L)
   Intron A
   5' UTR-3' portion (from Exon 1);
4. 3.5 kb OV fragment (includes DHS I, II & III)
   5' UTR-5' portion (from Exon L)
   5' UTR-3' portion (from Exon 1)
   3' UTR;
5. 3.5 kb OV fragment (includes DHS I, II & III)
   5' UTR-5' portion (from Exon L)
   Intron A
   5' UTR-3' portion (from Exon 1)
   3' UTR/DHS A (bp 13576 to 15163 of SEQ ID NO: 22)
6. 3.5 kb OV fragment (includes DHS I, II & III)
   5' UTR-5' portion (from Exon L)
   5' UTR-3' portion (from Exon 1)
   3' UTR/DHS A (bp 13576 to 15163 of SEQ ID NO: 22)
7. 3.5 kb OV fragment (includes DHS I, II & III)
   5' UTR-5' portion (from Exon L)
   Intron A
   5' UTR-3' portion (from Exon 1)
   partial 3' UTR
   RRE (Rev response element) FIG. 9a
8. ALV CTE (FIG. 9b) inserted 5' of 3.5 kb OV fragment
   3.5 kb OV fragment (includes DHS I, II & III)
   5' UTR-5' portion (from Exon L)
   Intron A
   5' UTR-3' portion (from Exon 1)
   partial 3' UTR;

Coordinates of some of the elements for specific ovalbumin constructs disclosed herein (e.g., constructs 1 to 8 described above) are shown in the 16051 bp ovalbumin DNA segment of SEQ ID NO: 22 as follows:

3.5 kb OV fragment (includes DHS I, II & III): Start: 3199 End: 6659 of FIG. 8 (SEQ ID NO: 22);

1.4 kb OV fragment (includes DHS I & II): Start: 5209 End: 6659 of FIG. 8 (SEQ ID NO: 22);

3.8 kb OV fragment: Start: 2863 End: 6659 of FIG. 8 (SEQ ID NO: 22);

5.2 kb OV fragment: Start: 1463 End: 6659 of FIG. 8 (SEQ ID NO: 22);

5' UTR-5' portion (from Exon L): Start: 6659 End: 6705 of FIG. 8 (SEQ ID NO: 22);

5' UTR-3' portion (from Exon 1): Start: 8295 End: 8311 of FIG. 8 (SEQ ID NO: 22);

3' UTR: Start: 13576 End: 14209 of FIG. 8 (SEQ ID NO: 22);

partial 3' UTR: Start 13576 End: 13996 of FIG. 8 (SEQ ID NO: 22);

Intron A: Start: 6706 End: 8294 of FIG. 8 (SEQ ID NO: 22);

Intron E: Start: 10010 End: 10968 of FIG. 8 (SEQ ID NO: 22);

Exon L: Start: 6659 End: 6705 of FIG. 8 (SEQ ID NO: 22);
Exon 1: Start: 8295 End: 8478 of FIG. 8 (SEQ ID NO: 22);
Exon 2: Start: 8731 End: 8781 of FIG. 8 (SEQ ID NO: 22);
Exon 3: Start: 9363 End: 9491 of FIG. 8 (SEQ ID NO: 22);
Exon 4: Start: 9892 End: 10009 of FIG. 8 (SEQ ID NO: 22);
Exon 5: Start: 10968 End: 11110 of FIG. 8 (SEQ ID NO: 22);
Exon 6: Start: 11442 End: 11597 of FIG. 8 (SEQ ID NO: 22);
Exon 7: Start: 13180 End: 13575 of FIG. 8 (SEQ ID NO: 22);

+1 SITE: Start: 6659 End: 6659 of FIG. 8 (SEQ ID NO: 22);
ATG: Start: 8312 End: 8312 of FIG. 8 (SEQ ID NO: 22);
Poly A: Start: 14204 End: 14209 of FIG. 8 (SEQ ID NO: 22);
TATA: Start: 6627 End: 6632 of FIG. 8 (SEQ ID NO: 22);
DHS A: Start: 13858 End: 15163 of FIG. 8 (SEQ ID NO: 22);
DHS IV: Start: 459 End: 859 of FIG. 8 (SEQ ID NO: 22);
DHS III: Start: 3253 End: 3559 of FIG. 8 (SEQ ID NO: 22);
DHS II: Start: 5629 End: 6009 of FIG. 8 (SEQ ID NO: 22); and
DHS I: Start: 6359 End: 6659 of FIG. 8 (SEQ ID NO: 22).

Promoter constructs are also contemplated that have a nucleotide sequence 80% identical and 85% identical and 90% identical and 91% identical and 92% identical and 93% identical and 94% identical and 95% identical and 96% identical and 97% identical and 98% identical and 99% identical to each of the promoter constructs disclosed herein, such as those described above (i.e., 1 to 8 above).

The invention also contemplates promoter constructs which correspond to promoter constructs 1 through 8 above in which the 3.5 kb OV fragment is replaced with the 3.8 kb OV fragment. The invention also contemplates promoter constructs which correspond to promoter constructs 1 through 8 in which the 3.5 kb OV fragment is replaced with the 5.2 kb OV fragment.

Promoter constructs are also contemplated for each of the above specified recombinant promoters (i.e., 1 to 8) in which DHS III is omitted from the construct.

Promoter constructs are contemplated corresponding to each of constructs 2, 3, 5, 7 and 8 above in which Intron A is replaced with Intron E which may lead to increased levels of exogenous protein production. Intron A and E have DNA sequences that induce alignment of histones in surrounding DNA regions. Such alignment can provide for transcriptional regulation of the OV gene. Without wishing to be bound to any particular theory or mechanism of operation, substitution of Intron E with Intron A may provide a preferential spacing of histones that result from use of Intron E (i.e., the periodicity for Intron A is 202 bp+/−5 bp, for Intron E is 196 bp+/−5 bp). For example, it is believed that the packaging of DNA by histones leads to topological alteration of DNA the manipulation of which can lead to preferential alignment of binding sites for proteins responsible for the transcription regulation (e.g., transcription factors) leading to an enhanced level of transcription.

Also included in the invention are vector constructs, and other constructs and nucleotide sequences disclosed herein, having a nucleotide sequence 80% identical and 85% identical and 90% identical and 91% identical and 92% identical and 93% identical and 94% identical and 95% identical and 96% identical and 97% identical and 98% identical and 99% identical to each vector construct and other constructs and nucleotide sequences disclosed herein.

Any useful combination of features described herein is included within the scope of the present invention provided that the features included in any such combination are not mutually inconsistent as will be apparent from the context, this specification, and the knowledge of one of ordinary skill in the art Additional objects and aspects of the present invention will become more apparent upon review of the detailed description set forth below when taken in conjunction with the accompanying figures, which are briefly described as follows.

BRIEF DESCRIPTION OF THE FIGURES

FIG. 8a-e (SEQ ID NO: 22) shows a segment of a chicken ovalbumin gene.

FIG. 9a (SEQ ID NO: 25) shows the RRE (rev responsive element) sequence of a lenti virus. FIG. 9b (SEQ ID NO: 26) shows the ALV CTE (constitutive transport element) sequence.

FIG. 10a shows a diagram of the segment deleted from an exemplary retroviral LTR (ALV) to make a SIN vector. FIG. 10b (SEQ ID NO: 29) shows the sequence of the LTR shown in 10a. The underlined sequence is the deleted sequence.

DETAILED DESCRIPTION

Definitions

Figure 1:
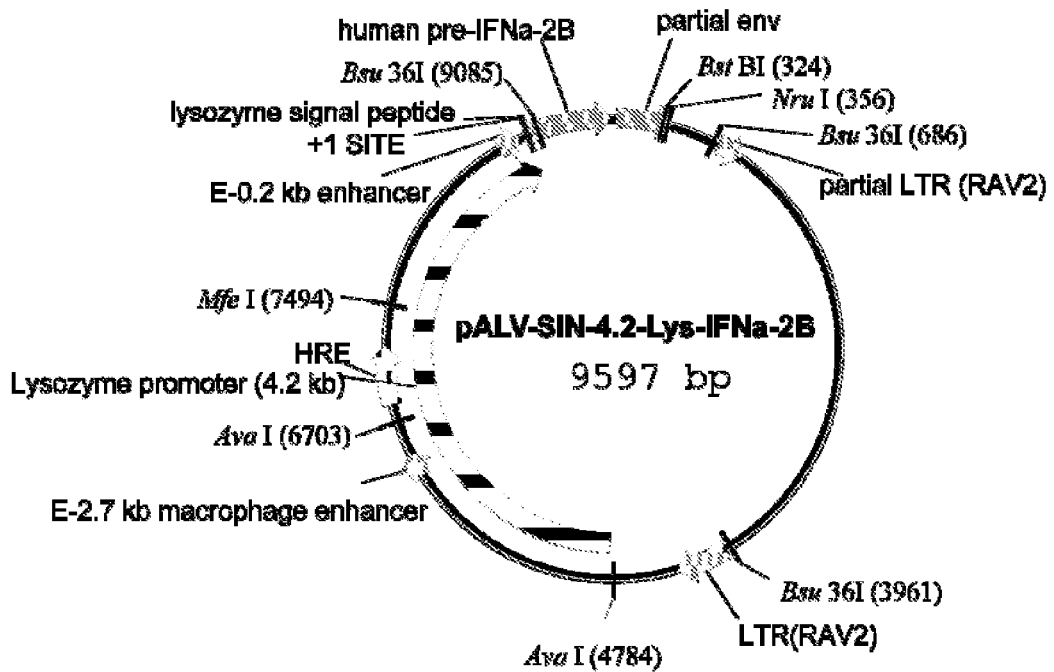
FIG. 1 shows a circular map of the pALV-SIN-4.2-Lys-IFNa-2B vector. The sequence of pALV-SIN-4.2-Lys-IFNa-2B is shown in SEQ ID NO: 1.

The term "animal" is used herein to include all vertebrate animals, including avians and may include humans. It also includes an individual animal in all stages of development, including embryonic and fetal stages.

The term "antibody" as used herein refers to polyclonal and monoclonal antibodies and functional fragments thereof. An antibody includes modified or derivatised antibody variants that retain the ability to specifically bind an epitope. Antibodies are capable of selectively binding to a target antigen or epitope. Antibodies may include, but are not limited to polyclonal antibodies, monoclonal antibodies (mAbs), humanized and other chimeric antibodies, single chain antibodies (scFvs), Fab fragments, F(ab')$_2$ fragments and disulfide-linked Fvs (sdFv) fragments.

The term "avian" as used herein refers to any species, subspecies or strain of organism of the taxonomic class ayes, such as, but not limited to, such organisms as chicken, turkey, duck, goose, quail, pheasants, parrots, finches, hawks, crows and ratites including ostrich, emu and cassowary. The term includes the various known strains of Gallus gallus, or chickens, (for example, White Leghorn, Brown Leghorn, Barred-Rock, Sussex, New Hampshire, Rhode Island, Ausstralorp, Minorca, Amrox, California Gray, Italian Partridge-colored), as well as strains of turkeys, pheasants, quails, duck, ostriches and other poultry commonly bred in commercial quantities.

The phrases "based on" or "derived from" as in a retroviral vector being based on or derived from a particular retrovirus or based on a nucleotide sequence of a particular retrovirus mean that the genome of the retroviral vector contains a substantial portion of the nucleotide sequence of the genome of the particular retrovirus. The substantial portion may be a particular gene or nucleotide sequence such as the nucleotide sequence encoding the gag, pol and/or env proteins or other structural or functional nucleotide sequence of the virus genome such as sequences encoding the LTRs or may be substantially the complete retrovirus genome, for example, most (e.g., more than 60% or more than 70% or more than 80% or more than 90%) or all of the retrovirus genome, as will be apparent from the context in the specification as the knowledge of one skilled in the art. Examples of retroviral vectors that are based on or derived from a retrovirus are the NL retroviral vectors (e.g., NLB) which are based on the ALV retrovirus as disclosed in Cosset et al, Journal of Virology (1991) vol 65, p 3388-3394.

The terms "coding sequence" and "coding region" as used herein refer to nucleotide sequences and nucleic acid sequences, including both RNA and DNA, that encode genetic information for the synthesis of an RNA, a protein, or any portion of an RNA or protein. Nucleotide sequences that are not naturally part of a particular organism's genome are referred to as "foreign nucleotide sequences," "heterologous nucleotide sequences" or "exogenous nucleotide sequences". "Heterologous proteins" are proteins encoded by foreign, heterologous or exogenous nucleotide sequences and therefore are often not naturally expressed in the cell. A nucleotide sequence that has been isolated and then reintroduced into the same type (e.g., same species) of organism is not considered to be a naturally occurring part of a particular organism's genome and is therefore considered exogenous or heterologous.

The term "construct" as used herein refers to a linear or circular nucleotide sequence such as DNA that has been assembled from more than one segments of nucleotide sequence which have been isolated from a natural source or have been chemically synthesized, or combinations thereof.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine The term "cytokine" as used herein refers to any secreted amino acid sequence that affects the functions of cells and is a molecule that modulates interactions between cells in the immune, inflammatory or hematopoietic responses. A cytokine includes, but is not limited to, monokines and lymphokines regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-alpha) and Tumor Necrosis Factor beta (TNF-beta).

The term "expressed" or "expression" as used herein refers to the transcription from a gene to give an RNA nucleic acid molecule at least complementary in part to a region of one of the two nucleic acid strands of the gene. The term "expressed" or "expression" as used herein can also refer to the translation of RNA to produce a protein or peptide.

The term "expression vector" as used herein refers to a nucleic acid vector that comprises a gene expression controlling region, such as a promoter or promoter component, operably linked to a nucleotide sequence coding at least one polypeptide.

The term "fragment" as used herein can refer to, for example, an at least about 10, 20, 50, 75, 100, 150, 200, 250, 300, 500, 1,000, 2,000, 5,000, 6,000, 8,000, 10,000, 20,000, 30,000, 40,000, 50,000 or 60,000 nucleotide long portion of a nucleic acid that has been constructed artificially (e.g., by chemical synthesis) or by cleaving a natural product into multiple pieces, using restriction endonucleases or mechanical shearing, or enzymatically, for example, by PCR or any other polymerizing technique known in the art, or expressed in a host cell by recombinant nucleic acid technology known to one of skill in the art. The term "fragment" as used herein may also refer to, for example, an at least about 5, 10, 20, 30, 40, 50, 75, 100, 150, 200, 250, 300, 400, 500, 1,000, 2,000, 5,000, 6,000, 8,000 or 10,000 amino acid portion of an amino acid sequence, which portion is cleaved from a naturally occurring amino acid sequence by proteolytic cleavage by at least one protease, or is a portion of the naturally occurring amino acid sequence synthesized by chemical methods or using recombinant DNA technology (e.g., expressed from a portion of the nucleotide sequence encoding the naturally occurring amino acid sequence) known to one of skill in the art. "Fragment" may also refer to a portion, for example, of about 5%, about 10%, about 20%, about 30%, about 40%, about 50%, about 60%, about 70%, about 80% about 90% about 95% or about 99% of a particular nucleotide sequence or amino acid sequence.

"Functional portion" or "functional fragment" are used interchangeably and as used herein mean a portion or fragment of a whole capable of performing, in whole or in part, a function of the whole. For example, a biologically functional portion of a molecule means a portion of the molecule that performs a biological function of the whole or intact molecule. For example, a functional portion of a gene expression controlling region is a fragment or portion of the specified gene expression controlling region that, in whole or in part, regulates or controls gene expression (e.g., facilitates either in whole or in part) in a biological system (e.g., a promoter). Functional portions may be of any useful size. For example, a functional fragment may range in size from about 20 bases in length to a length equal to the entire length of the specified sequence minus one nucleotide. In another example, a functional fragment may range in size from about 50 bases in length to a length equal to the entire length of the specified sequence minus one nucleotide. In another example, a functional fragment may range in size from about 50 bases in length to about 20 kb in length. In another example, a functional fragment may range in size from about 500 bases in length to about 20 kb in length. In another example, a functional fragment may range in size from about 1 kb in length to about 20 kb in length. In another example, a functional fragment may range in size from about 0.1 kb in length to about 10 kb in length. In another example, a functional fragment may range in size from about 20 bases kb in length to about 10 kb in length.

The term "gene expression controlling region" as used herein refers to nucleotide sequences that are associated with a coding sequence and which regulate, in whole or in part, expression of the coding sequence, for example, regulate, in whole or in part, the transcription of the coding sequence. Gene expression controlling regions may be isolated from a naturally occurring source or may be chemically synthesized and can be incorporated into a nucleic acid vector to enable regulated transcription in appropriate cells. The "gene expression controlling regions" may precede, but is not limited to preceding, the region of a nucleic acid sequence that is in the region 5' of the end of a coding sequence that may be transcribed into mRNA.

The terms "heterologous", "exogenous" and "foreign" are used interchangeably herein and in general refer to a biomolecule such as a nucleic acid or a protein that is not normally found in a certain organism or in a certain cell, tissue or other component contained in or produced by an organism. For example, a protein that is heterologous or exogenous to an egg is a protein that is not normally found in the egg. As used herein, the terms "heterologous", "exogenous" and "foreign" with reference to nucleic acids, such as DNA and RNA, are used interchangeably and refer to nucleic acid that does not occur naturally as part of a chromosome, a genome or cell in which it is present or which is found in a location(s) and/or in amounts that differ from the location(s) and/or amounts in which it occurs in nature. It can be nucleic acid that is not endogenous to the genome, chromosome or cell and has been exogenously introduced into the genome, chromosome or cell. Examples of heterologous DNA include, but are not limited to, a DNA comprising a gene expression control region and DNA that encodes a product or products, for example, RNA or protein product. Examples of heterologous DNA include, but are not limited to, gene expression controlling regions or promoters disclosed herein once isolated from the avian and as used thereafter, e.g., after re-introduction into an avian genome.

The term "isolated nucleic acid" as used herein covers, for example, (a) a DNA which has the sequence of part of a naturally occurring genomic molecule but is not flanked by at least one of the sequences that flank that part of the molecule in the genome of the species in which it naturally occurs; (b) a nucleic acid which has been incorporated into a vector or into the genomic DNA of a prokaryote or eukaryote in a manner such that the resulting vector or genomic DNA is not identical to naturally occurring DNA from which the nucleic acid was obtained; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions.

The term "nucleic acid" as used herein refers to any linear or sequential array of nucleotides and nucleosides, for example cDNA, genomic DNA, mRNA, tRNA, oligonucleotides, oligonucleosides and derivatives thereof. For ease of discussion, non-naturally occurring nucleic acids may be referred to herein as constructs. Nucleic acids can include bacterial plasmid vectors including expression, cloning, cosmid and transformation vectors such as, animal viral vectors such as, but not limited to, modified adenovirus, influenza virus, polio virus, pox virus, retroviruses such as avian leukosis virus (ALV) retroviral vector, a murine leukemia virus (MLV) retroviral vector, and a lentivirus vector, and the like and fragments thereof. In addition, the nucleic acid can be an LTR of an avian leukosis virus (ALV) retroviral vector, a murine leukemia virus (MLV) retroviral vector, or a lentivirus vector and fragments thereof. Nucleic acids can also include NL vectors such as NLB, NLD, NLA and fragments thereof and synthetic oligonucleotides such as chemically synthesized DNA or RNA. Nucleic acids can include modified or derivatised nucleotides and nucleosides such as, but not limited to, halogenated nucleotides such as, but not only, 5-bromouracil, and derivatised nucleotides such as biotin-labeled nucleotides.

The term "vector" and "nucleic acid vector" as used herein refers to a natural or synthetic single or double stranded plasmid or viral nucleic acid molecule that can be transfected or transformed into cells and replicate independently of, or within, the host cell genome. A circular double stranded vector can be linearized by treatment with an appropriate restriction enzyme based on the nucleotide sequence of the vector. A nucleic acid can be inserted into a vector by cutting the vector with restriction enzymes and ligating the desired pieces together.

The term "operably linked" refers to an arrangement of elements wherein the components so described are configured so as to perform their usual function. Gene expression controlling regions or promoters (e.g., promoter components) operably linked to a coding sequence are capable of effecting the expression of the coding sequence. The controlling sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "oviduct specific promoter" as used herein refers to promoters and promoter components which are functional, i.e., provide for transcription of a coding sequence, to a large extent, for example, primarily (i.e., more than 50% of the transcription product produced in the animal by a particular promoter type being produced in oviduct cells) or exclusively in oviduct cells of a bird. Examples of oviduct specific promoters include, ovalbumin promoter, ovomucoid promoter, ovoinhibitor promoter, lysozyme promoter and ovotransferrin promoter and functional portions of these promoters, e.g., promoter components.

The terms "percent sequence identity" and "percent identity" as used in, for example, "% identical" and "percent sequence homology" and "percent homology", as used in, for example, "% homology" and "percent sequence similarity" each refer to the degree of sequence matching between two nucleic acid sequences or two amino acid sequences as determined using the algorithm of Karlin & Attschul (1990) Proc. Natl. Acad. Sci. 87: 2264-2268, modified as in Karlin & Attschul (1993) Proc. Natl. Acad. Sci. 90: 5873-5877. Such an algorithm is incorporated into the NBLAST and XBLAST programs of Attschul et al. (1990) T. Mol. Biol. Q15: 403-410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference amino acid sequence. To obtain gapped alignments for comparison purposes, Gapped BLAST is utilized as described in Attschul et al. (1997) Nucl. Acids Res. 25: 3389-3402. When utilizing BLAST and Gapped BLAST programs, the default parameters of the respective programs (e.g. XBLAST and NBLAST) are used. Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The terms "polynucleotide," "oligonucleotide", "nucleotide sequence" and "nucleic acid sequence" can be used interchangeably herein and include, but are not limited to, coding sequences, i.e., polynucleotide(s) or nucleic acid sequence(s) which are transcribed and translated into polypeptide in vitro or in vivo when placed under the control of appropriate regulatory or control sequences; controlling sequences, e.g., translational start and stop codons, promoter sequences, ribosome binding sites, polyadenylation signals, transcription factor binding sites, transcription termination sequences, upstream and downstream regulatory domains, enhancers, silencers, DNA sequences to which a transcription factor(s) binds and alters the activity of a gene's promoter either positively (induction) or negatively (repression) and the like. No limitation as to length or to synthetic origin are suggested by the terms described herein.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" includes polypeptides as defined above that are encoded by nucleic acids, produced through recombinant technology (e.g., isolated from a transgenic bird), or synthesized. The term "polypeptides" further contemplates polypeptides as defined above that include chemically modified amino acids or amino acids covalently or noncovalently linked to labeling ligands.

The term "promoter" as used herein refers to a DNA sequence useful to initiate transcription initiation by an RNA polymerase in an avian cell. A "promoter component" is a DNA sequence that can, by itself or, in combination with other DNA sequences effect or facilitate transcription. Specific promoter components such as ovalbumin promoter components, ovomucoid promoter components and lysozyme promoter components and other promoters and promoter components disclosed and claimed herein do not describe a specific promoter sequence. Rather, they encompass any sequence or sequence fragment of the respective promoter that is useful to effect or facilitate transcription of a coding sequence. For example, an ovomucoid promoter component includes, without limitation, the about 1.8 kb, the about 3.9 kb and the about 10 kb ovomucoid promoters disclosed in U.S. publication Ser. No. 11/649,543, published May 17, 2007, which is incorporated in its entirety herein by reference. "Promoter components" can also encompass rearranged gene expression controlling regions which function to initiate RNA transcription and hybrid DNA molecules composed of naturally occurring DNA sequences and/or synthetic DNA sequences which function to initiate RNA transcription.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, the term "regulatory sequences" includes promoters, enhancers, and other elements that may control gene expression.

An "SC negative vector" is a vector that does not contain a selectable or screenable cassette marker having a functional promoter. The promoter may be deleted in whole or in part or may be inactivated by a nucleotide sequence insertion. Screenable cassettes include, without limitation, DNA sequences for antibiotic resistance markers such as neomycin resistance and DNA sequences for other selectable markers such as GFP or lacZ.

A "SIN vector" is a self-inactivating vector. In particular, a SIN vector is a retroviral vector having an altered genome such that upon integration into genomic DNA of the target cell (e.g., avian embryo cells) the 5' LTR of the integrated retroviral vector will not function as a promoter. For example, a portion or all of the nucleotide sequence of the retroviral vector that results in the U3 region of the 5' LTR of the retroviral vector once integrated may be deleted or altered in order to reduce or eliminate promoter activity of the 5' LTR. In certain examples, deletion of the CAAT box and/or the TAATA box from U3 of the 5' LTR can result in a SIN vector, as is understood in the art.

A "SIN/SC negative vector" is a vector, i.e., a retroviral vector, that is both a SIN vector and a SC negative vector.

The term "sense strand" as used herein refers to a single stranded DNA molecule from a genomic DNA that may be transcribed into RNA and translated into the natural polypeptide product of the gene. The term "antisense strand" as used herein refers to the single strand DNA molecule of a genomic DNA that is complementary with the sense strand of the gene.

A "therapeutic protein" or "pharmaceutical protein" is a substance that, in whole or in part, makes up a drug. In particular, "therapeutic proteins" and "pharmaceutical proteins" include an amino acid sequence which in whole or in part makes up a drug.

The terms "transcription regulatory sequences" and "gene expression control regions" and "promoter components" as used herein refer to nucleotide sequences that are associated with a nucleic acid sequence and which regulate the transcriptional expression of a coding sequence. Exemplary transcription regulatory sequences include enhancer elements, hormone response elements, steroid response elements, negative regulatory elements, and the like. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only a calcium or magnesium salt, an electric field, detergent, or liposome mediated transfection, to render the host cell competent for the uptake of the nucleic acid molecules.

As used herein, a "transgenic animal" is any non-human animal, such as an avian species, including the chicken, in which one or more of the cells of the avian may contain heterologous nucleic acid introduced by way of human intervention, such as by transgenic techniques known in the art (see, for example, US patent publication No. 2007/0243165, published Oct. 18, 2007, the disclosure of which is incorporated in its entirety herein by reference) including those disclosed herein. The nucleic acid is introduced into an animal, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animal, the transgene can cause cells to express a recombinant form of the target protein or polypeptide. The terms "chimeric animal" or "mosaic animal" are used herein to refer to animals in which a transgene is found, or in which the recombinant nucleotide sequence is expressed in some but not all cells of the animal. A germ-line chimeric animal contains a transgene in its germ cells and can give rise to a transgenic animal in which most or all cells of the offspring animal will contain the transgene.

As used herein, the term "transgene" means a nucleic acid sequence (encoding, for example, a human protein) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene according to the present invention can include a vector of the invention (e.g., SIN vector) which contains sequences useful for exogenous protein production in an avian (e.g., in an avian oviduct).

Techniques useful for isolating and characterizing the nucleic acids and proteins of the present invention are well known to those of skill in the art and standard molecular biology and biochemical manuals may be consulted to select suitable protocols for use without undue experimentation. See, for example, Sambrook et al, 1989, "Molecular Cloning: A Laboratory Manual", 2nd ed., Cold Spring Harbor, the content of which is herein incorporated by reference in its entirety.

Abbreviations:

Abbreviations used herein may include the following: aa, amino acid(s); bp, base pair(s); cDNA, DNA complementary to an RNA; nt, nucleotide(s); kb, 1000 base pairs; μg, microgram; ml, milliliter; ng, nanogram.

Description:

SIN vectors designed and used in accordance with the invention can reduce or eliminate promoter interference of promoters of interest which are employed in transgenic avians. In a particularly useful embodiment, the promoters (i.e., promoter components) of interest preferentially express their gene product in oviduct cells or oviduct tissue, e.g., oviduct specific promoters. Examples of such promoters (e.g., promoter components) include but are not limited to, functional portions of the ovalbumin, lysozyme, conalbumin (i.e., ovotransferrin), ovomucoid, ovomucin, and/or ovoinhibitor gene expression controlling regions or promoter regions. In one embodiment, the promoter of interest is a combination or a fusion of one or more promoters or a fusion of a fragment of one or more promoters such as ovalbumin, lysozyme, conalbumin (i.e., ovotransferrin), ovomucoid, ovomucin, and/or ovoinhibitor promoters with another promoter or promoter fragment such as a viral promoter (e.g., an LTR promoter).

SIN vectors have been shown to be particularly useful with oviduct specific promoters. Without wishing to limit the invention to any particular theory or mechanism of operation it is believed that oviduct specific promoters can be particularly susceptible to influences of a retroviral LTR promoter. As a result, SIN vectors are particularly useful when employed in combination with avian oviduct specific promoters.

In one particularly useful embodiment, a SIN vector is produced in which an interfering promoter (e.g., an LTR promoter) that can at least partially inhibit transcription of a coding sequence operably linked to an oviduct specific promoter of the invention is inactivated, for example, by a deletion, insertion or transposition of all or part of the interfering promoter sequence. For example, in the vector pALV-SIN-4.2-Lys-IFNa-2B, shown in FIG. 1, the 3' RAV2 LTR has a deletion in the enhancer such that when the retroviral region integrates, the 5' LTR is inactivated, as is understood in the art. For a detailed diagrammatic of an LTR deletion, see FIG. 10.

In one useful embodiment of the invention, a SIN vector is employed that is also an SC negative vector to produce a SIN/SC negative vector. The combination of negative vector and SIN vector can result in a vector with a substantially reduced amount of promoter interference compared to a vector that is only a SIN vector or only a SC negative vector. For example, pALV-SIN-4.2-Lys-IFNa-2B as well as other SIN vectors disclosed in the Examples also lacks an antibiotic resistance marker making it both a SC negative vector and a SIN vector.

SIN vectors, SC negative vectors and SIN/SC negative vectors are contemplated for use in accordance with the invention in any useful avian such as chicken, quail and turkey to produce chimeras including germ-line chimeras and progeny birds produced using breeding techniques such as those known to practitioners of ordinary skill in the art. In addition, it is contemplated that an SC negative retroviral vector (which is a non-SIN vector) will also enhance or increase the quantity of exogenous protein produced in a transgenic avian relative to a transgenic avian produced with essentially the same retroviral vector that is not a SC negative vector.

Without wishing to limit the invention to any particular theory or mechanism of operation it is believed that the lack of a selectable marker cassette decreases the presence of promoter elements such as enhancers which would otherwise be in cis and in close proximity to the promoter employed for exogenous protein production in avian oviduct cells (e.g., oviduct specific promoters). This close proximity may allow for interference by the transcription regulating elements of the marker gene with the promoter of interest, i.e., the promoter employed for exogenous protein production. However, the invention contemplates that marker gene coding sequences, for example, and without limitation, neomycin resistance coding sequence and beta lactamase coding sequence, may be operably linked to a promoter (i.e., second promoter) which does not interfere with the promoter employed for exogenous protein production in avian oviduct cells (i.e., first promoter). For example, it is contemplated that if the marker promoter and the promoter of interest are the same or similar promoters, interference by the selectable cassette will be minimized or eliminated. For example, a second ovalbumin promoter operably linked to a marker gene coding sequence may not interfere with a first ovalbumin promoter employed for exogenous protein production in avian oviduct cells.

The invention contemplates the employment of any useful oviduct specific promoter, and oviduct specific promoter fragments, in vectors of the invention for exogenous protein expression in avians. For example, promoters and useful (e.g., functional) fragments of promoters (e.g., promoter components) disclosed in US patent publication No. 2005/0176047, filed Jan. 31, 2005, the disclosure of which is incorporated in its entirety herein by reference, and US patent publication No. 2007/0124829, filed Jan. 26, 2007, the disclosure of which is incorporated in its entirety herein by reference, and US patent publication No. 2006/0130170, filed Dec. 11, 2003, the disclosure of which is incorporated in its entirety herein by reference, are contemplated for use in conjunction with SIN vectors and SC negative vectors and SIN/SC negative vectors in accordance with the invention.

The invention also contemplates other promoters and transcriptionally functional portions thereof (e.g., promoter components) for use as promoters of interest in accordance with the invention such as a cytomegalovirus (CMV) promoter, a rous-sarcoma virus (RSV) promoter, a β-actin promoter (e.g., a chicken β-actin promoter) a murine leukemia virus (MLV) promoter, and a mouse mammary tumor virus (MMTV) promoter.

The invention also includes various ovalbumin promoter components which are contemplated for use in producing exogenous proteins in transgenic avians. Each of the promoters disclosed herein are contemplated for use in vectors in accordance with the invention.

Examples of vectors of the invention which contain recombinant ovalbumin DNA are shown below. The fragments are listed top to bottom in the 5' to 3' linear order in which they are present on a single DNA molecule. For example, the 3' end of the 3.5 kb OV fragment of sequence 1 would be covalently linked to the 5' end of the 5' UTR-5' portion and the 3' end of the 5' UTR-5' portion would be covalently linked to the 5' end of 5' UTR-3' portion.

1. pSIN-OV-3.5-CSI
   3.5 kb OV fragment (includes DHS I, II & III)
   5' UTR-5' portion (from Exon L)
   5' UTR-3' portion (from Exon 1)
2. pSIN-OV-3.5-Int-CSI-inv
   3.5 kb OV fragment (includes DHS I, II & III)
   5' UTR-5' portion (from Exon L)
   Intron A
   5' UTR-3' portion (from Exon 1)
   3' UTR
3. pSIN-OV-3.5-Int-CSI
   3.5 kb OV fragment (includes DHS I, II & III)
   5' UTR-5' portion (from Exon L)
   Intron A
   5' UTR-3' portion (from Exon 1)
4. pSIN-OV-3.5-CSI-UTR-inv
   3.5 kb OV fragment (includes DHS I, II & III)
   5' UTR-5' portion (from Exon L)
   5' UTR-3' portion (from Exon 1)
   3' UTR
5. pSIN-OV-3.5-Int-CSI-LUTR-inv
   3.5 kb OV fragment (includes DHS I, II & III)
   5' UTR-5' portion (from Exon L)
   Intron A
   5' UTR-3' portion (from Exon 1)
   3' UTR/DHS A (bp 13576 to 15163 of FIG. 8);
6. pSIN-OV-3.5-CSI-LUTR-inv
   3.5 kb OV fragment (includes DHS I, II & III)
   5' UTR-5' portion (from Exon L)
   5' UTR-3' portion (from Exon 1)
   3' UTR/DHS A (bp 13576 to 15163 of FIG. 8);
7. pSIN-OV-3.5-Int-CSI-RRE
   3.5 kb OV fragment (includes DHS I, II & III)
   5' UTR-5' portion (from Exon L)
   Intron A
   5' UTR-3' portion (from Exon 1)
   partial 3' UTR
   RRE (Rev response element) FIG. 9a Construct 7 includes RRE to allow transport of the unspliced RNA genome to the cytoplasm and thus may enhance packaging of intact retroviral RNA. RRE is only active in presence of the Rev protein. Rev activity is provided in the form of DNA encoding the Rev, RNA encoding the Rev, and/or the Rev protein, which is well known in the art and commercially available (e.g., Invitrogen, Inc.), during the transient transfection of retroviral components. Thus the intron will be present in the transgene contained in the genome of the transgenic bird produced by the virus particles (the rev protein is not present in the cells of the transgenic bird). As a result the RNA should be spliced in the oviduct cells of a laying hen resulting in an enhanced level of protein expression compared to a same transgenic bird having the same transgene without the intron.

8. pSIN-CTE-OV-3.5-Int-CSI
   ALV CTE (FIG. 9b) inserted 5' of 3.5 kb OV fragment
   3.5 kb OV fragment (includes DHS I, II & III)
   5' UTR-5' portion (from Exon L)
   Intron A
   5' UTR-3' portion (from Exon 1)
   partial 3' UTR Coordinates for some of the elements for the above eight vectors are described elsewhere in the application. For example, coordinates of sequences from the ovalbumin nucleotide sequence are described in the Summary section above. CSI means a coding sequence of interest, i.e., nucleotide sequence encoding the protein desired to be expressed in a transgenic avian oviduct.

SIN vectors, SIN/SC negative vectors and SC negative vectors for use in accordance with the invention include vectors such as Avian Leukemia/Leukosis Viruses (ALV), for example, and without limitation, RAV-0, RAV-1, RAV-2; Avian Sarcoma Viruses (ASV); Avian Sarcoma/Acute Leukemia Viruses (ASLV) including, without limitation, Rous Sarcoma Virus (RSV); Fujinami Sarcoma Viruses (FSV); Avian Myeloblastosis Viruses (AMV); Avian Erythroblastosis Viruses (AEV); Avian Myelocytomatosis Viruses (MCV), for example, and without limitation, MC29; Reticuloendotheliosis Viruses (REV), for example, and without limitation, Spleen Necrosis Virus (SNV). The invention also contemplates other useful retroviral vector, including, without limitation, retroviral vectors based upon Murine Leukemia Viruses (MLV); Molony Murine Sarcoma Viruses (MMSV); Moloney Murine Leukemia Viruses (MMLV); and lentiviruses (e.g., human immunodeficiency virus (HIV), feline immunodeficiency virus (FIV), bovine immunodeficiency virus (BIV) and simian immunodeficiency virus (SIV) which are altered to be SIN vectors, SIN/SC negative vectors or SC negative vectors as is understood by a practitioner of ordinary skill in the art.

In one very specific embodiment, a portion of the 5' LTR of a modified ALV vector disclosed in Cosset et al, J of Virology (1991) vol 65, no. 6, p 3388-3394, the disclosure of which is incorporated in its entirety herein by reference, is deleted to produce a SIN vector. In particular, nucleotides 1 to 173 were deleted from the ALV based vector LTR sequence shown in SEQ ID NO: 29. Specific deletions from 5' LTR sequences useful to produce SIN vectors from other vectors which can be used in avian transgenesis can be determined by a practitioner of ordinary skill in the art.

In one particularly useful embodiment, the invention is drawn to the production of therapeutic proteins which may be produced in the oviduct of a transgenic avian, such as a chicken, in accordance with the invention. Exemplary proteins for production in accordance with the invention include, without limitation, erythropoietin, GM-CSF, interferon β, fusion protein, CTLA4-Fc fusion protein, growth hormones, cytokines, structural proteins, interferon, lysozyme, β-casein, albumin, α-1 antitrypsin, antithrombin III, collagen, factors VIII, IX, X (and the like), fibrinogen, lactoferrin, protein C, tissue-type plasminogen activator (tPA), somatotropin, and chymotrypsin, immunoglobulins, antibodies, immunotoxins, factor VIII, b-domain deleted factor VIII, factor VIIa, factor IX, anticoagulants, hirudin, alteplase, tpa, reteplase, tpa-3 of 5 domains deleted, insulin, insulin lispro, insulin aspart, insulin glargine, long-acting insulin analogs, glucagons, tsh, follitropin-beta, fsh, pdgh, ifn-beta, ifn-alpha 1, ifn-alpha 2, ifn-beta, ifn-beta 1b, ifn-beta 1a, ifn-gamma, ifn-gamma 1b, il-2, il-11, hbsag, ospa, dornase-alpha dnase, beta glucocerebrosidase, tnf-alpha, il-2-diptheria toxin fusion protein, tnfr-lgg fragment fusion protein laronidase, dnaases, alefacept, tositumomab, murine mab, alemtuzumab, rasburicase, agalsidase beta, teriparatide, parathyroid hormone derivatives, adalimumab (lgg1), anakinra, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, luteinizing hormone, chorionic gonadotropin, hypothalmic releasing factors, etanercept, antidiuretic hormones, prolactin and thyroid stimulating hormone, an immunoglobulin polypeptide, immunoglobulin polypeptide D region, immunoglobulin polypeptide J region, immunoglobulin polypeptide C region, immunoglobulin light chain, immunoglobulin heavy chain, an immunoglobulin heavy chain variable region, an immunoglobulin light chain variable region and a linker peptide. Production of each of these, and other, proteins is contemplated using methods, vectors and promoters of the invention.

The present invention is further illustrated by the following examples, which are provided by way of illustration and should not be construed as limiting. The contents of all references, published patents and patents cited throughout the present application are hereby incorporated by reference in their entireties.

Example 1

Production of pALV-SIN-4.2-Lys-IFNa-2B

The vector pALV-SIN-4.2-Lys-IFNa-2B (shown in FIG. 1) was constructed and is shown in FIG. 1. The sequence of pALV-SIN-4.2-Lys-IFNa-2B is shown in SEQ ID NO: 1. The 4.2 Kb lysozyme promoter spans from nucleotides 4810 to 9008 of SEQ ID NO: 1. The lysozyme signal peptide coding sequence spans from nucleotides 9037 to 9090 of SEQ ID NO: 1. The interferon alpha 2b coding sequence spans from nucleotides 9091 to 9585 of SEQ ID NO: 1. Other components of the sequence include LTRs spanning from nucleotides 4000 to 4345 and from nucleotides 725 to 897 of SEQ ID NO: 1.

pALV-SIN-4.2-Lys-IFNa-2B can be constructed by a variety of methods which are apparent to a practitioner of skill in the art. However, the method believed to be the most useful for making the vector is as follows: A 3427 bp region of pNLB-CMV-IFN-alpha2B (disclosed in U.S. patent application Ser. No. 11/167,052, filed Jun. 24, 2005, the disclosure of which is incorporated in its entirety herein by reference) is PCR amplified using primers ATGCGCGCATTGGTAAT-TGATCGGCTGG (Primer ALV-SIN-1, SEQ ID NO: 2) and ATATGCGGCCGCGGTACCGC-CCGGGCATCGATATCAAGCTTACGGTTCACT A AAC-GAGCTCTGCTTATATAGACCTCCCA (Primer ALV-SIN-2, SEQ ID NO: 3). The product is digested with BssHII and Not I resulting in a 3428 bp fragment which can be isolated by gel purification. A 1436 bp region of pNLB-CMV-IFN-alpha2B is PCR amplified with primers ATATGCGGC-CGCGTCGACGGCCGGCCAGATCTGCT-GAGCCGGTCGCTACCA TTACCAGT (Primer ALV-SIN-3, SEQ ID NO: 4) and ATACGCGTATTCCCTAACGATCACGTCG (Primer ALV-SIN-4, SEQ ID NO: 5). The resulting product is digested with Not I and Mlu I yielding a 1438 bp fragment which is isolated by gel purification. A Bluescript II SK vector containing a BssHII stuffer fragment is digested with BssHII resulting in a linearized Bluescript vector of 2788 bp which is gel purified and then ligated to the 3428 bp and 1438 bp PCR products to yield JCR.A108.49.5.24.

JCR.A108.49.5.24 is digested with Hind III and the resulting 6823 bp fragment is circularized by ligation to yield JCR.A108.76.1.1.

A 1175 bp region of JCR.A108.76.1.1 is PCR amplified with primers CTGAAGTGTAAGGAATGTAAG (Primer ALV-SIN-5, SEQ ID NO: 6) and GCGCGTCTCATC-CCCCTCCCTATGCAAAAG (Primer ALV-SIN-6, SEQ ID NO: 7) and the resulting fragment is digested with Blp I and Esp3I producing a 1030 bp fragment which is isolated by gel purification. A 660 bp region of JCR.A108.76.1.1 is PCR amplified with primers GGGCGTCTCAGGGACGGATTG-GACGAACCACTGAATT (Primer ALV-SIN-7, SEQ ID NO: 8) and TTAGTGCTTTACGGCACCTC (Primer ALV-SIN-8, SEQ ID NO: 9) and digested with Esp3I and DraIII resulting in a 596 bp fragment which is isolated by gel purification. JCR.A108.76.1.1 is digested with DraIII and Blp I and the 5024 bp linear vector is ligated to the 1030 and 596 bp PCR fragments to produce pALV-SIN.

pALV-SIN is digested with BamHI and the 4795 bp linear vector is isolated by gel purification. A 4815 bp region of JCR.115.93.1.2 (disclosed in US patent publication No. 2007/0124829, published May 31, 2007) is PCR amplified with primers GACGGATCCGATACCGTC-CCTATTTTTGTGTTTGCTTC (Primer ALV-SIN-9, SEQ ID NO: 10) and TAACGGATCCTAGACTTTTTACTCCT-TAGA (Primer ALV-SIN-10, SEQ ID NO: 11) and is digested with BamHI. The resulting 4802 fragment is ligated to the 4795 bp linear pALV-SIN to produce pALV-SIN-4.0-Lys-IFNa-2B.

Example 2

Production of Transgenic Quail Using pALV-SIN-4.2-Lys-IFNa-2B

Transduction particles of the vector pALV-SIN-4.2-Lys-IFNa-2B were produced in fibroblast cells as disclosed in US patent publication No. 2007/0077650, published Apr. 5, 2007, entitled: Rapid Production of High Titer Virus, the disclosure of which is incorporated in its entirety herein by reference.

Fertilized Japanese quail eggs were windowed essentially according to the Speksnijder procedure disclosed in U.S. Pat. No. 5,897,998, the disclosure of which is incorporated in its entirety herein by reference. Eighty eggs were injected in the subgerminal cavity with about 7 microliters (approximately $7 \times 10^4$ viral particles total) of pALV-SIN-4.2-Lys-IFNa-2B transducing particles per egg. Since no selectable marker is used in pALV-SIN-4.2-Lys-IFNa-2B, the concentration of viral particles is estimated based upon past results for viral particle production where a selectable cassette or marker was used in the vector which allowed for particle quantification. Sixteen chicks hatched about 18 days after injection and human IFN levels were measured by IFN ELISA from serum samples collected from chicks 12 weeks after hatch. None were positive for the IFN protein in the serum.

In order to identify G0 quail which contained the interferon alpha 2 coding sequence containing transgene in their genome, DNA was extracted from blood of the birds and the DNA samples were subjected to Taqman® analysis on a 7700 Sequence Detector (Perkin Elmer).

Figure 2:
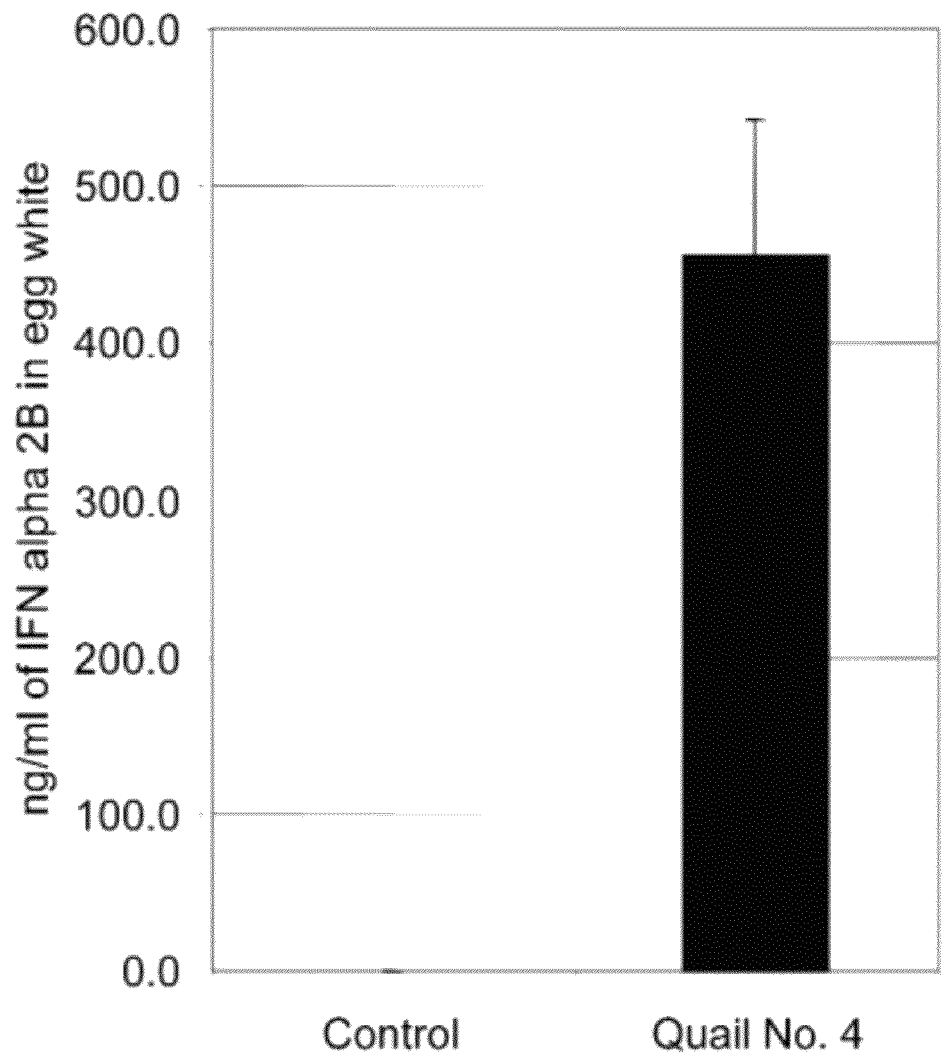
FIG. 2 is a bar graph illustrating expression levels of IFNa in the egg white of a transgenic quail. G0 quail was produced by injection of pALV-SIN-4.0-Lys-IFNa-2B retroviral vector transduction particles into Japanese quail embryos.

Eggs from eight G0 quail were tested for the presence of the IFN protein in the egg white by ELISA. Quail No. 4 was found to have significant levels of IFN in egg white from her eggs. FIG. 2 shows a bar graph illustrating expression levels of IFN in the egg white of Quail No. 4. Quail No. 4 expressed IFN-alpha-2 at 0.45 µg/ml of egg white, which is a high level of expression for a G0 avian. There was no interferon alpha 2 detected in the blood of Quail No. 4 which is particularly significant. For example, in certain instances the recombinant protein may be harmful to the development or health of the avian when present in the blood which can kill the bird or can lead to reduced levels of protein production.

Example 3

Production of Transgenic Quail Using pALV-SIN-6.5-Lys-IFNa-2B

The 4.2 kb lysozyme promoter of vector pALV-SIN-4.2-Lys-IFNa-2B is removed and replaced with a 6.5 kb lysozyme promoter corresponding to about nucleotides 5363 to 11863 of SEQ ID NO: 12, using standard methodologies known to practitioners of skill in the art, resulting in pALV-SIN-6.5-Lys-IFNa-2B. Transduction particles of the new vector pALV-SIN-6.5-Lys-IFNa-2B are produced as disclosed in US patent publication No. 2007/0077650, published Apr. 5, 2007.

Fertilized chicken eggs or Japanese quail eggs are windowed and about $7 \times 10^4$ pALV-SIN-6.5-Lys-IFNa-2B transducing particles are injected into the subgerminal cavity of each egg. Eggs hatch 21 or 18 days after injection and chimeric birds are identified that contain the active transgene in their genome, as described in Example 2. Fully transgenic G1 birds which contain the transgene in their genome are produced from chimeras using methods known in the art, i.e., crossing male chimeras with non-transgenic females.

Example 4

Production of Vector pSIN-OV-3.5-I-CTLA4-Fc-Inv

This vector includes the ovalbumin Dnase hypersensitive sites (DHS) I, II and III, the first exon (exon L), the first intron and the CTLA4-Fc fusion protein coding sequence inserted in frame with the ATG of second exon (exon 1) and with the 3' untranslated region (UTR). The expression cassette is inserted in the inverse orientation into an avian leukosis virus (ALV) vector, which was made self-inactivating (SIN) by deletion of nucleotides 1 to 173 of the ALV LTR sequence shown in SEQ ID NO: 29.

The vector was constructed as follows: pNLB-3.9-OM-CTLA4-Fc, disclosed in Example 20 of US patent publication No. 2007/0113299, published May 17, 2007, the disclosure of which is incorporated in its entirety herein by reference, was cut with Nae I and Not I. The Not I site was filled in by Klenow reaction. The resulting 8125 bp fragment was gel purified, religated, producing pOM-3.9-CTLA4-dSacI.

pOM-3.9-CTLA4-dSacI was cut with EcoRI and Kpn I and the 8115 bp fragment gel purified. The 3' UTR of the chicken ovalbumin gene was PCRed from BAC 26, disclosed in US patent publication No. 2006/0130170, published Jun. 15, 2006, with the primers 5'-GCGGAATTCAAAGAA-GAAAGCTGAAAAAC-3' (SEQ ID NO: 13) and 5'-GCGGGTACCTTCAAATACTACAAGTGAAA-3' (SEQ ID NO: 14). The 3' UTR PCR was cut with Eco RI and Kpn I and the 684 bp fragment gel purified. The 8115 bp fragment of pOM-3.9-CTLA4-dSacI was ligated to the 684 bp fragment of 3' UTR PCR, producing pOM-3.9-CTLA4-OV3'UTR.

The 3.5 kb OV promoter region, exon L, first intron and the UTR of exon 1 was PCR amplified with BAC26 as a template and with primers 5'-GGCCTCGAGTCAAGTTCTGAG-TAGGTTTTAGTG-3' (SEQ ID NO: 15) and 5'-GCGCGTCTCTGTCTAGAGCAAACAGCA-GAACAGTGAAAATG-3' (SEQ ID NO: 16). The PCR product was cut with Xho I and Esp3I and the 5094 bp product was gel purified.

Figure 3:
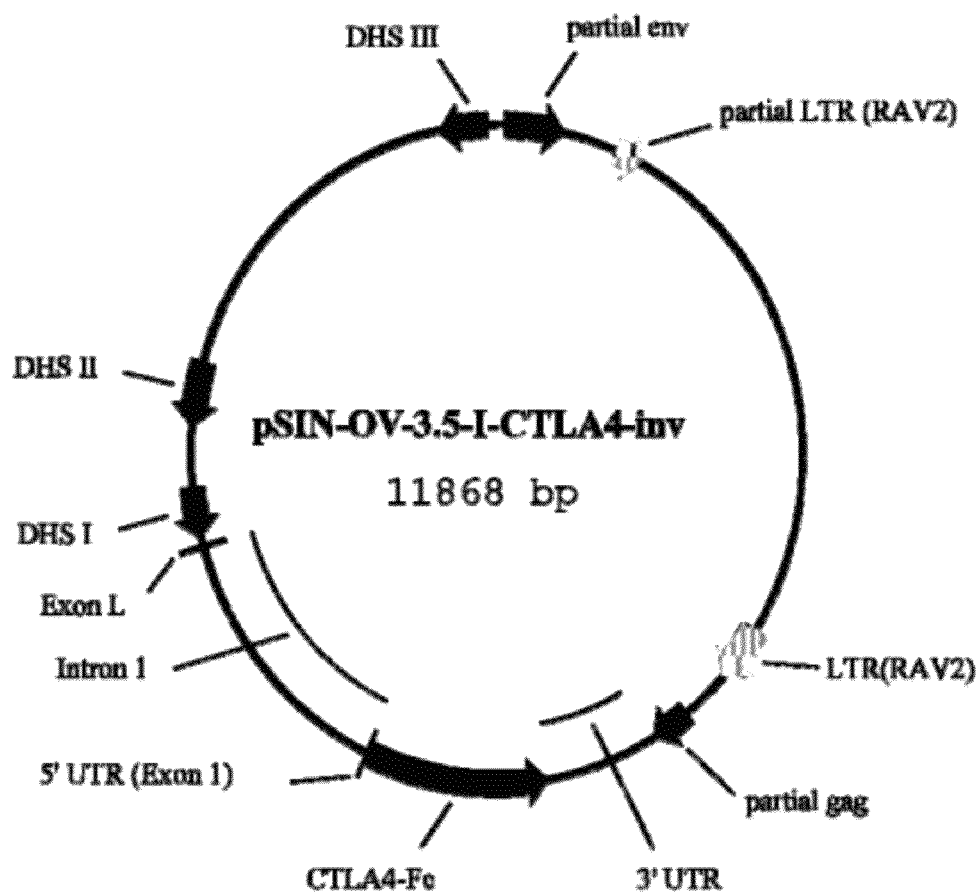
FIG. 3 shows a circular map of the pSIN-OV-3.5-I-CTLA4-inv vector. The nucleotide sequence of pSIN-OV-3.5-I-CTLA4-inv is shown in SEQ ID NO: 19.

A 5' portion of the CTLA4-Fc gene was PCR amplified using pOM-3.9-CTLA4 as a template and primers 5'-GCGCGTCTCAAGACAACTCAGAGTTCAC-CATGGGTGTACTGCTCACACAG-3' (SEQ ID NO: 17) and 5'-GGCCCGGGAGTTTTGTCAGAAGATTTGGG-3' (SEQ ID NO: 18). The PCR product was cut with Esp3I and SacI and the 384 bp product gel purified.

pOM-3.9-CTLA4-OV3'UTR was cut with Sac I and Xho I, the 4473 bp product gel purified and ligated to the 5094 bp OV PCR fragment and 384 bp CTLA4-Fc fragment, producing pOV-3.5-I-CTLA4.

pALV-SIN, disclosed, for example, in Example 10 of parent case US patent publication No. 2007/0124829, published May 31, 2007, was cut with Mfe I and Xho I, filled in with Klenow and the 4911 bp fragment gel purified.

pOV-3.5-I-CTLA4 was cut with XhoI and BamHI, filled in with Klenow and the 6957 bp fragment gel purified. This fragment was ligated into the 4911 bp fragment of pAVI-SIN such that the CTLA4-Fc gene and flanking expression elements are in the opposite orientation of the ALV long terminal repeats, producing pSIN-OV-3.5-I-CTLA4-inv. See FIG. 3 and SEQ ID NO: 19. Such opposite orientation may be preferred if the coding sequence of interest (i.e., CSI) in the transgene contains one or more introns or splice sites.

Example 5

Production of Transgenic Quail Using SIN-OV-3.5-I-CTLA4-inv

Retroviral particles containing the pSIN-OV-3.5-I-CTLA4-inv vector (FIG. 3) and pseudotyped with the VSV envelope protein were produced as described in US patent publication No. 2007/0077650, published Apr. 5, 2007. Virus particles were harvested at 48 hours post-transfection, concentrated and on the same day, approximately 4 microliters of the virus suspension containing about $1 \times 10^5$ particles was injected into the subgerminal cavity of stage X quail eggs. Eggs were resealed and hatched.

ALV has a CTE element in the 3' end of its genome that allows transport of unspliced retroviral RNA to the cytoplasm. In pSIN-OV-3.5-I-CTLA4-inv, due to the inverse orientation of the OV promoter relative to the LTRs, the CTE is upstream of the OV promoter such that the CTE element is only in RNAs derived from the 5' LTR promoter and not in RNAs transcribed by the OV promoter. Therefore, any RNA transcribed by the OV promoter should be spliced prior to being transported into the cytoplasm.

Egg whites from chimeric quail were assayed using an ELISA for CTLA4-Fc. One quail was found to have CTLA4-Fc in her egg white at approximately 16 µg/ml. The transgenesis level in these quail is estimated at about 5% or less. Thus the level in a G1 should be substantially greater. It is expected that similar levels would be seen in a chicken and other avians, as the quail and chicken ovalbumin genes, as well as ovalbumin genes of other avians, are very similar.

Example 6

Construction of pSIN-3.9-OM-CTLA4-Fc

Figure 4:
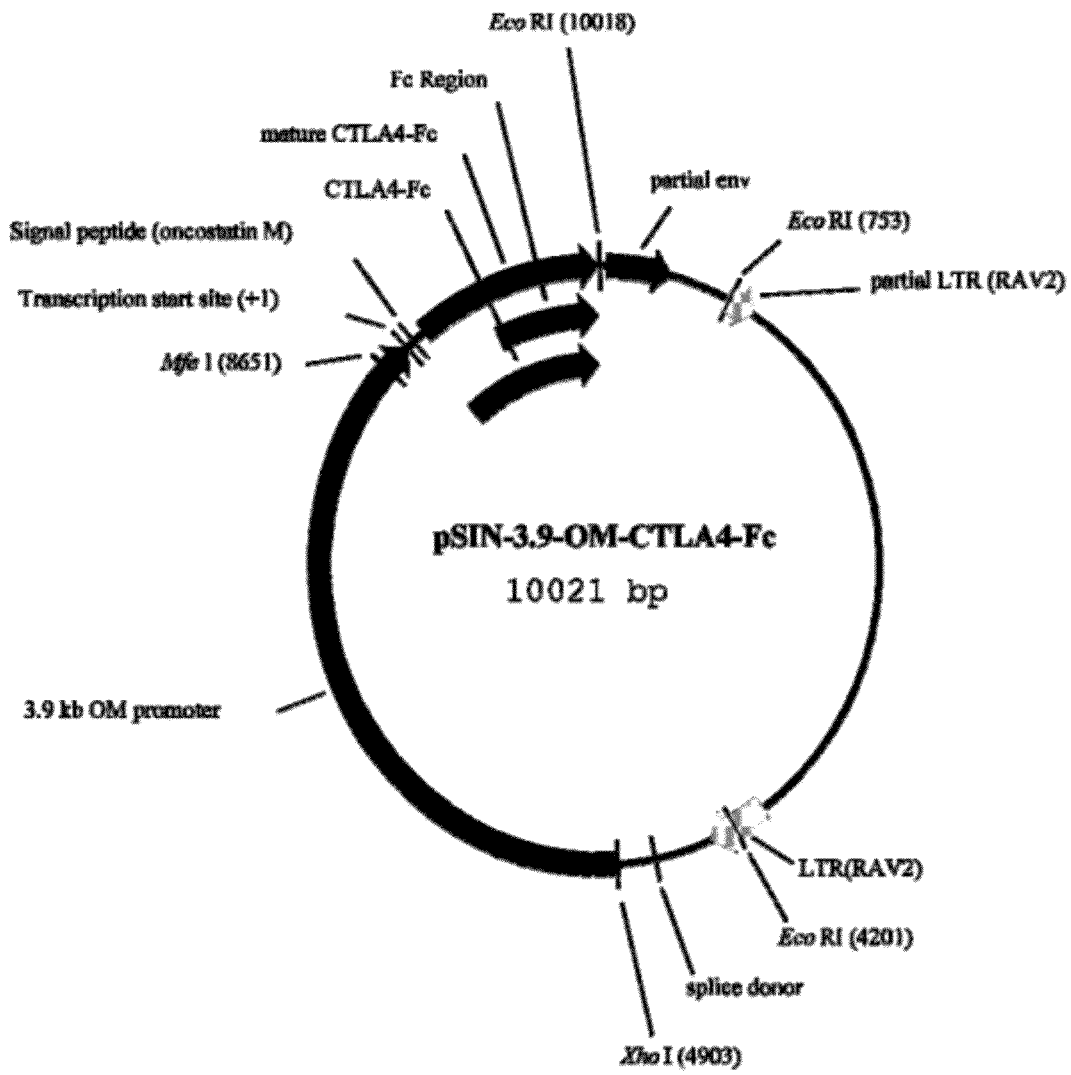
FIG. 4 shows a circular map of the pSIN-3.9-OM-CTLA4-Fc vector. The nucleotide sequence of pSIN-3.9-OM-CTLA4-Fc is shown in SEQ ID NO: 20.

The 4907 bp Mfe I/Xho I fragment of pALV-SIN (disclosed, for example, in US patent publication No. 2007/0124829, published May 31, 2007) was ligated to the 5115 XhoI/EcoRI fragment of pOM-3.9-CTLA4 (shown in FIG. 15 of US patent publication No. 2007/0113299, published May 17, 2007), producing pSIN-3.9-OM-CTLA4-Fc shown in FIG. 4 and SEQ ID NO: 20.

Example 7

Production of Transgenic Chickens Using pSIN-3.9-OM-CTLA4-Fc

Retroviral particles pseudotyped with the VSV envelope protein and containing the pSIN-3.9-OM-CTLA4-Fc (FIG. 4) vector were produced as described in US patent publication No. 2007/0077650, published Apr. 5, 2007. Virus was harvested at 48 hours post-transfection, concentrated and on the same day approximately 7 microliters injected into the subgerminal cavity of stage X eggs. Eggs were resealed and incubated until hatch.

Egg white from hens was assayed using an ELISA for CTLA4-Fc. One hen was found to have CTLA4-Fc in her egg white at approximately 0.37 µg/ml. The transgenesis level in these hens is estimated at 5% or less. Thus the levels in a G1 should be substantially greater.

Any useful coding sequence may be inserted in place of the CTLA4-Fc coding sequence for production of the corresponding product.

Example 8

Construction of pSIN-1.8-OM-IFNa-2B

Figure 5:
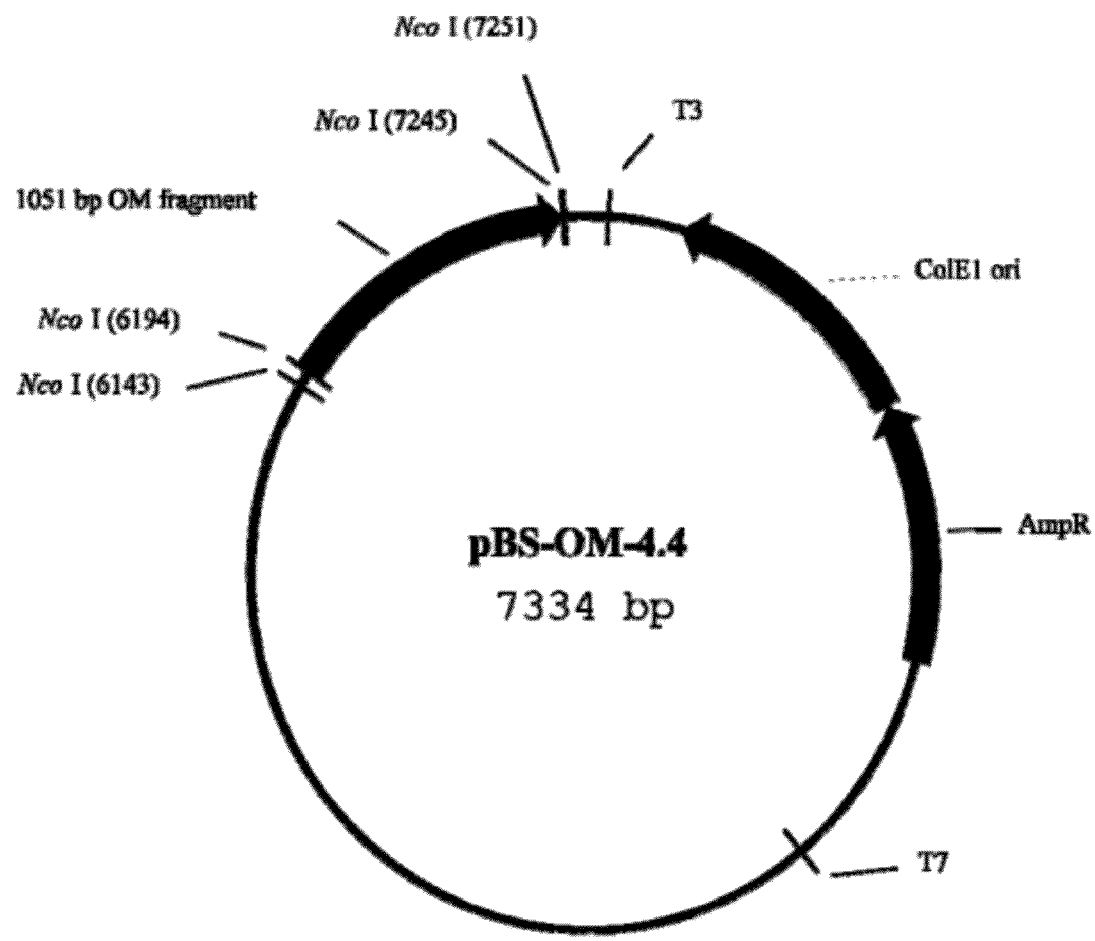
FIG. 5 shows a circular map of the pBS-OM-4.4 vector. The nucleotide sequence of pBS-OM-4.4 is shown in SEQ ID NO: 23.
Figure 6:
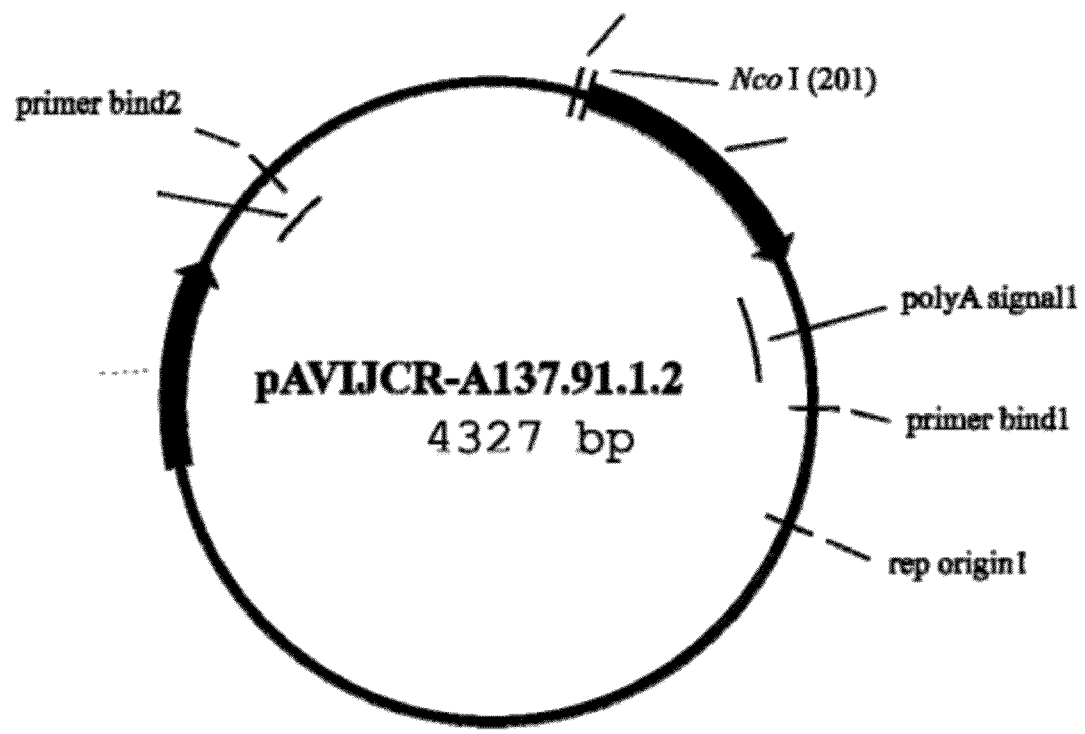
FIG. 6 shows a circular map of the pAVIJCR-A137.91.1.2 vector. The nucleotide sequence of pAVIJCR-A137.91.1.2 is shown in SEQ ID NO: 24.

The 1051 bp Nco I-Nco I fragment from pBS-OM-4.4 (FIG. 5 SEQ ID NO: 23) was inserted into the Nco I site of pAVIJCR-A137.91.1.2 (FIG. 6 SEQ ID NO: 24), thereby inserting the 1 kb ovomucoid promoter in front of an IFN coding sequence and SV40 polyadenylation signal and producing plkb-OM-IFNMM. A 1816 bp Cla I-Sac I fragment of plkb-OM-IFNMM was inserted into the 6245 bp Cla I-Sac I fragment of pBS-OM-4.4, thereby fusing the 4.4 kb ovomucoid fragment with the IFN coding sequence and producing p4.4OM-IFNMM. The 8511 bp BamH I-Sal I fragment of pBS-OMUP-10 was ligated to the 5148 bp BamH I-Sal I fragment of p4.4OM-IFN, thereby placing the 10 kb ovomucoid promoter in front of the IFN coding sequence, producing p10-OM-IFN.

Figure 7:
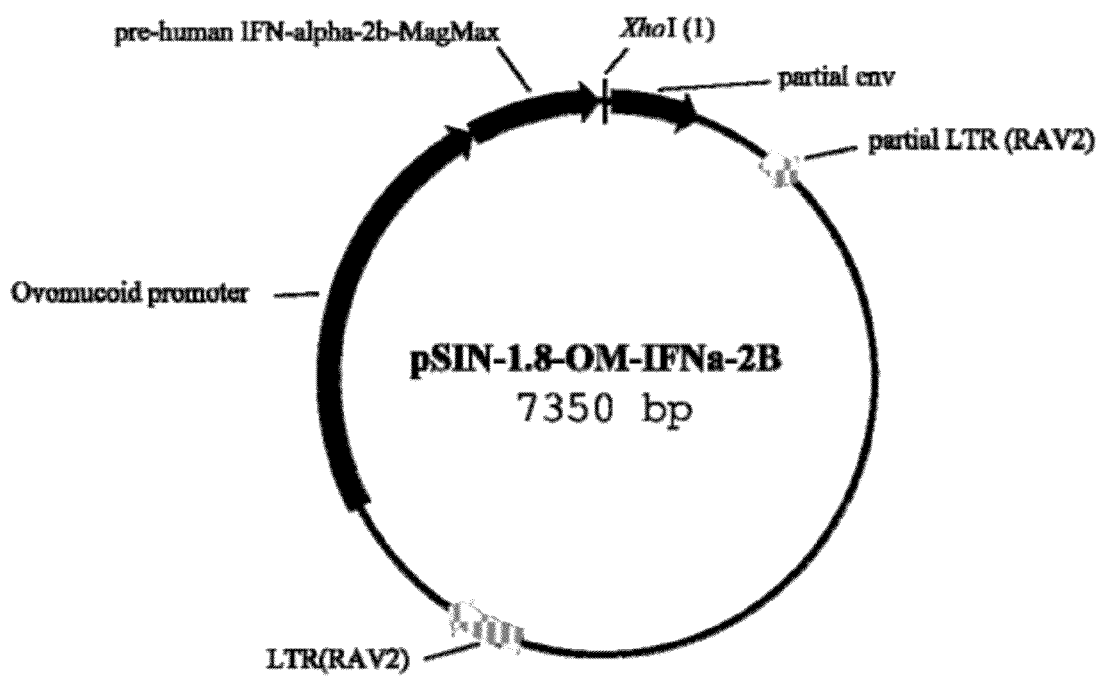
FIG. 7 shows a circular map of the pSIN-1.8-OM-IFNa-2B plasmid vector. The nucleotide sequence of pSIN-1.8-OM-IFNa-2B is shown in SEQ ID NO: 21.

Region 2487-4889 of p10.0-OM-IFN was PCR amplified with primers 5'-GGCGTCGACGGATCCGTTAACCCTA-GAACTAGTGGATCTCTGCCCTTGTGC TGAC-3' (SEQ ID NO: 27) and 5'-GGCCTCGAGCCTAGACTTTTTACTC-CTTAGA-3' (SEQ ID NO: 28). The PCR product was digested with Sal I and Xho I and the 2435 bp isolated. pALV-SIN (disclosed, for example, in US patent publication No. 2007/0124829, published May 31, 2007) was digested with Xho I and the 4915 bp fragment isolated and ligated to the 2435 bp fragment, producing pSIN-1.8-OM-IFNa-2B, shown in FIG. 7 and SEQ ID NO: 21.

Example 9

Production of Transgenic Chickens Using pSIN-1.8-OM-IFNa-2B

Retroviral particles having the pSIN-1.8-OM-IFNa-2B transgene and pseudotyped with the VSV envelope protein were produced as described in US patent publication No. 2007/0077650, published Apr. 5, 2007. Virus was harvested at 48 hours post-transfection, concentrated and, on the same day, approximately 7 microliters injected into the subgerminal cavity of stage X eggs. Eggs were resealed and incubated until hatch.

Egg whites from hens were assayed using an ELISA for IFNa-2B. Hens were found to have IFNa-2B in egg white at levels that ranged from 1.5 to 865.0 ng/ml with IFNa-2B levels at least about 600 fold lower in the serum. The transgenesis level in these hens is estimated at 5% or less.

Five G0 sperm positive roosters were bred to non-transgenic hens. Of 1251 offspring, 30 carried the pSIN-1.8-OM-IFNa-2B transgene. Six of the 30 hens expressed human IFN-α-2B at 34.1 to 165.6 µg/ml of egg white. Each of the six hens had a single copy of the transgene. Serum levels of human IFN-a-2B were 0.3 to 9.2 ng/ml which, on average, was 30,000 fold lower than egg white levels.

Example 10

Production of Transgenic Chickens Using Lentivirus Vectors and Moloney Murine Leukemia Virus The invention specifically contemplates the employment of other retroviral vectors that are useful in avian transgenesis to be used in accordance with the present invention. Such vectors can be employed to produce transgenic avians, for example, in the same way as ALV-SIN vectors have been used in Examples 1 to 9 above. For example, Moloney Murine Leukemia Virus (MMLV) and Lentiviral Vectors can be used in accordance with the invention, each, for example, by deleting one or more of the CAAT box; the TAATA box; and enhancer contained in the U3 region of the upstream LTR of each virus to produce a SIN vector. Alternatively, or in addition (i.e., in conjunction with a SIN vector) no transcriptionally active markers or selectable cassettes are included in each of the retroviral vectors.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. An isolated nucleic acid molecule at least 95% identical to a nucleic acid molecule comprising:
 a 5' LTR as set forth in SEQ ID NO:29;
 an ovalbumin promoter fragment comprising DHS I & II as set forth in the nucleotide sequence 5209 through 8311 of SEQ ID NO:22;
 reverse responsive element as set forth in SEQ ID NO:25;
 constitutive transport element as set forth in SEQ ID NO:26
 a 3' UTR as set forth in the nucleotide sequence 13576 through 15163 of SEQ ID NO:22.

2. An isolated vector comprising the nucleic acid molecule of claim 1.

3. The vector of claim 2, wherein the vector is a self-inactivating vector derived from a retrovirus.

4. The vector of claim 3, wherein the retrovirus is selected from the group consisting of an avian leukosis virus (ALV), a murine leukemia virus (MLV), a moloney murine leukemia virus (MMLV) and a lentivirus.

5. The vector of claim 4, wherein the retrovirus is an avian leukosis virus.

6. The vector of claim 5, wherein the self-inactivation vector has no selectable marker.

7. An isolated host cell containing the vector of claim 2.

* * * * *

UNITED STATES PATENT AND TRADEMARK OFFICE
CERTIFICATE OF CORRECTION

| | | |
|---|---|---|
| PATENT NO. | : 8,383,399 B2 | Page 1 of 1 |
| APPLICATION NO. | : 13/179281 | |
| DATED | : February 26, 2013 | |
| INVENTOR(S) | : Alex J. Harvey and Jeffrey C. Rapp | |

It is certified that error appears in the above-identified patent and that said Letters Patent is hereby corrected as shown below:

In the Claims

In Col. 97, Line 33, in Claim 1, insert -- a -- in the beginning of the line, before "reverse".

In Col. 97, Line 34, in Claim 1, insert -- a -- in the beginning of the line, before "constitutive".

In Col. 97, Line 35, in Claim 1, insert -- ; and -- at the end of the line, after "NO:26".

Signed and Sealed this
Seventeenth Day of March, 2015

Michelle K. Lee
*Director of the United States Patent and Trademark Office*

SEQUENCE LISTING

<160> NUMBER OF SEQ ID NOS: 29

<210> SEQ ID NO 1
<211> LENGTH: 9597
<212> TYPE: DNA
<213> ORGANISM: Artificial Sequence
<220> FEATURE:
<223> OTHER INFORMATION: pALV-SIN-4.2-Lys-IFNa-2B Vector

<400> SEQUENCE: 1

```
gatcccccgt gctgcagaac cgagcggcta ttgacttctt gctcctagct cacggccatg     60
gctgtgagga cattgcggga atgtgttgtt tcaatctgag tgatcacagt gagtctatac    120
agaagaagtt ccagctaatg aaggaacatg tcaataagat cggcgtgaac aacgacccaa    180
tcggaagttg gctgcgagga ttattcggag gaataggaga atgggccgta cacttgctga    240
aaggactgct tttggggctt gtagttatct tgttgctagt agtatgcttg ccttgccttt    300
tgcaatgtgt atctagtagt attcgaaaga tgattgataa ttcactcggc tatcgcgagg    360
aatataaaaa aattacagga ggcttataag cagcccgaaa gaagagcgta ggcgagttct    420
tgtattccgt gtgatagctg gttggattgg taattgatcg gctggcacgc ggaatatagg    480
aggtcgctga atagtaaact tgtagacttg gctacagcat agagtatctt ctgtagctct    540
gatgactgct aggaaataat gctacggata atgtggggag ggcaaggctt gcgaatcggg    600
ttgtaacggg caaggcttga ctgaggggac aatagcatgt ttaggcgaaa agcgggctt    660 cggttgtacg cggttaggag tcccctcagg atatagtagt ttcgcttttg cataggagg    720 gggacggatt ggacgaacca ctgaattccg cattgcagag atattgtatt taagtgccta    780
gctcgataca ataaacgcca tttgaccatt caccacattg gtgtgcacct gggttgatgg    840
ccggaccgtt gattccctgr cgactacgag cacatgcatg aagcagaagg cttcatttgg    900
tgaccccgac gtgatcgtta gggaatacgc gctcactggc cgtcgtttta caacgtcgtg    960
actgggaaaa ccctggcgtt acccaactta atcgccttgc agcacatccc cctttcgcca   1020
gctggcgtaa tagcgaagag gcccgcaccg atcgcccttc ccaacagttg cgcagcctga   1080
atggcgaatg gaaattgtaa gcgttaatat tttgttaaaa ttcgcgttaa atttttgtta   1140
aatcagctca ttttttaacc aataggccga atcggcaaa atcccttata aatcaaaaga   1200
atagaccgag atagggttga gtgttgttcc agtttggaac aagagtccac tattaaagaa   1260
cgtggactcc aacgtcaaag ggcgaaaaac cgtctatcag ggcgatggcc cactacgtga   1320
accatcaccc taatcaagtt ttttggggtc gaggtgccgt aaagcactaa atcggaaccc   1380
taaagggagc ccccgattta gagcttgacg gggaaagccg gcgaacgtgg cgagaaagga   1440
agggaagaaa gcgaaaggag cgggcgctag ggcgctggca agtgtagcgg tcacgctgcg   1500
cgtaaccacc acacccgccg cgcttaatgc gccgctacag ggcgcgtcag gtggcacttt   1560
tcggggaaat gtgcgcggaa cccctatttg tttattttc taaatacatt caaatatgta   1620
tccgctcatg agacaataac cctgataaat gcttcaataa tattgaaaaa ggaagagtat   1680
gagtattcaa catttccgtg tcgcccttat cccttttt gcggcatttt gccttcctgt   1740
ttttgctcac ccagaaacgc tggtgaaagt aaaagatgct gaagatcagt tgggtgcacg   1800
agtgggttac atcgaactgg atctcaacag cggtaagatc cttgagagtt tcgccccga   1860 agaacgtttt ccaatgatga gcacttttaa agttctgcta tgtggcgcgg tattatcccg   1920
tattgacgcc gggcaagagc aactcggtcg ccgcatacac tattctcaga atgacttggt   1980
```

```
tgagtactca ccagtcacag aaaagcatct tacggatggc atgacagtaa gagaattatg    2040
cagtgctgcc ataaccatga gtgataacac tgcggccaac ttacttctga caacgatcgg    2100
aggaccgaag gagctaaccg cttttttgca aacatgggg  gatcatgtaa ctcgccttga    2160
tcgttgggaa ccggagctga atgaagccat accaaacgac gagcgtgaca ccacgatgcc    2220
tgtagcaatg gcaacaacgt tgcgcaaact attaactggc gaactactta ctctagcttc    2280
ccggcaacaa ttaatagact ggatggaggc ggataaagtt gcaggaccac ttctgcgctc    2340
ggcccttccg gctggctggt ttattgctga taaatctgga gccggtgagc gtgggtctcg    2400
cggtatcatt gcagcactgg ggccagatgg taagccctcc cgtatcgtag ttatctacac    2460
gacggggagt caggcaacta tggatgaacg aaatagacag atcgctgaga taggtgcctc    2520
actgattaag cattggtaac tgtcagacca agtttactca tatatacttt agattgattt    2580
aaaacttcat ttttaattta aaaggatcta ggtgaagatc ctttttgata atctcatgac    2640
caaaatccct taacgtgagt tttcgttcca ctgagcgtca gaccccgtag aaaagatcaa    2700
aggatcttct tgagatcctt ttttttctgcg cgtaatctgc tgcttgcaaa caaaaaaacc    2760
accgctacca gcggtggttt gtttgccgga tcaagagcta ccaactcttt ttccgaaggt    2820
aactggcttc agcagagcgc agataccaaa tactgtcctt ctagtgtagc cgtagttagg    2880
ccaccacttc aagaactctg tagcaccgcc tacatacctc gctctgctaa tcctgttacc    2940
agtggctgct gccagtggcg ataagtcgtg tcttaccggg ttggactcaa gacgatagtt    3000
accggataag gcgcagcggt cgggctgaac ggggggttcg tgcacacagc ccagcttgga    3060
gcgaacgacc tacaccgaac tgagatacct acagcgtgag ctatgagaaa gcgccacgct    3120
tcccgaaggg agaaaggcgg acaggtatcc ggtaagcggc agggtcggaa caggagagcg    3180
cacgagggag cttccagggg gaaacgcctg gtatctttat agtcctgtcg ggtttcgcca    3240
cctctgactt gagcgtcgat ttttgtgatg ctcgtcaggg gggcggagcc tatggaaaaa    3300
cgccagcaac gcggcctttt tacggttcct ggccttttgc tggccttttg ctcacatgtt    3360
ctttcctgcg ttatcccctg attctgtgga taaccgtatt accgcctttg agtgagctga    3420
taccgctcgc cgcagccgaa cgaccgagcg cagcgagtca gtgagcgagg aagcggaaga    3480
gcgcccaata cgcaaaccgc ctctccccgc gcgttggccg attcattaat gcagctggca    3540
cgacaggttt cccgactgga aagcgggcag tgagcgcaac gcaattaatg tgagttagct    3600
cactcattag gcaccccagg ctttacactt tatgcttccg gctcgtatgt tgtgtggaat    3660
tgtgagcgga taacaatttc acacaggaaa cagctatgac catgattacg ccaagcgcgc    3720
attggtaatt gatcggctgg cacgcggaat ataggaggtc gctgaatagt aaacttgtag    3780
acttggctac agcatagagt atcttctgta gctctgatga ctgctaggaa ataatgctac    3840
ggataatgtg gggagggcaa ggcttgcgaa tcggttgta  acgggcaagg cttgactgag    3900
gggacaatag catgtttagg cgaaaagcgg ggcttcggtt gtacgcggtt aggagtcccc    3960
tcaggatata gtagtttcgc ttttgcatag ggaggggaa  atgtagtctt atgcaatact    4020
cttgtagtct tgcaacatgc ttatgtaacg atgagttagc aacatgcctt ataaggagag    4080
aaaaagcacc gtgcatgccg attggtggga gtaaggtggt atgatcgtgg tatgatcgtg    4140
ccttgttagg aaggcaacag acgggtctaa cacggattgg acgaaccact gaattccgca    4200
ttgcagagat attgtattta agtgcctagc tcgatacaat aaacgccatt tgaccattca    4260
ccacattggt gtgcacctgg gttgatggcc ggaccgttga ttccctgrcg actacgagca    4320
catgcatgaa gcagaaggct tcatttggtg accccgacgt gatcgttagg gaatagtggt    4380
```

```
cggccacagg cggcgtggcg atcctgtcct catccgtctc gcttattcgg ggagcggacg    4440
atgaccctag tagaggggc tgcggcttag gagggcagaa gctgagtggc gtcggaggga    4500
gccctactgc aggggggccaa catacccctac cgagaactca gagagtcgtt ggaagacggg   4560
aaggaagccc gacgactgag cggtccaccc caggcgtgat tccggttgct ctgcgtgatt    4620
ccggtcgccc ggtggatcaa gcatggaagc cgtcataaag gtgatttcgt ccgcgtgtaa    4680
gacctattgc gggaaaacct ctccttctaa aaggaaata ggggctatgt tgtccctgtt    4740
acaaaaggaa gggttgctta cgtcccctc agacttatat tccccggggt cctgggatcc    4800
gataccgtcc ctattttgt gtttgcttca gcagccattt aattcttcag tgtcatcttg    4860
ttctgttgat gccactggaa caggattttc agcagtcttg caaagaacat ctagctgaaa    4920
actttctgcc attcaatatt cttaccagtt cttcttgttt gaggtgagcc ataaattact    4980
agaacttcgt cactgacaag tttatgcatt ttattacttc tattatgtac ttactttgac    5040
ataacacaga cacgcacata ttttgctggg atttccacag tgtctctgtg tccttcacat    5100
ggttttactg tcatacttcc gttataacct tggcaatctg cccagctgcc catcacaaga    5160
aaagagattc cttttttatt acttctcttc agccaataaa caaatgtga gaagcccaaa    5220 caagaacttg tggggcaggc tgccatcaag ggagagacag ctgaagggtt gtgtagctca    5280
atagaattaa gaaataataa agctgtgtca gacagttttg cctgatttat acaggcacgc    5340
cccaagccag agaggctgtc tgccaaggcc accttgcagt cttggttttg taagataagt    5400
cataggtaac ttttctggtg aattgcgtgg agaatcatga tggcagttct tgctgtttac    5460
tatggtaaga tgctaaaata ggagacagca aagtaacact tgctgctgta ggtgctctgc    5520
tatccagaca gcgatggcac tcgcacacca agatgaggga tgctcccagc tgacggatgc    5580
tggggcagta acagtgggtc ccatgctgcc tgctcattag catcacctca gccctcacca    5640
gcccatcaga aggatcatcc caagctgagg aaagttgctc atcttcttca catcatcaaa    5700
cctttggcct gactgatgcc tcccggatgc ttaaatgtgg tcactgacat ctttattttt    5760
ctatgatttc aagtcagaac ctccggatca ggagggaaca catagtggga atgtaccctc    5820
agctccaagg ccagatcttc cttcaatgat catgcatgct acttaggaag gtgtgtgtgt    5880
gtgaatgtag aattgccttt gttatttttt cttcctgctg tcaggaacat tttgaatacc    5940
agagaaaaag aaaagtgctc ttcttggcat gggaggagtt gtcacacttg caaaataaag    6000
gatgcagtcc caaatgttca taatctcagg gtctgaagga ggatcagaaa ctgtgtatac    6060
aatttcaggc ttctctgaat gcagcttttg aaagctgttc ctggccgagg cagtactagt    6120
cagaaccctc ggaaacagga acaaatgtct tcaaggtgca gcaggaggaa acaccttgcc    6180
catcatgaaa gtgaataacc actgccgctg aaggaatcca gctcctgttt gagcaggtgc    6240
tgcacactcc cacactgaaa caacagttca ttttttatagg acttccagga aggatcttct    6300
tcttaagctt cttaattatg gtacatctcc agttggcaga tgactatgac tactgacagg    6360
agaatgagga actagctggg aatatttctg tttgaccacc atggagtcac ccatttcttt    6420
actggtattt ggaaataata attctgaatt gcaaagcagg agttagcgaa gatcttcatt    6480
tcttccatgt tggtgacagc acagttctgg ctatgaaagt ctgcttacaa ggaagaggat    6540
aaaaatcata gggataataa atctaagttt gaagacaatg aggttttagc tgcatttgac    6600
atgaagaaat tgagacctct actggatagc tatggtattt acgtgtcttt ttgcttagtt    6660
acttattgac cccagctgag gtcaagtatg aactcaggtc tctcgggcta ctggcatgga    6720
ttgattacat acaactgtaa ttttagcagt gatttagggt ttatgagtac ttttgcagta    6780
```

```
aatcataggg ttagtaatgt taatctcagg gaaaaaaaaa aaaagccaac cctgacagac   6840
atcccagctc aggtggaaat caaggatcac agctcagtgc ggtcccagag aacacaggga   6900
ctcttctctt aggaccttta tgtacagggc ctcaagataa ctgatgttag tcagaagact   6960
ttccattctg gccacagttc agctgaggca atcctggaat tttctctccg ctgcacagtt   7020
ccagtcatcc cagtttgtac agttctggca cttttgggt caggccgtga tccaaggagc   7080
agaagttcca gctatggtca gggagtgcct gaccgtccca actcactgca ctcaaacaaa   7140
ggcgaaacca caagagtggc ttttgttgaa attgcagtgt ggcccagagg ggctgcacca   7200
gtactggatt gaccacgagg caacattaat cctcagcaag tgcaatttgc agccattaaa   7260
ttgaactaac tgatactaca atgcaatcag tatcaacaag tggtttggct tggaagatgg   7320
agtctagggg ctctcagga gtagctactc tctaatggag ttgcattttg aagcaggaca   7380
ctgtgaaaag ctggcctcct aaagaggctg ctaaacatta gggtcaattt tccagtgcac   7440
tttctgaagt gtctgcagtt ccccatgcaa agctgcccaa acatagcact tccaattgaa   7500
tacaattata tgcaggcgta ctgcttcttg ccagcactgt ccttctcaaa tgaactcaac   7560
aaacaatttc aaagtctagt agaaagtaac aagctttgaa tgtcattaaa aagtatatct   7620
gctttcagta gttcagctta tttatgccca ctagaaacat cttgtacaag ctgaacactg   7680
gggctccaga ttagtggtaa aacctacttt atacaatcat agaatcatag aatggcctgg   7740
gttggaaggg accccaagga tcatgaagat ccaacacccc cgccacaggc agggccacca   7800
acctccagat ctggtactag accaggcagc ccagggctcc atccaacctg gccatgaaca   7860
cctccaggga tggagcatcc acaacctctc tgggcagcct gtgccagcac ctcaccaccc   7920
tctctgtgaa gaacttttcc ctgacatcca atctaagcct tccctccttg aggttagatc   7980 cactcccct tgtgctatca ctgtctactc ttgtaaaaag ttgattctcc tccttttgg   8040 aaggttgcaa tgaggtctcc ttgcagcctt cttctcttct gcaggatgaa caagcccagc   8100
tccctcagcc tgtctttata ggagaggtgc tccagccctc tgatcatctt tgtggccctc   8160
ctctggaccc gctccaagag ctccacatct ttcctgtact gggggcccca ggcctgaatg   8220
cagtactcca gatggggcct caaaagagca gagtaaagag ggacaatcac cttcctcacc   8280
ctgctggcca gccctcttct gatggagccc tggatacaac tggctttctg agctgcaact   8340
tctccttatc agttccacta ttaaaacagg aacaatacaa caggtgctga tggccagtgc   8400
agagtttttc acacttcttc atttcggtag atcttagatg aggaacgttg aagttgtgct   8460
tctgcgtgtg cttcttcctc ctcaaatact cctgcctgat acctcacccc acctgccact   8520
gaatggctcc atggcccct gcagccaggg ccctgatgaa cccggcactg cttcagatgc   8580
tgtttaatag cacagtatga ccaagttgca cctatgaata cacaaacaat gtgttgcatc   8640
cttcagcact tgagaagaag agccaaattt gcattgtcag gaaatggttt agtaattctg   8700
ccaattaaaa cttgtttatc taccatggct gtttttatgg ctgttagtag tggtacactg   8760
atgatgaaca atggctatgc agtaaaatca agactgtaga tattgcaaca gactataaaa   8820
ttcctctgtg gcttagccaa tgtggtactt cccacattgt ataagaaatt tggcaagttt   8880
agagcaatgt ttgaagtgtt gggaaatttc tgtatactca agagggcgtt tttgacaact   8940
gtagaacaga ggaatcaaaa gggggtggga ggaagttaaa agaagaggca ggtgcaagag   9000
agcttgcagt cccgctgtgt gtacgacact ggcaacatga ggtctttgct aatcttggtg   9060
ctttgcttcc tgccctggc tgccttaggg tgcgatctgc ctcagaccca cagcctgggc   9120
agcaggagga ccctgatgct gctggctcag atgaggagaa tcagcctgtt tagctgcctg   9180
```

-continued

```
aaggataggc acgatttggg cttccctcaa gaggagtttg gcaaccagtt tcagaaggct    9240
gagaccatcc ctgtgctgca cgagatgatc cagcagatct ttaacctgtt tagcaccaag    9300
gatagcagcg ctgcttggga tgagaccctg ctggataagt tttacaccga gctgtaccag    9360
cagctgaacg atctggaggc ttgcgtgatc cagggcgtgg gcgtgaccga gacccctctg    9420
atgaaggagg atagcatcct ggctgtgagg aagtactttc agaggatcac cctgtacctg    9480
aaggagaaga agtacagccc ctgcgcttgg gaagtcgtga gggctgagat catgaggagc    9540
tttagcctga gcaccaacct gcaagagagc ttgaggtcta aggagtaaaa agtctag       9597
```

```
<210> SEQ ID NO 2
<211> LENGTH: 28
<212> TYPE: DNA
<213> ORGANISM: Artificial Sequence
<220> FEATURE:
<223> OTHER INFORMATION: Primer ALV-SIN-1

<400> SEQUENCE: 2
atgcgcgcat tggtaattga tcggctgg                                        28

<210> SEQ ID NO 3
<211> LENGTH: 80
<212> TYPE: DNA
<213> ORGANISM: Artificial Sequence
<220> FEATURE:
<223> OTHER INFORMATION: Primer ALV-SIN-2

<400> SEQUENCE: 3
atatgcggcc gcggtaccgc ccgggcatcg atatcaagct tacggttcac taaacgagct    60
ctgcttatat agacctccca                                                 80

<210> SEQ ID NO 4
<211> LENGTH: 59
<212> TYPE: DNA
<213> ORGANISM: Artificial Sequence
<220> FEATURE:
<223> OTHER INFORMATION: Primer ALV-SIN-3

<400> SEQUENCE: 4
atatgcggcc gcgtcgacgg ccggccagat ctgctgagcc ggtcgctacc attaccagt     59

<210> SEQ ID NO 5
<211> LENGTH: 28
<212> TYPE: DNA
<213> ORGANISM: Artificial Sequence
<220> FEATURE:
<223> OTHER INFORMATION: Primer ALV-SIN-4

<400> SEQUENCE: 5
atacgcgtat tccctaacga tcacgtcg                                        28

<210> SEQ ID NO 6
<211> LENGTH: 21
<212> TYPE: DNA
<213> ORGANISM: Artificial Sequence
<220> FEATURE:
<223> OTHER INFORMATION: Primer ALV-SIN-5

<400> SEQUENCE: 6
ctgaagtgta aggaatgtaa g                                               21

<210> SEQ ID NO 7
<211> LENGTH: 30
<212> TYPE: DNA
```

-continued

```
<213> ORGANISM: Artificial Sequence
<220> FEATURE:
<223> OTHER INFORMATION: Primer ALV-SIN-6

<400> SEQUENCE: 7
gcgcgtctca tccccctccc tatgcaaaag                                      30

<210> SEQ ID NO 8
<211> LENGTH: 37
<212> TYPE: DNA
<213> ORGANISM: Artificial Sequence
<220> FEATURE:
<223> OTHER INFORMATION: Primer ALV-SIN-7

<400> SEQUENCE: 8
gggcgtctca gggacggatt ggacgaacca ctgaatt                              37

<210> SEQ ID NO 9
<211> LENGTH: 20
<212> TYPE: DNA
<213> ORGANISM: Artificial Sequence
<220> FEATURE:
<223> OTHER INFORMATION: Primer ALV-SIN-8

<400> SEQUENCE: 9
ttagtgcttt acggcacctc                                                 20

<210> SEQ ID NO 10
<211> LENGTH: 38
<212> TYPE: DNA
<213> ORGANISM: Artificial Sequence
<220> FEATURE:
<223> OTHER INFORMATION: Primer ALV-SIN-9

<400> SEQUENCE: 10
gacggatccg ataccgtccc tattttttgtg tttgcttc                            38

<210> SEQ ID NO 11
<211> LENGTH: 30
<212> TYPE: DNA
<213> ORGANISM: Artificial Sequence
<220> FEATURE:
<223> OTHER INFORMATION: Primer ALV-SIN-10

<400> SEQUENCE: 11
taacggatcc tagactttttt actccttaga                                     30

<210> SEQ ID NO 12
<211> LENGTH: 11945
<212> TYPE: DNA
<213> ORGANISM: Artificial Sequence
<220> FEATURE:
<223> OTHER INFORMATION: Proximal promoter and lysozyme signal peptide

<400> SEQUENCE: 12
tgccgccttc tttgatattc actctgttgt atttcatctc ttcttgccga tgaaaggata     60
taacagtctg tataacagtc tgtgaggaaa tacttggtat ttcttctgat cagtgttttt    120
ataagtaatg ttgaatattg gataaggctg tgtgtccttt gtcttgggag acaaagccca    180
cagcaggtgg tggttggggt ggtggcagct cagtgacagg agaggttttt ttgcctgttt    240
tttttttttt tttttttttt aagtaaggtg ttcttttttc ttagtaaatt ttctactgga    300
ctgtatgttt tgacaggtca gaaacatttc ttcaaaagaa gaacctttttg gaaactgtac    360 agcccttttc tttcattccc ttttttgcttt ctgtgccaat gcctttggtt ctgattgcat    420
```

-continued

```
tatggaaaac gttgatcgga acttgaggtt tttatttata gtgtggcttg aaagcttgga      480
tagctgttgt tacacgagat accttattaa gtttaggcca gcttgatgct ttattttttc      540
cctttgaagt agtgagcgtt ctctggtttt tttcctttga aactggtgag cttagatttt      600
ttctaatggg attttttacc tgatgatcta gttgcatacc caaatgcttg taaatgtttt      660
cctagttaac atgttgataa cttcggattt acatgttgta tatacttgtc atctgtgttt      720
ctagtaaaaa tatatggcat ttatagaaat acgtaattcc tgatttcctt ttttttttatc     780 tctatgctct gtgtgtacag gtcaaacaga cttcactcct atttttatt atagaatttt      840 atatgcagtc tgtcgttggt tcttgtgttg taaggataca gccttaaatt tcctagagcg      900
atgctcagta aggcgggttg tcacatgggt tcaaatgtaa aacgggcacg tttggctgct      960
gccttcccga gatccaggac actaaactgc ttctgcactg aggtataaat cgcttcagat     1020
cccagggaag tgcagatcca cgtgcatatt cttaaagaag aatgaatact ttctaaaata     1080
ttttggcata ggaagcaagc tgcatggatt tgtttgggac ttaaattatt ttggtaacgg     1140
agtgcatagg ttttaaacac agttgcagca tgctaacgag tcacagcgtt tatgcagaag     1200
tgatgcctgg atgcctgttg cagctgttta cggcactgcc ttgcagtgag cattgcagat     1260
aggggtgggg tgctttgtgt cgtgttccca cacgctgcca cacagccacc tcccggaaca     1320
catctcacct gctgggtact tttcaaacca tcttagcagt agtagatgag ttactatgaa     1380
acagagaagt tcctcagttg gatattctca tgggatgtct ttttttccat gttgggcaaa     1440
gtatgataaa gcatctctat ttgtaaatta tgcacttgtt agttcctgaa tcctttctat     1500
agcaccactt attgcagcag gtgtaggctc tggtgtggcc tgtgtctgtg cttcaatctt     1560
ttaaagcttc tttggaaata cactgacttg attgaagtct cttgaagata gtaaacagta     1620
cttacctttg atcccaatga aatcgagcat ttcagttgta aaagaattcc gcctattcat     1680
accatgtaat gtaattttac accccccagtg ctgacacttt ggaatatatt caagtaatag     1740
actttggcct caccctcttg tgtactgtat tttgtaatag aaaatatttt aaactgtgca     1800
tatgattatt acattatgaa agagacattc tgctgatctt caaatgtaag aaaatgagga     1860
gtgcgtgtgc ttttataaat acaagtgatt gcaaattagt gcaggtgtcc ttaaaaaaaa     1920
aaaaaaaaag taatataaaa aggaccaggt gttttacaag tgaaatacat tcctatttgg     1980
taaacagtta cattttatg aagattacca gcgctgctga ctttctaaac ataaggctgt      2040
attgtcttcc tgtaccattg catttcctca ttcccaattt gcacaaggat gtctgggtaa     2100
actattcaag aaatggcttt gaaatacagc atgggagctt gtctgagttg gaatgcagag     2160
ttgcactgca aaatgtcagg aaatggatgt ctctcagaat gcccaactcc aaaggatttt     2220
atatgtgtat atagtaagca gtttcctgat tccagcaggc caaagagtct gctgaatgtt     2280
gtgttgccgg agacctgtat ttctcaacaa ggtaagatgg tatcctagca actgcggatt     2340
ttaatacatt ttcagcagaa gtacttagtt aatctctacc tttagggatc gtttcatcat     2400
ttttagatgt tatacttgaa atactgcata acttttagct ttcatgggtt cctttttttc     2460
agcctttagg agactgttaa gcaatttgct gtccaacttt tgtgttggtc ttaaaactgca     2520 atagtagttt accttgtatt gaagaaataa agaccatttt tatattaaaa aatacttttg     2580
tctgtcttca ttttgacttg tctgatatcc ttgcagtgcc cattatgtca gttctgtcag     2640
atattcagac atcaaaactt aacgtgagct cagtggagtt acagctgcgg ttttgatgct     2700
gttattattt ctgaaactag aaatgatgtt gtcttcatct gctcatcaaa cacttcatgc     2760
agagtgtaag gctagtgaga aatgcataca tttattgata ctttttttaaa gtcaacttt     2820
```

-continued

```
tatcagattt ttttttcatt tggaaatata ttgttttcta gactgcatag cttctgaatc    2880
tgaaatgcag tctgattggc atgaagaagc acagcactct tcatcttact taaacttcat    2940
tttggaatga aggaagttaa gcaagggcac aggtccatga aatagagaca gtgcgctcag    3000
gagaaagtga acctggattt cttggctag tgttctaaat ctgtagtgag aaagtaaca     3060
cccgattcct tgaaagggct ccagctttaa tgcttccaaa ttgaaggtgg caggcaactt    3120
ggccactggt tatttactgc attatgtctc agtttcgcag ctaacctggc ttctccacta    3180
ttgagcatgg actatagcct ggcttcagag gccaggtgaa ggttgggatg ggtggaagga    3240
gtgctgggct gtggctgggg ggactgtggg gactccaagc tgagcttggg gtgggcagca    3300
cagggaaaag tgtgggtaac tatttttaag tactgtgttg caaacgtctc atctgcaaat    3360
acgtaggtg tgtactctcg aagattaaca gtgtgggttc agtaatatat ggatgaattc     3420
acagtggaag cattcaaggg tagatcatct aacgacacca gatcatcaag ctatgattgg    3480
aagcggtatc agaagagcga ggaaggtaag cagtcttcat atgttttccc tccacgtaaa    3540
gcagtctggg aaagtagcac cccttgagca gagacaagga ataattcag gagcatgtgc     3600
taggagaact tccttgctga attctacttg caagagcttt gatgcctggc ttctggtgcc    3660
ttctgcagca cctgcaaggc ccagagcctg tggtgagctg gagggaaaga ttctgctcaa    3720
gtccaagctt cagcaggtca ttgtcttttgc ttcttccccc agcactgtgc agcagagtgg   3780
aactgatgtc gaagcctcct gtccactacc tgttgctgca ggcagactgc tctcagaaaa    3840
agagagctaa ctctatgcca tagtctgaag gtaaaatggg ttttaaaaaa gaaaacacaa    3900
aggcaaaacc ggctgcccca tgagaagaaa gcagtggtaa acatggtaga aaaggtgcag    3960
aagcccccag gcagtgtgac aggcccctcc tgccacctag aggcgggaac aagcttccct    4020
gcctagggct ctgcccgcga agtgcgtgtt tctttggtgg gttttgtttg gcgtttggtt    4080
ttgagattta gacacaaggg aagcctgaaa ggaggtgttg ggcactattt tggttttgtaa    4140
agcctgtact tcaaatatat attttgtgag ggagtgtagc gaattggcca atttaaaata    4200
aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgacata cctgtctctt cgtcacttgg    4440
tcagaagaaa cagatgtgat aatccccagc cgccccaagt ttgagaagat ggcagttgct    4500
tcttttccctt tttcctgcta agtaaggatt ttctcctggc tttgacacct cacgaaatag    4560
tcttcctgcc ttacattctg ggcattattt caaatatctt tggagtgcgc tgctctcaag    4620
tttgtgtctt cctactctta gagtgaatgc tcttagagtg aaagagaagg aagagaagat    4680
gttggccgca gttctctgat gaacacacct ctgaataatg gccaaaggtg ggtgggtttc    4740
tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
ttccttcttg gcagtcagtt tatttctgac agacaaacag ccaccccac tgcaggctta     4920
gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
```

| | |
|---|---|
| aagaaactga tggaaataat gcatgaattg tgtggtggac attttttta aatacataaa | 5280 |
| ctacttcaaa tgaggtcgga gaaggtcagt gttttattag cagccataaa accaggtgag | 5340 |
| cgagtaccat ttttctctac aagaaaaacg attctgagct ctgcgtaagt ataagttctc | 5400 |
| catagcggct gaagctcccc cctggctgcc tgccatctca gctggagtgc agtgccattt | 5460 |
| ccttggggtt tctctcacag cagtaatggg acaatacttc acaaaaattc tttctttcc | 5520 |
| tgtcatgtgg gatccctact gtgcctcct ggttttacgt taccccctga ctgttccatt | 5580 |
| cagcggtttg gaaagagaaa aagaatttgg aaataaaaca tgtctacgtt atcacctcct | 5640 |
| ccagcatttt ggtttttaat tatgtcaata actggcttag atttggaaat gagaggggt | 5700 |
| tgggtgtatt accgaggaac aaaggaaggc ttatataaac tcaagtcttt tatttagaga | 5760 |
| actggcaagc tgtcaaaaac aaaaaggcct taccaccaaa ttaagtgaat agccgctata | 5820 |
| gccagcaggg ccagcacgag ggatggtgca ctgctggcac tatgccacgg cctgcttgtg | 5880 |
| actctgagag caactgcttt ggaaatgaca gcacttggtg caatttcctt tgtttcagaa | 5940 |
| tgcgtagagc gtgtgcttgg cgacagtttt tctagttagg ccacttcttt tttccttctc | 6000 |
| tcctcattct cctaagcatg tctccatgct ggtaatccca gtcaagtgaa cgttcaaaca | 6060 |
| atgaatccat cactgtagga ttctcgtggt gatcaaatct ttgtgtgagg tctataaaat | 6120 |
| atggaagctt atttattttt cgttcttcca tatcagtctt ctctatgaca attcacatcc | 6180 |
| accacagcaa attaaaggtg aaggaggctg gtgggatgaa gagggtcttc tagctttacg | 6240 |
| ttcttccttg caaggccaca ggaaaatgct gagagctgta gaatacagcc tggggtaaga | 6300 |
| agttcagtct cctgctggga cagctaaccg catcttataa ccccttctga gactcatctt | 6360 |
| aggaccaaat agggtctatc tgggggtttt gttcctgctg ttcctcctgg aaggctatct | 6420 |
| cactatttca ctgctcccac ggttacaaac caaagataca gcctgaattt tttctaggcc | 6480 |
| acattacata aatttgacct ggtaccaata ttgttctcta tatagttatt tccttcccca | 6540 |
| ctgtgtttaa ccccttaagg cattcagaac aactagaatc atagaatggt ttggattgga | 6600 |
| aggggcctta aacatcatcc atttccaacc ctctgccatg ggctgcttgc cacccactgg | 6660 |
| ctcaggctgc ccagggcccc atccagcctg gccttgagca cctccaggga tggggcaccc | 6720 |
| acagcttctc tgggcagcct gtgccaacac ctcaccactc tctgggtaaa gaattctctt | 6780 |
| ttaacatcta atctaaatct cttctctttt agtttaaagc cattcctctt tttcccgttg | 6840 |
| ctatctgtcc aagaaatgtg tattggtctc cctcctgctt ataagcagga agtactggaa | 6900 |
| ggctgcagtg aggtctcccc acagccttct cttctccagg ctgaacaagc ccagctcctt | 6960 |
| cagcctgtct tcgtaggaga tcatcttagt ggccctcctc tggacccatt ccaacagttc | 7020 |
| cacggctttc ttgtggagcc ccaggtctgg atgcagtact tcagatgggg ccttacaaag | 7080 |
| gcagagcaga tggggacaat cgcttacccc tccctgctgg ctgcccctgt tttgatgcag | 7140 |
| cccagggtac tgttggcctt tcaggctccc agacccttg ctgatttgtg tcaagctttt | 7200 |
| catccaccag aacccacgct tcctggttaa tacttctgcc ctcacttctg taagcttgtt | 7260 |
| tcaggagact tccattcttt aggacagact gtgttacacc tacctgccct attcttgcat | 7320 |
| atatacattt cagttcatgt ttcctgtaac aggacagaat atgtattcct ctaacaaaaa | 7380 |
| tacatgcaga attcctagtg ccatctcagt aggggtttca tggcagtatt agcacatagt | 7440 |
| caatttgctg caagtacctt ccaagctgcg gcctcccata aatcctgtat ttgggatcag | 7500 |
| ttacctttg gggtaagctt ttgtatctgc agagaccctg ggggtctga tgtgcttcag | 7560 |
| ctctgctctg ttctgactgc accattttct agatcaccca gttgttcctg tacaacttcc | 7620 |

-continued

```
ttgtcctcca tcctttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860 gcatttatt acttctatta tgtacttact ttgacataac acagacacgc acatattttg     7920
ctgggatttc cacagtgtct ctgtgtcctt cacatggttt tactgtcata cttccgttat    7980
aaccttggca atctgcccag ctgcccatca caagaaaaga gattccttt ttattacttc     8040 tcttcagcca ataaacaaaa tgtgagaagc ccaaacaaga acttgtgggg caggctgcca    8100
tcaagggaga gacagctgaa gggttgtgta gctcaataga attaagaaat aataaagctg    8160
tgtcagacag ttttgcctga tttatacagg cacgccccaa gccagagagg ctgtctgcca    8220
aggccacctt gcagtccttg gtttgtaaga taagtcatag gtaacttttc tggtgaattg    8280
cgtggagaat catgatggca gttccttgctg tttactatgg taagatgcta aaataggaga   8340
cagcaaagta acacttgctg ctgtaggtgc tctgctatcc agacagcgat ggcactcgca    8400
caccaagatg agggatgctc ccagctgacg gatgctgggg cagtaacagt gggtcccatg    8460
ctgcctgctc attagcatca cctcagccct caccagccca tcagaaggat catcccaagc    8520
tgaggaaagt tgctcatctt cttcacatca tcaaaccttt ggcctgactg atgcctcccg    8580
gatgcttaaa tgtggtcact gacatcttta tttttctatg atttcaagtc agaacctccg    8640
gatcaggagg gaacacatag tgggaatgta ccctcagctc caaggccaga tcttccttca    8700
atgatcatgc atgctactta ggaaggtgtg tgtgtgtgaa tgtagaattg cctttgttat    8760 ttttcttcc tgctgtcagg aacatttttga ataccagaga aaaagaaaag tgctcttctt    8820
ggcatgggag gagttgtcac acttgcaaaa taaaggatgc agtcccaaat gttcataatc    8880
tcagggtctg aaggaggatc agaaactgtg tatacaattt caggcttctc tgaatgcagc    8940
ttttgaaagc tgttcctggc cgaggcagta ctagtcagaa ccctcggaaa caggaacaaa    9000
tgtcttcaag gtgcagcagg aggaaacacc ttgcccatca tgaaagtgaa taaccactgc    9060
cgctgaagga atccagctcc tgtttgagca ggtgctgcac actcccacac tgaaacaaca    9120
gttcattttt ataggacttc caggaaggat cttcttctta agcttcttaa ttatggtaca    9180
tctccagttg gcagatgact atgactactg acaggagaat gaggaactag ctgggaatat    9240
ttctgtttga ccaccatgga gtcacccatt tctttactgg tatttggaaa taataattct    9300
gaattgcaaa gcaggagtta gcgaagatct tcatttcttc catgttggtg acagcacagt    9360
tctggctatg aaagtctgct tacaaggaag aggataaaaa tcatagggat aataaatcta    9420
agtttgaaga caatgaggtt ttagctgcat ttgacatgaa gaaattgaga cctctactgg    9480
atagctatgg tatttacgtg tctttttgct tagttactta ttgaccccag ctgaggtcaa    9540
gtatgaactc aggtctctcg ggctactggc atggattgat tacatacaac tgtaatttta    9600
gcagtgattt agggtttatg agtacttttg cagtaaatca tagggttagt aatgttaatc    9660
tcagggaaaa aaaaaaaag ccaaccctga cagacatccc agctcaggtg gaaatcaagg     9720
atcacagctc agtgcggtcc cagagaacac agggactctt ctcttaggac ctttatgtac    9780
agggcctcaa gataactgat gttagtcaga agactttcca ttctggccac agttcagctg    9840
aggcaatcct ggaattttct ctccgctgca cagttccagt catcccagtt tgtacagttc    9900
tggcactttt tgggtcaggc cgtgatccaa ggagcagaag ttccagctat ggtcagggag    9960
tgcctgaccg tcccaactca ctgcactcaa acaaaggcga aaccacaaga gtggcttttg    10020
```

-continued

```
ttgaaattgc agtgtggccc agaggggctg caccagtact ggattgacca cgaggcaaca    10080
ttaatcctca gcaagtgcaa tttgcagcca ttaaattgaa ctaactgata ctacaatgca    10140
atcagtatca acaagtggtt tggcttggaa gatggagtct aggggctcta caggagtagc    10200
tactctctaa tggagttgca ttttgaagca ggacactgtg aaaagctggc ctcctaaaga    10260
ggctgctaaa cattagggtc aattttccag tgcactttct gaagtgtctg cagttcccca    10320
tgcaaagctg cccaaacata gcacttccaa ttgaatacaa ttatatgcag gcgtactgct    10380
tcttgccagc actgtccttc tcaaatgaac tcaacaaaca atttcaaagt ctagtagaaa    10440
gtaacaagct ttgaatgtca ttaaaaagta tatctgcttt cagtagttca gcttatttat    10500
gcccactaga aacatcttgt acaagctgaa cactggggct ccagattagt ggtaaaacct    10560
actttataca atcatagaat catagaatgg cctgggttgg aagggacccc aaggatcatg    10620
aagatccaac accccgcca caggcagggc caccaacctc cagatctggt actagaccag    10680
gcagcccagg gctccatcca acctggccat gaacacctcc agggatggag catccacaac    10740
ctctctgggc agcctgtgcc agcacctcac caccctctct gtgaagaact tttccctgac    10800
atccaatcta agccttccct ccttgaggtt agatccactc ccccttgtgc tatcactgtc    10860
tactcttgta aaaagttgat tctcctcctt tttggaaggt tgcaatgagg tctccttgca    10920
gccttcttct cttctgcagg atgaacaagc ccagctccct cagcctgtct ttataggaga    10980
ggtgctccag ccctctgatc atctttgtgg ccctcctctg gacccgctcc aagagctcca    11040
catctttcct gtactggggg ccccaggcct gaatgcagta ctccagatgg ggcctcaaaa    11100
gagcagagta aagagggaca atcaccttcc tcaccctgct ggccagccct cttctgatgg    11160
agccctggat acaactggct ttctgagctg caacttctcc ttatcagttc cactattaaa    11220
acaggaacaa tacaacaggt gctgatggcc agtgcagagt ttttcacact tcttcatttc    11280
ggtagatctt agatgaggaa cgttgaagtt gtgcttctgc gtgtgcttct tcctcctcaa    11340
atactcctgc ctgataccte accccacctg ccactgaatg ctccatggc cccctgcagc    11400
cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca agtttagagc aatgtttgaa gtgttgggaa    11760
atttctgtat actcaagagg gcgttttttga caactgtaga acagaggaat caaaaggggg    11820
tgggaggaag ttaaaagaag aggcaggtgc aagagagctt gcagtcccgc tgtgtgtacg    11880
acactggcaa catgaggtct ttgctaatct tggtgctttg cttcctgccc ctggctgcct    11940
taggg                                                               11945
```

<210> SEQ ID NO 13
<211> LENGTH: 29
<212> TYPE: DNA
<213> ORGANISM: Artificial Sequence
<220> FEATURE:
<223> OTHER INFORMATION: BAC 26 Primer-1

<400> SEQUENCE: 13
gcggaattca aagaagaaag ctgaaaaac                                      29

<210> SEQ ID NO 14

```
<211> LENGTH: 29
<212> TYPE: DNA
<213> ORGANISM: Artificial Sequence
<220> FEATURE:
<223> OTHER INFORMATION: BAC 26 Primer-2

<400> SEQUENCE: 14
gcgggtacct tcaaatacta caagtgaaa                                    29

<210> SEQ ID NO 15
<211> LENGTH: 33
<212> TYPE: DNA
<213> ORGANISM: Artificial Sequence
<220> FEATURE:
<223> OTHER INFORMATION: BAC 26-OV Primer 1

<400> SEQUENCE: 15
ggcctcgagt caagttctga gtaggtttta gtg                               33

<210> SEQ ID NO 16
<211> LENGTH: 41
<212> TYPE: DNA
<213> ORGANISM: Artificial Sequence
<220> FEATURE:
<223> OTHER INFORMATION: BAC 26-OV Primer 2

<400> SEQUENCE: 16
gcgcgtctct gtctagagca aacagcagaa cagtgaaaat g                      41

<210> SEQ ID NO 17
<211> LENGTH: 50
<212> TYPE: DNA
<213> ORGANISM: Artificial Sequence
<220> FEATURE:
<223> OTHER INFORMATION: CTLA-4-Fc Primer 1

<400> SEQUENCE: 17
gcgcgtctca agacaactca gagttcacca tgggtgtact gctcacacag             50

<210> SEQ ID NO 18
<211> LENGTH: 29
<212> TYPE: DNA
<213> ORGANISM: Artificial Sequence
<220> FEATURE:
<223> OTHER INFORMATION: CTLA-4-Fc Primer 2

<400> SEQUENCE: 18
ggcccgggag ttttgtcaga agatttggg                                    29

<210> SEQ ID NO 19
<211> LENGTH: 11868
<212> TYPE: DNA
<213> ORGANISM: Artificial Sequence
<220> FEATURE:
<223> OTHER INFORMATION: pSIN-OV-3.5-I-CTLA4-inv Vector

<400> SEQUENCE: 19
aattgctaga ctaggatccc ccgtgctgca gaaccgagcg gctattgact tcttgctcct    60
agctcacggc catggctgtg aggacattgc gggaatgtgt tgtttcaatc tgagtgatca   120
cagtgagtct atacagaaga agttccagct aatgaaggaa catgtcaata agatcggcgt   180
gaacaacgac ccaatcggaa gttggctgcg aggattattc ggaggaatag agaatgggc    240 cgtcacttg ctgaaaggac tgcttttggg gcttgtagtt atcttgttgc tagtagtatg    300
cttgccttgc ctttttgcaat gtgtatctag tagtattcga aagatgattg ataattcact   360
```

```
cggctatcgc gaggaatata aaaaaattac aggaggctta taagcagccc gaaagaagag    420
cgtaggcgag ttcttgtatt ccgtgtgata gctggttgga ttggtaattg atcggctggc    480
acgcggaata taggaggtcg ctgaatagta aacttgtaga cttggctaca gcatagagta    540
tcttctgtag ctctgatgac tgctaggaaa taatgctacg gataatgtgg ggagggcaag    600
gcttgcgaat cgggttgtaa cgggcaaggc ttgactgagg ggacaatagc atgtttaggc    660
gaaaagcggg gcttcggttg tacgcggtta ggagtcccct caggatatag tagtttcgct    720
tttgcatagg gaggggacg gattggacga accactgaat tccgcattgc agagatattg    780
tatttaagtg cctagctcga tacaataaac gccatttgac cattcaccac attggtgtgc    840 acctggggttg atggccggac cgttgattcc ctgrcgacta cgagcacatg catgaagcag    900
aaggcttcat ttggtgaccc cgacgtgatc gttaggaat acgcgctcac tggccgtcgt    960
tttacaacgt cgtgactggg aaaaccctgg cgttacccaa cttaatcgcc ttgcagcaca   1020
tccccctttc gccagctggc gtaatagcga agaggcccgc accgatcgcc ctccccaaca   1080
gttgcgcagc ctgaatggcg aatggaaatt gtaagcgtta atattttgtt aaaattcgcg   1140
ttaaattttt gttaaatcag ctcatttttt aaccaatagg ccgaaatcgg caaaatccct   1200
tataaatcaa agaatagac cgagatagg ttgagtgttg ttccagtttg gaacaagagt    1260
ccactattaa agaacgtgga ctccaacgtc aaaggcgaa aaaccgtcta tcagggcgat   1320
ggcccactac gtgaaccatc accctaatca agttttttgg ggtcgaggtg ccgtaaagca   1380
ctaaatcgga accctaaagg gagccccga tttagagctt gacggggaaa gccggcgaac    1440
gtggcgagaa aggaagggaa gaaagcgaaa ggagcgggcg ctagggcgct ggcaagtgta   1500
gcggtcacgc tgcgcgtaac caccacaccc gccgcgctta atgcgccgct acagggcgcg   1560
tcaggtggca cttttcgggg aaatgtgcgc ggaacccta tttgtttatt tttctaaata    1620
cattcaaata tgtatccgct catgagacaa taaccctgat aaatgcttca ataatattga   1680
aaaaggaaga gtatgagtat tcaacatttc cgtgtcgccc ttattccctt ttttgcggca   1740
ttttgccttc ctgttttgc tcacccagaa acgctggtga agtaaaaga tgctgaagat   1800 cagttgggtg cacgagtggg ttacatcgaa ctggatctca acagcggtaa gatccttgag   1860
agttttcgcc ccgaagaacg ttttccaatg atgagcactt ttaaagttct gctatgtggc   1920
gcggtattat cccgtattga cgccgggcaa gagcaactcg gtcgccgcat acactattct   1980
cagaatgact tggttgagta ctcaccagtc acagaaaagc atcttacgga tggcatgaca   2040
gtaagagaat tatgcagtgc tgccataacc atgagtgata acactgcggc caacttactt   2100
ctgacaacga tcggaggacc gaaggagcta accgcttttt tgcacaacat ggggggatcat   2160 gtaactcgcc ttgatcgttg ggaaccggag ctgaatgaag ccataccaaa cgacgagcgt   2220
gacaccacga tgcctgtagc aatggcaaca acgttgcgca aactattaac tggcgaacta   2280
cttactctag cttcccggca acaattaata gactggatgg aggcggataa agttgcagga   2340
ccacttctgc gctcggccct tccggctggc tggtttattg ctgataaatc tggagccggt   2400
gagcgtgggt ctcgcggtat cattgcagca ctggggccag atggtaagcc ctcccgtatc   2460
gtagttatct acacgacggg gagtcaggca actatggatg aacgaaatag acagatcgct   2520
gagataggtg cctcactgat taagcattgg taactgtcag accaagttta ctcatatata   2580
ctttagattg atttaaaact tcattttttaa tttaaaagga tctaggtgaa gatccttttt   2640
gataatctca tgaccaaaat cccttaacgt gagtttcgt tccactgagc gtcagacccc    2700
gtagaaaaga tcaaaggatc ttcttgagat cctttttttc tgcgcgtaat ctgctgcttg   2760
```

```
caaacaaaaa aaccaccgct accagcggtg gtttgtttgc cggatcaaga gctaccaact    2820
cttttccga  aggtaactgg cttcagcaga gcgcagatac caaatactgt ccttctagtg    2880
tagccgtagt taggccacca cttcaagaac tctgtagcac cgcctacata cctcgctctg    2940
ctaatcctgt taccagtggc tgctgccagt ggcgataagt cgtgtcttac cgggttggac    3000
tcaagacgat agttaccgga taaggcgcag cggtcgggct gaacgggggg ttcgtgcaca    3060
cagcccagct tggagcgaac gacctacacc gaactgagat acctacagcg tgagctatga    3120
gaaagcgcca cgcttcccga agggagaaag gcggacaggt atccggtaag cggcagggtc    3180
ggaacaggag agcgcacgag ggagcttcca gggggaaacg cctggtatct ttatagtcct    3240
gtcgggtttc gccacctctg acttgagcgt cgattttgt  gatgctcgtc aggggggcgg    3300
agcctatgga aaaacgccag caacgcggcc ttttacggt  tcctggcctt tgctggcct    3360
tttgctcaca tgttctttcc tgcgttatcc cctgattctg tggataaccg tattaccgcc    3420
tttgagtgag ctgataccgc tcgccgcagc cgaacgaccg agcgcagcga gtcagtgagc    3480
gaggaagcgg aagagcgccc aatacgcaaa ccgcctctcc ccgcgcgttg gccgattcat    3540
taatgcagct ggcacgacag gtttcccgac tggaaagcgg gcagtgagcg caacgcaatt    3600
aatgtgagtt agctcactca ttaggcaccc caggctttac actttatgct tccggctcgt    3660
atgttgtgtg gaattgtgag cggataacaa tttcacacag gaaacagcta tgaccatgat    3720
tacgccaagc gcgcattggt aattgatcgg ctggcacgcg gaatatagga ggtcgctgaa    3780
tagtaaactt gtagacttgg ctacagcata gagtatcttc gtagctctg  atgactgcta    3840
ggaaataatg ctacggataa tgtggggagg gcaaggcttg cgaatcgggt tgtaacgggc    3900
aaggcttgac tgaggggaca atagcatgtt taggcgaaaa gcggggcttc ggttgtacgc    3960
ggttaggagt cccctcagga tatagtagtt tcgcttttgc atagggaggg ggaaatgtag    4020
tcttatgcaa tactcttgta gtcttgcaac atgcttatgt aacgatgagt tagcaacatg    4080
ccttataagg agagaaaaag caccgtgcat gccgattggt gggagtaagg tggtatgatc    4140
gtggtatgat cgtgccttgt taggaaggca acagacgggt ctaacacgga ttggacgaac    4200
cactgaattc cgcattgcag agatattgta tttaagtgcc tagctcgata caataaacgc    4260
catttgacca ttcaccacat tggtgtgcac ctgggttgat ggccggaccg ttgattccct    4320
grcgactacg agcacatgca tgaagcagaa ggcttcattt ggtgaccccg acgtgatcgt    4380
tagggaatag tggtcggcca caggcggcgt ggcgatcctg tcctcatccg tctcgcttat    4440
tcggggagcg gacgatgacc ctagtagagg gggctgcggc ttaggagggc agaagctgag    4500
tggcgtcgga gggagcccta ctgcaggggg ccaacatacc ctaccgagaa ctcagagagt    4560
cgttggaaga cgggaaggaa gcccgacgac tgagcggtcc accccaggcg tgattccggt    4620
tgctctgcgt gattccggtc gcccggtgga tcaagcatgg aagccgtcat aaaggtgatt    4680
tcgtccgcgt gtaagaccta ttgcgggaaa acctctcctt ctaagaagga atagggggct    4740
atgttgtccc tgttacaaaa ggaagggttg cttacgtccc cctcagactt atattccccg    4800
gggtcctggg atcccattac cgcggcgctc tctcagcggg ctatggtact tggaaaatcg    4860
ggagagttaa aaacctgggg attggttttg ggggcattga aggcggctcg agatccggta    4920
ccttcaaata ctacaagtga aaagtgtttg cttaaacatg ttttattat  gattaaagga    4980
acaaaagagc acattcacaa gacccattac atatgggtac aaggaaaaca atttgaatag    5040
taatatacca tatttgccaa cataccatga ttgagtcaaa gtttagggag aaatgtgaat    5100
tataagattt ttataatgca tctttaggaa gtcaggaaga gccttgtagt atcaggaaca    5160
```

```
cagagaacaa gcaattgcct tgtcagcata ggaatggttg gtgacagttg ataatttaat    5220
ctgagagatt ttgagtgact aattctggag cagcttggtc atacagatat ctggcttaat    5280
tggaaggctg cattttttccc ccataaacct tctgctgatg tatcaggttg cattttttcag   5340 tgtgatgact cagtactgtg agtccaattt cattcccta agccttcatc catgagttac    5400
cagtattact ctgtgtaaag gaaaagtgaa ttgcacctgt tctcacagtg taatttcttt    5460 ctgattttttt ttctagatta agctccagct tttatgaagt ctggatgcag cagataacat   5520
acttttcatt ttaccccctga tactacagtg ctctgggtct tgttggaagg gacagagttt   5580
ttcagctttc ttcttttgaat tcctcattta cccggagaca gggagaggct cttctgcgtg   5640
tagtggttgt gcagagcctc atgcatcacg gagcatgaga agacgttccc ctgctgccac   5700
ctgctcttgt ccacggtgag cttgctgtag aggaagaagg agccgtcgga gtccagcacg   5760
ggaggcgtgg tcttgtagtt gttctccggc tgcccattgc tctcccactc cacggcgatg   5820
tcgctgggat agaagccttt gaccaggcag gtcaggctga cctggttctt ggtcagctca    5880
tcccgggatg ggggcagggt gtacacctgt ggttctcggg gctgcccttt ggctttggag    5940 atggtttttct cgatggggc tgggagggct ttgttggaga ccttgcactt gtactccttg    6000
ccattcagcc agtcctggtg caggacggtg aggacgctga ccacccggta cgtgctgttg    6060
tactgctcct cccgcggctt tgtcttggca ttatgcacct ccacgccgtc cacgtaccag    6120
ttgaacttga cctcagggtc ttcgtggctc acgtccacca ccacgcatgt gacctcaggg    6180
gtccgggaga tcatgagggt gtccttgggt tttgggggga agaggaagac tgacgatccc    6240
cccaggagtt caggtgctgg ggacggtggg gatgtgtgag ttttgtcaga agatttgggc    6300
tcctgatcag aatctgggca cggttctgga tcaattacat aaatctgggt tccgttgcct    6360
atgcccaggt agtatggcgg tgggtacatg agctccacct tgcagatgta gagtcccgtg    6420
tccatgcccc tcagtccttg gatagtgagg ttcacttgat ttccactgga ggtgcccgtg    6480
cagatggaat catctaggaa ggtcaactca ttccccatca tgtaggttgc cgcacagact    6540
tcagtcacct ggctgtcagc ctgccgaagc actgtcaccc ggacctcagt ggctttgcct    6600
ggagatgcat actcacacac aaagctrgcg atgcctcggc tgctggccag taccacagca    6660
ggctgggcca cgtgcattgc catgctcgcc atgcttggaa acaggagtgc aaggaccaga    6720
ctgagcagcg tcctctgtgt gagcagtaca cccatggtga actctgagtt gtctagagca    6780
aacagcagaa cagtgaaaat gtaaggatgg aatgctgtac atagtaccat gcagggtact    6840
ctatggtagg ctacaacagt aaattcgag cagttttttag gcaattaaat gttaacaagt    6900
agttttaaag taattctgtg gtaatgtgtc tgttgctata tccacctctc atgtgcatgt    6960
tcaaaaccat attcataaat ctatttatgt atttgcattc agttgtcttt tgggtagcaa    7020
actgtcccag aagccagttg cctctacata ttttttgttca gtgaaagcta gaattcattg    7080
atacttttca gtacctctga ttaaaacaca atctgatagg cttgcaaaac tggaaattca    7140
aagagcaaat ttcagtaaac tttaggtttg gacagatata tgagaaagca gaggcttgct    7200
gactatttta tttcttattt ttattcccta aaaataaatg tagagaaata tctgtttgtt    7260
gcacactact tgctatgagt agatcttcaa aagtatttttt acctttgttt tggtgatggc    7320
agaatagata aggaatgtaa tttatatggg gtcatgtagt ctaggagaaa gacacgcatg   7380
taattcatat tctgctctat tgcactttca ggtatggttt gctttgctca aagatatgca    7440
tgtgtactgt agtataaaact ttctgtggag ttaaattttta gtggtgacat tcagacagaa    7500
gagaaatgca gacatgataa aatagcaatg tttactataa aacagagcca ctgaatgaat    7560
```

```
tcttgttcat gacatagacc aatagaagat ttatacttgt tctgtctgtt tctattataa   7620
agagctgaac tgtacaacta ttgtatagcc agtgtgctta tataaagcac agcttttgga   7680
gccagcatga atctagttgc tttcctgaga tttatataat ctgtgaaagt cagaagtcct   7740
tcagagccca gcccctttata tgcgtactga gtgctgggggc ctcaggattg gattttctgt   7800
attaaacccc tcaaaagttt ttactgacca cgtgtgtgag tatacacaca cacattttc    7860 tcattttctt ttctgtatat aagttcacat gtatctatta ttgtaagaat atacgttat    7920 gcacccccca catttttatc ttgtgtagtg atcagcagct gcactttgca ggaattaaac   7980
ttctagagaa ttttcacatt aaaataactc cccagaattc actgaacacc atgattttgc   8040
tctctgtgca ctctgtaggg ctagaagtta atcaagcaaa ctgcaaagca tatcagatag   8100
tgaacgacag gataagatgt tctgaaatta aaaacatatt ttaagcacaa agaataagcc   8160
tcctgaaaac aaacacaaag cttttacaca taataaaata gtgcagaatg catacacagg   8220
tgagaagttt ttatagggggg tatcacgcag gtacttcacc cttaaagata caacacatag   8280
cacaataatt gttaattttt taaagtttag gtgcaagtaa gagctaatat agagagaagg   8340
taattccaga gagttgctta cctttcgagc ttgactgcta aaggcaatac agctttctag   8400
ctgtatgtac agacactggc tgagccctgg ggaatatata gtctgaattg tgacccaccc   8460
acaggttccc ttcagaagtt tgacctttga caccatagaa atcatttaat gggattgggt   8520
tagattttag tttcaatagg tccatttgg attgaatgga gagcaaatat tagttttta    8580 ttctgggtaa caatgtgttt tctgcctgtt ctgctaatcc atcaggactg ttggatggga   8640
gagaagactg ggaaatattg ctcatgttcc attgagcttc agttacaacc agataatggg   8700
atctttaaga aaacagaaaa atgtgggaac cttggagatg gaaaacataa ttagcaatta   8760
ttagttagtg tgcttattac tatggttgta gtaacagacc agaagtctgt ttcatttgat   8820
ccttcttgta tgtacaatgt gcatctgagc cacgctagac aggacataaa tgagaacaag   8880
acttgaccta ttatttcctt gacaaaatag gagaaataaa gaagcgtgca tgtgaaggag   8940
ccaactgaga ctagagtgaa gagcagacac actttctttc ctatagttgg aatatttaaa   9000
tctatctttt tatgggtgtg aatgcttat aacaaacttt tattctgagg atacagcaaa    9060
acatagctcc atacaatgca aaacaatact caatttcaaa tgtgtttatg atatgaactt   9120
gcagtgttcc tcaaagatct tccatgaata acttaatggc ctggcagatg acagaggaat   9180
tgtgaaattc agctggagga gtgttcatgg ttcgagggac aatcataata tacaatagca   9240
aatatatttc agttatagaa gctattgttc tgtattgaaa taatagaatt gacaaacagt   9300
aaagaaacca ttctgaccct ctgtaaagcac tgtttgattt aaaaatgggg gaaaaaagta   9360
caacataatt cttcaggaca tacatagaga tcactgcaat ctctgttaag cagaattact   9420
ttcctatacc actagctgaa gtttagtcag tgccattttc ttttgtttct ctccttcctt   9480
ttgtgaaaac atatatactg tggaaatcta cattctcctt gccaagtctg aggacttaag   9540
acaagatggt agtgcaaata atattttttt gctggatgtc tacaccacag gtatcaactg   9600
attttttttg tttcatttg tttttaatca cgtctttgc ttctatttca gccactaaga     9660
aagtctgaaa atcttgcctg cttttgtga tgatagatgt gcttcccagt aaatgttatc    9720
tctacctatg aaatgcatgt cagtctgcag aaagagaaag gagattggga ataggttttc   9780
tcagatgcac ttctctgtca tctggtgtca atcaaacact aataatttgt gtatagatat   9840
cttatatata tatatatatt tggaatttgc aggttggcat agttcagata gtcctgtcac   9900
attgtaatat cctggtgaga taacaaggaa aagagagacc gtttcggctc ttactaaggc   9960
```

```
agggaactgc ttaccagaca gggaggttct ggagatgaca tccagcatga aaagcacact      10020
tccaaatact taaaggtatc aagtctaact tgtcagacag gctccagaat aacttctgtc      10080
ctaatgctac agaaaagggg gaaggtatcc accatggcca aaattgtcag ccattttgtc      10140
tcagcaaaca gcagatctgg tcagtaagga caagattctt ccaaagcaac catgccatat      10200
ataattaagc atgtgtaatt aattaataaa aatataatt tagtgtattt cctccttttgg     10260
atgttatgaa gaaatgcttt tattaacaat tcaccataat ctgtcctaag agtagtgaat     10320
aacaacaggc tgcttctcac cctgtggttg ggtgtaccag tgagccagag ctaaacgcca     10380
cgtttcctct tttgtatccc atagcagaga gggtctccat ttcatttctg tagctcagaa     10440
agttgtagtg gatttacact acaagttgtg gtagtggagg tctgccggag tggcctctgt    10500
gaacagagcc cagcagctgt cccgtgtcct caaaagggag ctgccactgg ccagagctga    10560
gccagtgatc gatgctagat gtacctcagg aggagcaata tgtaagaaca actgctgtac    10620
aatggtagtt gggagaggtg agtgagaaaa tgtgagagaa acagccctga tgacactgag   10680
gtcagtgcgg aggagggcag gaggtgttcc aggtgtagaa cagaagttcc ctgcagccca  10740
agagaggccc atggtggagc actctgaccc tctgcagccc atggtatatc atataaaccct 10800
cagttctgtg acattatttt aactccatat cccttttctg ttcagggtca ctttgagttc   10860
acagccattt ctttatattt ctccaatatc agccttccat tgctacatat gagacttgga  10920
cagtacatct gattcagtca aatctgcctt cagaacgtcc ctgaagccct tcttagacag  10980
tctcaattct ccttcccttc atctctttta tcatacatgg accacggacc tgtccagacc  11040
tgagtcatat gtccatcttt acgtccatct ctatgtcttg tactttaaga caaataaaat 11100
atcaaggaaa ttgatgcagt tatgtcagtt atcactgtca tagtatcgtg ctgcaaatat 11160
aagatgagaa tgatcccaaa ggcttttaa agctgctcta tttgacttcc acatagtgtc  11220
ctgattccag acctacagaa cagttttgta tgcatttgac ttgcagagct ttgttttgtg  11280
agtcttataa aagccatttt tcctctccaa gaagtagccg gtggtttaaa acaatgtaga 11340
ttaagtgtgg agcatgagaa tttctgcttt tctgtcagat gagaaggata tactacactc  11400
tttcccaatg gaagaccagc tgcaagcaac aaaaattgtc catgaacaaa tgagatcttg 11460
atcagaacag gctgtcatca tagtgttgtc agcatacctg catagttggt ttgacttggg  11520
ggtctagaga gagtaagcaa caatcttctt gcagttggaa ggttacctgg gataggtggc 11580
aatggattgc cctgcccagc acagctgtgc aaagcagtac aaatagtttt gtcacacatt 11640
gtttgacaat gcttgtccca agaaaaggtc agctaaggct ctgctgccct ttcctatgcc 11700
aggcatttca ttgtgggtct gtccctaaac caacagtctc atgaataaag actcggagac 11760
ctgaaagtta taaagcact ttttatccaa aaggatatga agtccaggtg agctcacagg  11820
tcaaagcctc ttatccaatc actaaaacct actcagaact tgactcga              11868
```

<210> SEQ ID NO 20
<211> LENGTH: 10021
<212> TYPE: DNA
<213> ORGANISM: Artificial Sequence
<220> FEATURE:
<223> OTHER INFORMATION: pSIN-3.9-OM-CTLA4-Fc Vector

<400> SEQUENCE: 20

```
ctagactagg atccccgtg ctgcagaacc gagcggctat tgacttcttg ctcctagctc         60
acggccatgg ctgtgaggac attgcgggaa tgtgttgttt caatctgagt gatcacagtg        120
agtctataca gaagaagttc cagctaatga aggaacatgt caataagatc ggcgtgaaca        180
```

```
acgacccaat cggaagttgg ctgcgaggat tattcggagg aataggagaa tgggccgtac      240
acttgctgaa aggactgctt ttggggcttg tagttatctt gttgctagta gtatgcttgc      300 cttgccttt  gcaatgtgta tctagtagta ttcgaaagat gattgataat tcactcggct      360
atcgcgagga atataaaaaa attacaggag cttataagc  agcccgaaag aagagcgtag      420
gcgagttctt gtattccgtg tgatagctgg ttggattggt aattgatcgg ctggcacgcg      480
gaatatagga ggtcgctgaa tagtaaactt gtagacttgg ctacagcata gagtatcttc      540
tgtagctctg atgactgcta ggaaataatg ctacggataa tgtggggagg gcaaggcttg      600
cgaatcgggt tgtaacgggc aaggcttgac tgagggaca  atagcatgtt taggcgaaaa      660
gcggggcttc ggttgtacgc ggttaggagt ccctcagga  tatagtagtt tcgcttttgc      720
atagggaggg ggacggattg gacgaaccac tgaattccgc attgcagaga tattgtattt      780
aagtgcctag ctcgatacaa taaacgccat ttgaccattc  accacattgg tgtgcacctg      840
ggttgatggc cggaccgttg attccctgrc gactacgagc acatgcatga agcagaaggc      900
ttcatttggt gaccccgacg tgatcgttag ggaatacgcg ctcactggcc gtcgttttac      960
aacgtcgtga ctgggaaaac cctggcgtta cccaacttaa tcgccttgca gcacatcccc     1020
ctttcgccag ctggcgtaat agcgaagagg cccgcaccga tcgcccttcc caacagttgc     1080
gcagcctgaa tggcgaatgg aaattgtaag cgttaatatt ttgttaaaat tcgcgttaaa     1140
tttttgttaa atcagctcat tttttaacca ataggccgaa atcggcaaaa tcccttataa     1200
atcaaaagaa tagaccgaga tagggttgag tgttgttcca gtttggaaca agagtccact     1260
attaaagaac gtggactcca acgtcaaagg gcgaaaaacc gtctatcagg gcgatggccc     1320
actacgtgaa ccatcaccct aatcaagttt tttggggtcg aggtgccgta aagcactaaa     1380
tcggaaccct aaagggagcc cccgatttag agcttgacgg ggaaagccgg cgaacgtggc     1440
gagaaaggaa gggaagaaag cgaaaggagc gggcgctagg gcgctggcaa gtgtagcggt     1500
cacgctgcgc gtaaccacca cacccgccgc gcttaatgcg ccgctacagg gcgcgtcagg     1560
tggcactttt cggggaaatg tgcgcggaac ccctatttgt ttattttct  aaatacattc     1620 aaatatgtat ccgctcatga gacaataacc ctgataaatg cttcaataat attgaaaaag     1680
gaagagtatg agtattcaac atttccgtgt cgcccttatt cccttttttg cggcattttg     1740
ccttcctgtt tttgctcacc cagaaacgct ggtgaaagta aaagatgctg aagatcagtt     1800
gggtgcacga gtgggttaca tcgaactgga tctcaacagc ggtaagatcc ttgagagttt     1860
tcgccccgaa gaacgttttc caatgatgag cacttttaaa gttctgctat gtggcgcggt     1920
attatcccgt attgacgccg ggcaagagca actcggtcgc cgcatacact attctcagaa     1980
tgacttggtt gagtactcac cagtcacaga aaagcatctt acggatgca  tgacagtaag     2040 agaattatgc agtgctgcca taaccatgag tgataacact gcggccaact tacttctgac     2100
aacgatcgga ggaccgaagg agctaaccgc ttttttgcac aacatggggg atcatgtaac     2160
tcgccttgat cgttgggaac cggagctgaa tgaagccata ccaaacgacg agcgtgacac     2220
cacgatgcct gtagcaatgg caacaacgtt gcgcaaacta ttaactggcg aactacttac     2280
tctagcttcc cggcaacaat taatagactg gatggaggcg gataaagttg caggaccact     2340
tctgcgctcg gcccttccgg ctggctggtt tattgctgat aaatctggag ccggtgagcg     2400
tgggtctcgc ggtatcattg cagcactggg gccagatggt aagccctccc gtatcgtagt     2460
tatctacacg acggggagtc aggcaactat ggatgaacga atagacaga  tcgctgagat     2520 aggtgcctca ctgattaagc attggtaact gtcagaccaa gtttactcat atatacttta     2580
```

-continued

```
gattgattta aaacttcatt tttaatttaa aaggatctag gtgaagatcc tttttgataa    2640
tctcatgacc aaaatcccct aacgtgagtt ttcgttccac tgagcgtcag accccgtaga    2700
aaagatcaaa ggatcttctt gagatccttt ttttctgcgc gtaatctgct gcttgcaaac    2760
aaaaaaacca ccgctaccag cggtggtttg tttgccggat caagagctac caactctttt    2820
tccgaaggta actggcttca gcagagcgca gataccaaat actgtccttc tagtgtagcc    2880
gtagttaggc caccacttca agaactctgt agcaccgcct acatacctcg ctctgctaat    2940
cctgttacca gtggctgctg ccagtggcga taagtcgtgt cttaccgggt tggactcaag    3000
acgatagtta ccggataagg cgcagcggtc gggctgaacg gggggttcgt gcacacagcc    3060
cagcttggag cgaacgacct acaccgaact gagatacccta cagcgtgagc tatgagaaag    3120
cgccacgctt cccgaaggga gaaaggcgga caggtatccg gtaagcggca gggtcggaac    3180
aggagagcgc acgagggagc ttccaggggg aaacgcctgg tatctttata gtcctgtcgg    3240
gtttcgccac ctctgacttg agcgtcgatt tttgtgatgc tcgtcagggg gcggagcct    3300 atggaaaaac gccagcaacg cggccttttt acggttcctg gccttttgct ggccttttgc    3360
tcacatgttc tttcctgcgt tatcccctga ttctgtggat aaccgtatta ccgcctttga    3420
gtgagctgat accgctcgcc gcagccgaac gaccgagcgc agcgagtcag tgagcgagga    3480
agcggaagag cgcccaatac gcaaaccgcc tctccccgcg cgttggccga ttcattaatg    3540
cagctggcac gacaggtttc ccgactggaa agcgggcagt gagcgcaacg caattaatgt    3600
gagttagctc actcattagg caccccaggc tttacacttt atgcttccgg ctcgtatgtt    3660
gtgtggaatt gtgagcggat aacaatttca cacaggaaac agctatgacc atgattacgc    3720
caagcgcgca ttggtaattg atcggctggc acgcggaata taggaggtcg ctgaatagta    3780
aacttgtaga cttggctaca gcatagagta tcttctgtag ctctgatgac tgctaggaaa    3840
taatgctacg gataatgtgg ggagggcaag gcttgcgaat cgggttgtaa cgggcaaggc    3900
ttgactgagg ggacaatagc atgtttaggc gaaaagcggg gcttcggttg tacgcggtta    3960
ggagtcccct caggatatag tagttttcgct tttgcatagg gaggggggaaa tgtagtctta    4020 tgcaatactc ttgtagtctt gcaacatgct tatgtaacga tgagttagca acatgcctta    4080
taaggagaga aaaagcaccg tgcatgccga ttggtgggag taaggtggta tgatcgtggt    4140
atgatcgtgc cttgttagga aggcaacaga cgggtctaac acggattgga cgaaccactg    4200
aattccgcat tgcagagata ttgtatttaa gtgcctagct cgatacaata aacgccattt    4260
gaccattcac cacattggtg tgcacctggg ttgatggccg gaccgttgat ccctgrcga    4320 ctacgagcac atgcatgaag cagaaggctt catttggtga ccccgacgtg atcgttaggg    4380
aatagtggtc ggccacaggc ggcgtggcga tcctgtcctc atccgtctcg cttattcggg    4440
gagcggacga tgaccctagt agagggggct gcggcttagg agggcagaag ctgagtggcg    4500
tcggagggag ccctactgca gggggccaac atacccctacc gagaactcag agagtcgttg    4560
gaagacggga aggaagcccg acgactgagc ggtccacccc aggcgtgatt ccggttgctc    4620
tgcgtgattc cggtcgcccg gtggatcaag catggaagcc gtcataaagg tgatttcgtc    4680
cgcgtgtaag acctattgcg ggaaaacctc tccttctaag aaggaaatag ggctatgtt    4740 gtccctgtta caaaggaag ggttgcttac gtcccccctca gacttatatt ccccggggtc    4800
ctgggatccc attaccgcgg cgctctctca gcgggctatg gtacttggaa aatcgggaga    4860
gttaaaaacc tggggattgg ttttgggggc attgaaggcg gctcgaggtc gacggtatcg    4920
ataagcttgc agtccaaggc tttgtctgtg tacccagtga aatccttcct ctgttacata    4980
```

```
aagcccagat aggactcaga aatgtagtca ttccagcccc cctcttcctc agatctggag    5040
cagcacttgt ttgcagccag tcctccccaa aatgcacaga cctcgccgag tggagggaga    5100
tgtaaacagc gaaggttaat tacctccttg tcaaaaacac tttgtggtcc atagatgttt    5160
ctgtcaatct tacaaaacag aaccgagagg cagcgagcac tgaagagcgt gttcccatgc    5220
tgagttaatg agacttggca gctcgctgtg cagagatgat ccctgtgctt catgggaggc    5280
tgtaacctgt ctccccatcg ccttcacacc gcagtgctgt cctggacacc tcaccctcca    5340
taagctgtag gatgcagctg cccagggatc aagagacttt tcctaaggct cttaggactc    5400
atctttgccg ctcagtagcg tgcagcaatt actcatccca actatactga atgggtttct    5460
gccagctctg cttgtttgtc aataagcatt tcttcatttt gcctctaagt ttctctcagc    5520
agcaccgctc tgggtgacct gagtggccac ctggaacccg aggggcacag ccaccacctc    5580
cctgttgctg ctgctccagg gactcatgtg ctgctggatg gggggaagca tgaagttcct    5640
cacccagaca cctgggttgc aatggctgca gcgtgctctt cttggtatgc agattgtttc    5700
cagccattac ttgtagaaat gtgctgtgga agccctttgt atctctttct gtggcccttc    5760
agcaaaagct gtgggaaagc tctgaggctg cttctctggg tcgtggagga attgtatgtt    5820
ccttctttaa caaaaattat ccttaggaga gagcactgtg caagcattgt gcacataaaa    5880
caattcaggt tgaaagggct ctctggaggt ttccagcctg actactgctc gaagcaaggc    5940
caggttcaaa gatggctcag gatgctgtgt gccttcctga ttatctgtgc caccaatgga    6000
ggagattcac agccactctg cttcccgtgc cactcatgga gaggaatatt cccttatatt    6060
cagatagaat gttatccttt agctcagcct tccctataac cccatgaggg agctgcagat    6120
ccccatactc tccccttctc tggggtgaag gccgtgtccc ccagccccc ttcccaccct    6180 gtgccctaag cagcccgctg gcctctgctg gatgtgtgcc tatatgtcaa tgcctgtcct    6240
tgcagtccag cctgggacat ttaattcatc accagggtaa tgtggaactg tgtcatcttc    6300
ccctgcaggg tacaaagttc tgcacggggt cctttcggtt caggaaaacc ttcactggtg    6360
ctacctgaat caagctctat ttaataagtt cataagcaca tggatgtgtt ttcctagaga    6420
tacgttttaa tggtatcagt gattttttatt tgctttgttg cttacttcaa acagtgcctt    6480
tgggcaggag gtgagggacg ggtctgccgt tggctctgca gtgatttctc caggcgtgtg    6540
gctcaggtca gatagtggtc actctgtggc cagaagaagg acaaagatgg aaattgcaga    6600
ttgagtcacg ttaagcaggc atcttggagt gatttgaggc agtttcatga aagagctacg    6660
accacttatt gttgttttcc cctttacaa cagaagtttt catcaaaata acgtggcaaa    6720
gcccaggaat gttgggaaa agtgtagtta aatgttttgt aattcatttg tcggagtgct    6780
accagctaag aaaaaagtcc taccttggt atggtagtcc tgcagagaat acaacatcaa    6840
tattagtttg gaaaaaaaca ccaccaccac cagaaactgt aatggaaaat gtaaaccaag    6900
aaattccttg ggtaagagag aaaggatgtc gtatactggc caagtcctgc ccagctgtca    6960
gcctgctgac cctctgcagt tcaggaccat gaaacgtggc actgtaagac gtgtcccctg    7020
cctttgcttg cccacagatc tctgcccttg tgctgactcc tgcacacaag agcatttccc    7080
tgtagccaaa cagcgattag ccataagctg cacctgactt tgaggattaa gagtttgcaa    7140
ttaagtggat tgcagcagga gatcagtggc agggttgcag atgaaatcct tttctagggg    7200
tagctaaggg ctgagcaacc tgtcctacag cacaagccaa accagccaag ggttttcctg    7260
tgctgttcac agaggcaggg ccagctggag ctggaggagg ttgtgctggg acccttctcc    7320
ctgtgctgag aatggagtga tttctgggtg ctgttcctgt ggcttgcact gagcagctca    7380
```

| | |
|---|---|
| agggagatcg gtgctcctca tgcagtgcca aaactcgtgt ttgatgcaga aagatggatg | 7440 |
| tgcacctccc tcctgctaat gcagccgtga gcttatgaag gcaatgagcc ctcagtgcag | 7500 |
| caggagctgt agtgcactcc tgtaggtgct agggaaaatc tctggttccc agggatgcat | 7560 |
| tcataagggc aatatatctt gaggctgcgc caaatctttc tgaaatattc atgcgtgttc | 7620 |
| ccttaattta tagaaacaaa cacagcagaa taattattcc aatgcctccc ctcgaaggaa | 7680 |
| acccatattt ccatgtagaa atgtaaccta tatacacaca gccatgctgc atccttcaga | 7740 |
| acgtgccagt gctcatctcc catggcaaaa tactacaggt attctcacta tgttggacct | 7800 |
| gtgaaaggaa ccatggtaag aaacttcggt taaaggtatg gctgcaaaac tactcatacc | 7860 |
| aaaacagcag agctccagac ctcctcttag gaaagagcca cttggagagg gatggtgtga | 7920 |
| aggctggagg tgagagacag agcctgtccc agttttcctg tctctatttt ctgaaacgtt | 7980 |
| tgcaggagga aaggacaact gtactttcag gcatagctgg tgccctcacg taaataagtt | 8040 |
| ccccgaactt ctgtgtcatt tgttcttaag atgctttggc agaacacttt gagtcaattc | 8100 |
| gcttaactgt gactaggtct gtaaataagt gctccctgct gataaggttc aagtgacatt | 8160 |
| tttagtggta tttgacagca tttaccttgc tttcaagtct tctaccaagc tcttctatac | 8220 |
| ttaagcagtg aaaccgccaa gaaacccttc cttttatcaa gctagtgcta ataccatta | 8280 |
| acttcatagg ttagatacgg tgctgccagc ttcacctggc agtggttggt cagttctgct | 8340 |
| ggtgacaaag cctccctggc ctgtgctttt acctagaggt gaatatccaa gaatgcagaa | 8400 |
| ctgcatggaa agcagagctg caggcacgat ggtgctgagc cttagctgct tcctgctggg | 8460 |
| agatgtggat gcagagacga atgaaggacc tgtcccttac tcccctcagc attctgtgct | 8520 |
| atttagggtt ctaccagagt ccttaagagg tttttttttt ttttggtcca aaagtctgtt | 8580 |
| tgtttggttt tgaccactga gagcatgtga cacttgtctc aagctattaa ccaagtgtcc | 8640 |
| agccaaaatc aattgcctgg gagacgcaga ccattacctg gaggtcagga cctcaataaa | 8700 |
| tattaccagc ctcattgtgc cgctgacaga ttcagctggc tgctccgtgt tccagtccaa | 8760 |
| cagttcggac gccacgtttg tatatatttg caggcagcct cgggggggacc atctcaggag | 8820 |
| cagagcaccg gcagccgcct gcagagccgg gcagtacctc aacatgggtg tactgctcac | 8880 |
| acagaggacg ctgctcagtc tggtccttgc actcctgttt ccaagcatgg cgagcatggc | 8940 |
| aatgcacgtg gcccagcctg ctgtggtact ggccagcagc cgaggcatcg cyagctttgt | 9000 |
| gtgtgagtat gcatctccag gcaaagccac tgaggtccgg gtgacagtgc ttcggcaggc | 9060 |
| tgacagccag gtgactgaag tctgtgcggc aacctacatg atggggaatg agttgacctt | 9120 |
| cctagatgat tccatctgca cgggcacctc cagtggaaat caagtgaacc tcactatcca | 9180 |
| aggactgagg gccatggaca cgggactcta catctgcaag gtggagctca tgtacccacc | 9240 |
| gccatactac ctgggcatag gcaacggaac ccagatttat gtaattgatc cagaaccgtg | 9300 |
| cccagattct gatcaggagc ccaaatcttc tgacaaaact cacacatccc caccgtcccc | 9360 |
| agcacctgaa ctcctggggg gatcgtcagt cttcctcttc cccccaaaac ccaaggacac | 9420 |
| cctcatgatc tcccggaccc ctgaggtcac atgcgtggtg gtggacgtga gccacgaaga | 9480 |
| ccctgaggtc aagttcaact ggtacgtgga cggcgtggag gtgcataatg ccaagacaaa | 9540 |
| gccgcgggag gagcagtaca acagcacgta ccgggtggtc agcgtcctca ccgtcctgca | 9600 |
| ccaggactgg ctgaatggca aggagtacaa gtgcaaggtc tccaacaaag ccctcccagc | 9660 |
| ccccatcgag aaaaccatct ccaaagccaa agggcagccc cgagaaccac aggtgtacac | 9720 |
| cctgccccca tcccgggatg agctgaccaa gaaccaggtc agcctgacct gcctggtcaa | 9780 |

| | | | | |
|---|---|---|---|---|
| aggcttctat | cccagcgaca | tcgccgtgga | gtgggagagc | aatgggcagc | cggagaacaa | 9840 |
| ctacaagacc | acgcctcccg | tgctggactc | cgacggctcc | ttcttcctct | acagcaagct | 9900 |
| caccgtggac | aagagcaggt | ggcagcaggg | gaacgtcttc | tcatgctccg | tgatgcatga | 9960 |
| ggctctgcac | aaccactaca | cgcagaagag | cctctccctg | tctccgggta | aatgaggaat | 10020 |
| t | | | | | | 10021 |

<210> SEQ ID NO 21
<211> LENGTH: 7350
<212> TYPE: DNA
<213> ORGANISM: Artificial Sequence
<220> FEATURE:
<223> OTHER INFORMATION: pSIN-1.8-OM-IFNa-2B Vector

<400> SEQUENCE: 21

| | | | | | |
|---|---|---|---|---|---|
| tcgagatcaa | ttgctagact | aggatccccc | gtgctgcaga | accgagcggc | tattgacttc | 60 |
| ttgctcctag | ctcacggcca | tggctgtgag | gacattgcgg | gaatgtgttg | tttcaatctg | 120 |
| agtgatcaca | gtgagtctat | acagaagaag | ttccagctaa | tgaaggaaca | tgtcaataag | 180 |
| atcggcgtga | acaacgaccc | aatcggaagt | tggctgcgag | gattattcgg | aggaatagga | 240 |
| gaatgggccg | tacacttgct | gaaaggactg | cttttgggc | ttgtagttat | cttgttgcta | 300 |
| gtagtatgct | tgccttgcct | tttgcaatgt | gtatctagta | gtattcgaaa | gatgattgat | 360 |
| aattcactcg | gctatcgcga | ggaatataaa | aaaattacag | gaggcttata | agcagcccga | 420 |
| aagaagagcg | taggcgagtt | cttgtattcc | gtgtgatagc | tggttggatt | ggtaattgat | 480 |
| cggctggcac | gcggaatata | ggaggtcgct | gaatagtaaa | cttgtagact | tggctacagc | 540 |
| atagagtatc | ttctgtagct | ctgatgactg | ctaggaaata | atgctacgga | taatgtgggg | 600 |
| agggcaaggc | ttgcgaatcg | ggttgtaacg | ggcaaggctt | gactgagggg | acaatagcat | 660 |
| gtttaggcga | aaagcggggc | ttcggttgta | cgcggttagg | agtcccctca | ggatatagta | 720 |
| gtttcgcttt | tgcataggga | gggggacgga | ttggacgaac | cactgaattc | cgcattgcag | 780 |
| agatattgta | tttaagtgcc | tagctcgata | caataaacgc | catttgacca | ttcaccacat | 840 |
| tggtgtgcac | ctgggttgat | ggccggaccg | ttgattccct | grcgactacg | agcacatgca | 900 |
| tgaagcagaa | ggcttcattt | ggtgaccccg | acgtgatcgt | tagggaatac | gcgctcactg | 960 |
| gccgtcgttt | tacaacgtcg | tgactgggaa | aaccctggcg | ttacccaact | taatcgcctt | 1020 |
| gcagcacatc | cccctttcgc | cagctggcgt | aatagcgaag | aggcccgcac | cgatcgccct | 1080 |
| tcccaacagt | tgcgcagcct | gaatggcgaa | tggaaattgt | aagcgttaat | attttgttaa | 1140 |
| aattcgcgtt | aaattttgt | taaatcagct | cattttttaa | ccaataggcc | gaaatcggca | 1200 |
| aaatccctta | taaatcaaaa | gaatagaccg | agatagggtt | gagtgttgtt | ccagtttgga | 1260 |
| acaagagtcc | actattaaag | aacgtggact | ccaacgtcaa | agggcgaaaa | accgtctatc | 1320 |
| agggcgatgg | cccactacgt | gaaccatcac | cctaatcaag | ttttttgggg | tcgaggtgcc | 1380 |
| gtaaagcact | aaatcggaac | cctaaaggga | gcccccgatt | tagagcttga | cggggaaagc | 1440 |
| cggcgaacgt | ggcgagaaag | gaagggaaga | aagcgaaagg | agcgggcgct | agggcgctgg | 1500 |
| caagtgtagc | ggtcacgctg | cgcgtaacca | ccacacccgc | cgcgcttaat | gcgccgctac | 1560 |
| agggcgcgtc | aggtggcact | tttcggggaa | atgtgcgcgg | aacccctatt | tgtttatttt | 1620 |
| tctaaataca | ttcaaatatg | tatccgctca | tgagacaata | accctgataa | atgcttcaat | 1680 |
| aatattgaaa | aaggaagagt | atgagtattc | aacatttccg | tgtcgccctt | attccctttt | 1740 |
| ttgcggcatt | ttgccttcct | gtttttgctc | acccagaaac | gctggtgaaa | gtaaaagatg | 1800 |

```
ctgaagatca gttgggtgca cgagtgggtt acatcgaact ggatctcaac agcggtaaga    1860
tccttgagag ttttcgcccc gaagaacgtt ttccaatgat gagcacttttt aaagttctgc   1920
tatgtggcgc ggtattatcc cgtattgacg ccgggcaaga gcaactcggt cgccgcatac    1980
actattctca gaatgacttg gttgagtact caccagtcac agaaaagcat cttacggatg    2040
gcatgacagt aagagaatta tgcagtgctg ccataaccat gagtgataac actgcggcca    2100
acttacttct gacaacgatc ggaggaccga aggagctaac cgcttttttg cacaacatgg    2160
gggatcatgt aactcgcctt gatcgttggg aaccggagct gaatgaagcc ataccaaacg    2220
acgagcgtga caccacgatg cctgtagcaa tggcaacaac gttgcgcaaa ctattaactg    2280
gcgaactact tactctagct tcccggcaac aattaataga ctggatggag gcggataaag    2340
ttgcaggacc acttctgcgc tcggcccttc cggctggctg gtttattgct gataaatctg    2400
gagccggtga gcgtgggtct cgcggtatca ttgcagcact ggggccagat ggtaagccct    2460
cccgtatcgt agttatctac acgacgggga gtcaggcaac tatggatgaa cgaaatagac    2520
agatcgctga gataggtgcc tcactgatta agcattggta actgtcagac caagtttact    2580
catatatact ttagattgat ttaaaacttc atttttaatt taaaaggatc taggtgaaga    2640
tcctttttga taatctcatg accaaaatcc cttaacgtga gttttcgttc cactgagcgt    2700
cagaccccgt agaaaagatc aaaggatctt cttgagatcc ttttttttctg cgcgtaatct    2760
gctgcttgca acaaaaaaa ccaccgctac cagcggtggt ttgtttgccg gatcaagagc    2820
taccaactct ttttccgaag gtaactggct tcagcagagc gcagatacca atactgtcc    2880
ttctagtgta gccgtagtta ggccaccact tcaagaactc tgtagcaccg cctacatacc    2940
tcgctctgct aatcctgtta ccagtggctg ctgccagtgg cgataagtcg tgtcttaccg    3000
ggttggactc aagacgatag ttaccggata aggcgcagcg gtcgggctga acgggggggtt   3060
cgtgcacaca gcccagcttg gagcgaacga cctacaccga actgagatac ctacagcgtg    3120
agctatgaga aagcgccacg cttcccgaag ggagaaaggc ggacaggtat ccggtaagcg    3180
gcagggtcgg aacaggagag cgcacgaggg agcttccagg gggaaacgcc tggtatcttt    3240
atagtcctgt cgggtttcgc cacctctgac ttgagcgtcg atttttgtga tgctcgtcag    3300
gggggcggag cctatggaaa aacgccagca acgcggcctt tttacggttc ctggcctttt    3360
gctggccttt tgctcacatg ttctttcctg cgttatcccc tgattctgtg ataaccgta    3420
ttaccgcctt tgagtgagct gataccgctc gccgcagccg aacgaccgag cgcagcgagt    3480
cagtgagcga ggaagcggaa gagcgcccaa tacgcaaacc gcctctcccc gcgcgttggc    3540
cgattcatta atgcagctgg cacgacaggt ttcccgactg gaaagcgggc agtgagcgca    3600
acgcaattaa tgtgagttag ctcactcatt aggcaccccca ggctttacac tttatgcttc    3660
cggctcgtat gttgtgtgga attgtgagcg gataacaatt tcacacagga aacagctatg    3720
accatgatta cgccaagcgc gcattggtaa ttgatcggct ggcacgcgga atataggagg    3780
tcgctgaata gtaaacttgt agacttggct acagcataga gtatcttctg tagctctgat    3840
gactgctagg aaataatgct acggataatg tgggagggc aaggcttgcg aatcgggttg    3900
taacgggcaa ggcttgactg aggggacaat agcatgttta ggcgaaaagc ggggcttcgg    3960
ttgtacgcgg ttaggagtcc cctcaggata tagtagtttc gcttttgcat agggaggggg    4020
aaatgtagtc ttatgcaata ctcttgtagt cttgcaacat gcttatgtaa cgatgagtta    4080
gcaacatgcc ttataaggag agaaaaagca ccgtgcatgc cgattggtgg gagtaaggtg    4140
gtatgatcgt ggtatgatcg tgccttgtta ggaaggcaac agacgggtct aacacggatt    4200
```

```
ggacgaacca ctgaattccg cattgcagag atattgtatt taagtgccta gctcgataca   4260
ataaacgcca tttgaccatt caccacattg gtgtgcacct gggttgatgg ccggaccgtt   4320
gattccctgr cgactacgag cacatgcatg aagcagaagg cttcatttgg tgaccccgac   4380
gtgatcgtta gggaatagtg gtcggccaca ggcggcgtgg cgatcctgtc ctcatccgtc   4440
tcgcttattc ggggagcgga cgatgaccct agtagagggg gctgcggctt aggagggcag   4500
aagctgagtg gcgtcggagg gagccctact gcaggggggcc aacatacccct accgagaact   4560
cagagagtcg ttggaagacg ggaaggaagc ccgacgactg agcggtccac cccaggcgtg   4620
attccggttg ctctgcgtga ttccggtcgc ccggtggatc aagcatggaa gccgtcataa   4680
aggtgatttc gtccgcgtgt aagacctatt gcgggaaaac ctctccttct aagaaggaaa   4740
tagggggctat gttgtccctg ttacaaaagg aagggttgct tacgtccccc tcagacttat   4800
attccccggg gtcctgggat cccattaccg cggcgctctc tcagcgggct atggtacttg   4860
gaaaatcggg agagttaaaa acctgggggat tggttttggg ggcattgaag gcggctcgac   4920
ggatccgtta accctagaac tagtggatct ctgcccttgt gctgactcct gcacacaaga   4980
gcatttccct gtagccaaac agcgattagc cataagctgc acctgacttt gaggattaag   5040
agtttgcaat taagtggatt gcagcaggag atcagtggca gggttgcaga tgaaatcctt   5100
ttctaggggt agctaagggc tgagcaacct gtcctacagc acaagccaaa ccagccaagg   5160
gttttcctgt gctgttcaca gaggcagggc cagctggagc tggaggaggt tgtgctggga   5220
cccttctccc tgtgctgaga atggagtgat ttctgggtgc tgttcctgtg gcttgcactg   5280
agcagctcaa gggagatcgg tgctcctcat gcagtgccaa aactcgtgtt tgatgcagaa   5340
agatggatgt gcacctcccct cctgctaatg cagccgtgag cttatgaagg caatgagccc   5400
tcagtgcagc aggagctgta gtgcactcct gtaggtgcta gggaaaatct ctggttccca   5460
gggatgcatt cataagggca atatatcttg aggctgcgcc aaatctttct gaaatattca   5520
tgcgtgttcc cttaatttat agaaacaaac acagcagaat aattattcca atgcctcccc   5580
tcgaaggaaa cccatatttc catgtagaaa tgtaacctat atacacacag ccatgctgca   5640
tccttcagaa cgtgccagtg ctcatctccc atggcaaaat actacaggta ttctcactat   5700
gttggacctg tgaaaggaac catggtaaga aacttcggtt aaaggtatgg ctgcaaaact   5760
actcatacca aaacagcaga gctccagacc tcctcttagg aaagagccac ttggagaggg   5820
atggtgtgaa ggctggaggt gagagacaga gcctgtccca gttttcctgt ctctattttc   5880
tgaaacgttt gcaggaggaa aggacaactg tactttcagg catagctggt gccctcacgt   5940
aaataagttc cccgaacttc tgtgtcattt gttcttaaga tgctttggca gaacactttg   6000
agtcaattcg cttaactgtg actaggtctg taaataagtg ctccctgctg ataaggttca   6060
agtgacattt ttagtggtat ttgacagcat ttaccttgct ttcaagtctt ctaccaagct   6120
cttctatact taagcagtga aaccgccaag aaacccttcc ttttatcaag ctagtgctaa   6180
ataccattaa cttcataggt tagatacggt gctgccagct tcacctggca gtggttggtc   6240
agttctgctg gtgacaaagc ctccctggcc tgtgctttta cctagaggtg aatatccaag   6300
aatgcagaac tgcatggaaa gcagagctgc aggcacgatg gtgctgagcc ttagctgctt   6360
cctgctggga gatgtggatg cagagacgaa tgaaggacct gtcccttact cccctcagca   6420
ttctgtgcta tttagggttc taccagagtc cttaagaggt ttttttttttt tttggtccaa   6480
aagtctgttt gtttggtttt gaccactgag agcatgtgac acttgtctca agctattaac   6540
caagtgtcca gccaaaatca attgcctggg agacgcagac cattacctgg aggtcaggac   6600
```

```
ctcaataaat attaccagcc tcattgtgcc gctgacagat tcagctggct gctccgtgtt    6660
ccagtccaac agttcggacg ccacgtttgt atatatttgc aggcagcctc gggggggacca   6720 tctcaggagc agagcaccgg cagccgcctg cagagccggg cagtacctca ccatggcttt    6780
gacctttgcc ttactggtgg ctctcctggt gctgagctgc aagagcagct gctctgtggg    6840
ctgcgatctg cctcagaccc acagcctggg cagcaggagg accctgatgc tgctggctca    6900
gatgaggaga atcagcctgt ttagctgcct gaaggatagg cacgattttg gctttcctca    6960
agaggagttt ggcaaccagt ttcagaaggc tgagaccatc cctgtgctgc acgagatgat    7020
ccagcagatc tttaacctgt ttagcaccaa ggatagcagc gctgcttggg atgagaccct    7080
gctggataag ttttacaccg agctgtacca gcagctgaac gatctggagg cttgcgtgat    7140
ccagggcgtg ggcgtgaccg agacccctct gatgaaggag gatagcatcc tggctgtgag    7200
gaagtacttt cagaggatca ccctgtacct gaaggagaag aagtacagcc cctgcgcttg    7260
ggaagtcgtg agggctgaga tcatgaggag ctttagcctg agcaccaacc tgcaagagag    7320
cttgaggtct aaggagtaaa aagtctaggc                                      7350
```

<210> SEQ ID NO 22
<211> LENGTH: 16051
<212> TYPE: DNA
<213> ORGANISM: Artificial Sequence
<220> FEATURE:
<223> OTHER INFORMATION: 16 kbp Ovalbumin Sequence

<400> SEQUENCE: 22

```
ctgcagccca ggcagcacac tagagcagag aaatctagtt agcagcaacc actggcagac      60
agaaatgatt atatagatta catactgacc ctagcctctt acactgccta ctgcatcact     120
gaaaggactg ggaagaagag agtgcaataa cgaagctgaa gctaggagga aggcaaggag     180
aactgaagct gactagggaa aaggggggatt aaaggtttaa gtgtctattc catagtttgc     240
tggtttgttt tttgtcaatt cctgaatcag taattttttat gttaattagc aaaaaattac     300
aaacactccc caagtcagga ctgttaccta caacagaagc tcagatcagc tgagccttag     360
tcttttggtc cctccctagg gaatgctgta tgtgtctctc tctccaggcc tgctcaaaat     420
tgacctcaga cccaaacttt tgctgaatct ccagtaccac ctcttttgct cctaactaga     480
taacaaagcc ctgagcgctt tgcttttagc aaagctttaa gtgccattac caactgcacc     540
tggagccttt acctaccccct atggacccag gctctatatt taagctctgc cctgaacctt     600
cacttctttc ctgtcctaag ttagatgtac tagtatggtg tgtactatgt ctccagttca     660
aacacagctg tgcccatacc tggccaagga ctcctagtat gacctgggct gtgccttgct     720
gctaaggacc tgctgggtga ttgctggacc tgatcctaat cctgaattaa gaaatgattt     780
cttggcttga ctggatgtgc cctgtggtat gatactgcct tatgatttgg actcttgttt     840
gcagctgtgc aaatccctaa ggagcccagt ctctggccac ctggaatctt gtcactacca     900
aacttcctga gggactggtc ttgctctggg ttctgatctc tggacagtac tcacccttta     960
ctcagcccag gctcccagtt aagccccttt ccaccctgcc aggctctccg ctccatccct    1020
agcaggggct ctcatgacag tgtgaccccc ccttactcag gtcagggcca cttgtgccac    1080 gttccttttcc tgtcttctgt ccctgccttg gctctaaagc agtgtgctac catccacaac    1140
cactgcatct ctctaaagta agcctctcct gagcccaagt ctctgtaacg aggaaggatg    1200
cactttgctc agaaggatgc gaggctgctt ctgagctctg agggcactga cctcccatga    1260
ggtacacccc ataccccagga ccacaattca gcctgctgga accatcaact cctgctggag    1320
```

```
taaggccata gcaagaccag catccacctc cctgcagccc tgccctgccc agatattggg    1380
cctgctgatc tcaggatgca gacttgcttc tcagcttgac ctaagcattg ccctgtcttt    1440
atggacccac ctggttagca agttcagtgc agaaggaggc tgttggcatc tagctaattt    1500
tccacccaca ttactgtctg ctgactcatt ctacgtctct cccatcttgt tacaataata    1560
atttgggaga tcatattgaa ggtcttaata aagtcaaggc atgtgatatt ctctgctttg    1620
cctttgtttc tagaataagc cacttcatca tagaagatga aaatgctgat cagcagagat    1680
ctgtgcttga taaatccatg ctggcttttc ctatcacctt atattccttc atatgccttg    1740
agacacccaa ggaggccttg gatcagagct gtctgtagca gtcctaactg gtatacaatt    1800
agttgtacaa caggtagtga tccgcataat agttggcgtg agaaagtggg cctgtgctgt    1860
gtcaagcata gagtttgggt tccagtcctg ttctgcatgg cacatatgcc tgagcagctg    1920
ggtaatctct gcattccaat tggaaggcag gggcctgtag gcagttccca cttggcatgg    1980
gtgattgtac cacctgtgtc ctcatctgtg aagcatcatg ttttcattca aatatccttt    2040
tgtttgacag tagaaatgaa cagaattgtt ttttttttcct aagcaaattc tgcaagagct    2100
ctgaagaaca aggtgtcagt gaacttctag ctccatagat aggacttgca tcacatgtca    2160
tgccttgatt ggaggtctat ccgatactga acaacttgtg gttccctgag ggaatgtaag    2220
attactgata ctactctctc tttatgttag ctacaataaa tggtaggtta agcaatagat    2280
acagagtttg agtgcctttc ttacaagcat catagtgaac aaatccactg gtgatctacc    2340
ttttcaataa ctacagagaa ttgtaatctc ttggattctc ctccttcccc gttctgaaaa    2400
tgtgttcttt ttttccaaat cagaaacctt cctcaaccac cctgactatt ctttggacat    2460
tgttttgttc ttgctcctaa ataggcttta taattttttgt aagtgaaagg ctttgcatgc    2520
aggtgaggct acaactcatt cagtaacaat gaggaagact gtcagatttt ggggaaaatt    2580
ctcccaccca acctttttgct agccagtaag atgtaatcac tgaatgtcat gccacaaaga    2640
ccataccaac atcagaccac atatctacag gaagctttaa ggaatcattg actgtacagt    2700
gaagggtaaa tcaaattaaa atgaatgtga ggtctgatac gagatatcct catgggaatc    2760
aagagcaaag acaaatagtt tttcacagtc ttgtcatgat ctgtcacaga ccaaggcagc    2820
acagcaggca acaatgttgg tctcttcaga atggcacagc accgctgcag aaaaatgcca    2880
ggtggactat gaactcacat ccaaaggagc ttgacctgat acctgatttt cttcaaacag    2940
gggaaacaac acaatcccac aaaatagctc agagagaaac catcactgat ggctacagca    3000
ccaaggtatg caatggcaat ccattcgaca ttcatctgtg acctgagcaa aatgattat     3060 ctctccatga atggttgctt ctttccctca tgaaaaggca atttccacac tcacaatatg    3120
caacaaagac aaacagagaa caattaatgt gctccttcct aatgtcaaaa ttgtagtggc    3180
aaagaggaga acaaaatctc aagttctgag taggttttag tgattggata agaggctttg    3240
acctgtgagc tcacctggac ttcatatcct tttggataaa aagtgctttt ataactttca    3300
ggtctccgag tctttattca tgagactgtt ggtttaggga cagacccaca atgaaatgcc    3360
tggcatagga aagggcagca gagccttagc tgacctttc ttgggacaag cattgtcaaa    3420
caatgtgtga caaaactatt tgtactgctt tgcacagctg tgctgggcag ggcaatccat    3480
tgccacctat cccaggtaac cttccaactg caagaagatt gttgcttact ctctctagac    3540
ccccaagtca aaccaactat gcaggtatgc tgacaacgct atgatgacag cctgttctga    3600
tcaagatctc atttgttcat ggacaatttt tgttgcttgc agctggtctt ccattgggaa    3660
agagtgtagt atatccttct catctgacag aaaagcagaa attctcatgc tccacactta    3720
```

```
atctacattg ttttaaacca ccagctactt cttggagagg aaaaatggct tttataagac    3780
tcacaaaaca aagctctgca agtcaaatgc atacaaaact gttctgtagg tctggaatca    3840
ggacactatg tggaagtcaa atagagaagc tttaaaaaaa cctttgggat cattctcatc    3900
ttatatttgc agcacgatac tatgacagtg ataactgaca taactgcatc aatttccttg    3960
atattttatt tgtcttaaag tacaagacat agagatggac gtaaagatgg acatatgact    4020
caggtctgga caggtccgtg gtccatgtat gataaaagag atgaagggaa ggagaatgga    4080
gactgtctaa gaagggcttc agggacgttc tgaaggcaga tttgactgaa tcagatgtac    4140
tgtccaagtc tcatatgtag caatggaaga ctgatattgg agaaatataa agaaatggct    4200
gtgaactcaa agtgaccctg aacagaaaag ggatatggag ttaaaataat ggcacagaac    4260
tgaggtttat atgatatacc atgggctgca gagggtcaga gtgctccacc atgggcctct    4320
cttgggctgc agggaacttc tgttctacac ctggaacacc tcctgccctc ctccgcactg    4380
acctcagtgt catcagggct gtttctctca cattttctca ctcacctctc caactacca    4440
ttgtacagca gttgttctta catcttgctc ctcctgaggt gcatctagca tcgatcactg    4500
gctcagctct ggccagtggc agctcccttt tgaggcacg ggacagctgc tgggctctgt    4560
tcacagaggc cactccagca gacctccact accacaactt gtagtgtaaa tccactacaa    4620
ctttctgagc tacagaaatg aaatggagac cctctctgct atgggataca aagaggaaa    4680
cgtggcgttt agtgctctgg ctcactggta cacccaacca cagggtgaga agcagcctgt    4740
tgttattcac tactcttagg acagattatg gtgaattgtt aataaaagca tttcttcata    4800
acatccaaag gaggaaatac actaaattat attttttatt tattaattac acatgcttaa    4860
ttatatatgg catggttgct ttgaaagaac cttgtcctta ctgaccagat ctgctgtttg    4920
ctgagacaaa atggctgaca attttggcca tggtggatac cttccccctt ttctgtagca    4980
ttaggacaga agttattctg gagcctgtct gacaagtcag acttgataac tttaagtatt    5040
tggaagtgtg cttttcatgc tggatgtcat ctccagaacc tccctgtctg gtaagcagtt    5100
ccctgcctta gtaagagccg aaacggtctc tcttttcctt gttatctcac caggatatta    5160
caatgtgaca ggactatctg aactacgcca acctgcaaat tccaaatata tatatata    5220
tgtaagatat ctatacacaa attattagtg tttgattgac accagatgac agagaagtgc    5280
atctgagaaa acctattccc aatctccttt ctctttctgc agactgacat gcatttcata    5340
ggtagagata acatttactg ggaagcacat ctatcatcat aaaaagcagg caagatttc    5400
agactttctt agtggctgaa atagaagcaa aagacgtgat taaaaacaaa atgaaacaaa    5460
aaaaatcagt tgatacctgt ggtgtagaca tccagcaaaa aatattatt tgcactacca    5520
tcttgtctta agtcctcaga cttggcaagg agaatgtaga tttctacagt atatatgttt    5580
tcacaaaagg aaggagagaa acaaagaaaa atggcactga ctaaacttca gctagtggta    5640
taggaaagta attctgctta acagagattg cagtgatctc tatgtatgtc ctgaagaatt    5700
atgttgtact ttttccccc atttttaaat caaacagtgc tttacagagg tcagaatggt    5760
ttctttactg tttgtcaatt ctattatttc aatacagaac aatagcttct ataactgaaa    5820
tatatttgct attgtatatt atgattgtcc ctcgaaccat gaacactcct ccagctgaat    5880
ttcacaattc ctctgtcatc tgccaggcca ttaagttatt catggaagat ctttgaggaa    5940
cactgcaagt tcatatcata aacacatttg aaattgagta ttgttttgca ttgtatggag    6000
ctatgttttg ctgtatcctc agaaaaaaag tttgttataa agcattcaca cccataaaaa    6060
gatagattta aatattccag ctataggaaa gaaagtgcgt ctgctcttca ctctagtctc    6120
```

-continued

```
agttggctcc ttcacatgca tgcttcttta tttctcctat tttgtcaaga aaataatagg    6180
tcacgtcttg ttctcactta tgtcctgcct agcatggctc agatgcacgt tgtagataca    6240
agaaggatca aatgaaacag acttctggtc tgttactaca accatagtaa taagcacact    6300
aactaataat tgctaattat gttttccatc tctaaggttc ccacattttt ctgttttctt    6360
aaagatccca ttatctggtt gtaactgaag ctcaatggaa catgagcaat atttcccagt    6420
cttctctccc atccaacagt cctgatggat tagcagaaca ggcagaaaac acattgttac    6480
ccagaattaa aaactaatat tgctctcca ttcaatccaa aatggaccta ttgaaactaa    6540
aatctaaccc aatcccatta aatgatttct atggcgtcaa aggtcaaact tctgaaggga    6600
acctgtgggt gggtcacaat tcaggctata tattccccag ggctcagcca gtgtctgtac    6660
atacagctag aaagctgtat tgcctttagc agtcaagctc gaaaggtaag caactctctg    6720
gaattacctt ctctctatat tagctcttac ttgcacctaa actttaaaaa attaacaatt    6780
attgtgctat gtgttgtatc tttaaggggtg aagtacctgc gtgatacccc ctataaaaac    6840
ttctcacctg tgtatgcatt ctgcactatt ttattatgtg taaaagcttt gtgtttgttt    6900
tcaggaggct tattctttgt gcttaaaata tgttttaat ttcagaacat cttatcctgt    6960
cgttcactat ctgatatgct ttgcagtttg cttgattaac ttctagccct acagagtgca    7020
cagagagcaa aatcatggtg ttcagtgaat tctggggagt tatttaatg tgaaaattct    7080 ctagaagttt aattcctgca aagtgcagct gctgatcact acacaagata aaaatgtggg    7140
gggtgcataa acgtatattc ttacaataat agatacatgt gaacttatat acagaaaaga    7200
aaatgagaaa aatgtgtgtg tgtatactca cacacgtggt cagtaaaaac ttttgagggg    7260
tttaatacag aaaatccaat cctgaggccc cagcactcag tacgcatata aagggctggg    7320
ctctgaagga cttctgactt tcacagatta tataaatctc aggaaagcaa ctagattcat    7380
gctggctcca aaagctgtgc tttatataag cacactggct atacaatagt tgtacagttc    7440
agctctttat aatagaaaca gacagaacaa gtataaatct tctattggtc tatgtcatga    7500
acaagaattc attcagtggc tctgttttat agtaaacatt gctattttat catgtctgca    7560
tttctcttct gtctgaatgt caccactaaa atttaactcc acagaaagtt tatactacag    7620
tacacatgca tatctttgag caaagcaaac catacctgaa agtgcaatag agcagaatat    7680
gaattacatg cgtgtctttc tcctagacta catgacccca tataaattac attacttatc    7740
tattctgcca tcaccaaaac aaaggtaaaa atacttttga agatctactc atagcaagta    7800
gtgtgcaaca aacagatatt tctctacatt tattttaggg gaataaaaat aagaaataaa    7860
atagtcagca agcctctgct ttctcatata tctgtccaaa cctaaagttt actgaaattt    7920
gctctttgaa tttccagttt tgcaagccta tcagattgtg ttttaatcag aggtactgaa    7980
aagtatcaat gaattctagc tttcactgaa caaaaatatg tagaggcaac tggcttctgg    8040
gacagtttgc tacccaaaag acaactgaat gcaaatacat aaatagattt atgaatatgg    8100
ttttgaacat gcacatgaga ggtggatata gcaacagaca cattaccaca gaattacttt    8160
aaaactactt gttaacattt aattgcctaa aaactgctcg taatttactg ttgtagccta    8220
ccatagagta ccctgcatgg tactatgtac agcattccat ccttacattt tcactgttct    8280
gctgtttgct ctagacaact cagagttcac catgggctcc atcggtgcag caagcatgga    8340
attttgtttt gatgtattca aggagctcaa agtccaccat gccaatgaga acatcttcta    8400
ctgccccatt gccatcatgt cagctctagc catggtatac ctgggtgcaa aagacagcac    8460
caggacacaa ataaataagg tgagcctaca gttaaagatt aaaaccttg ccctgctcaa    8520
```

```
tggagccaca gcacttaatt gtatgataat gtcccttgga aactgcatag ctcagaggct   8580
gaaaatctga aaccagagtt atctaaaagt gtggccacct ccaactccca gagtgttacc   8640
caaatgcact agctagaaat cttgaaactg gattgcataa cttcttttg tcataaccat    8700 tatttcagct actattattt tcaattacag gttgttcgct ttgataaact tccaggattc   8760
ggagacagta ttgaagctca ggtacagaaa taatttcacc tccttctcta tgtcccttc    8820 ctctggaagc aaaatacagc agatgaagca atctcttagc tgttccaagc cctctctgat   8880
gagcagctag tgctctgcat ccagcagttg ggagaacact gttcataaga acagagaaaa   8940
agaaggaagt aacaggggat tcagaacaaa cagaagataa aactcaggac aaaaatccg    9000 tgtgaatgag gaaacttgtg gatatttgta cgcttaagca agacagctag atgattctgg   9060
ataaatgggt ctggttggaa aagaaggaaa gcctggctga tctgctggag ctagattatt    9120
gcagcaggta ggcaggagtt ccctagagaa aagtatgagg gaattacaga agaaaaacag   9180
cacaaaattg taaatattgg aaaaggacca catcagtgta gttactagca gtaagacaga   9240
caggatgaaa aatagttttg taaacagaag tatctaacta ctttactctg ttcatacact    9300
acgtaaaact tactaagtaa taaaactaga ataacaacat ctttctttct ctttgtattc   9360
agtgtggcac atctgtaaac gttcactctt cacttagaga catcctcaac caaatcacca   9420
aaccaaatga tgtttattcg ttcagccttg ccagtagact ttatgctgaa gagagatacc   9480
caatcctgcc agtaagttgc tctaaaatct gatctgagtg tattccatgc caaagctcta   9540
ccattctgta atgcaaaaac agtcagagtt ccacatgttt cactaagaaa atttctttt    9600 ctcttgtttt tacaaatgaa agagaggaca aataacattt ctctatcacc gacctgaaac   9660
tctacagtct tcagagaatg aatggcttgc taaaagaatg tcaaatctta ctatacagct   9720
atttcatatt acactactaa atacactata aggcatagca tgtagtaata cagtgtaaaa    9780
tagcttttta cactactata ttattaatat ctgttaattc cagtcttgca tttcacattt   9840
gcaaaacgtt ttgaaattcg tatctgaaag ctgaatactc ttgctttaca ggaatacttg   9900
cagtgtgtga aggaactgta tagaggaggc ttggaaccta tcaactttca aacagctgca   9960
gatcaagcca gagagctcat caattcctgg gtagaaagtc agacaaatgg taaggtagaa  10020
catgctttgt acatagtgag agttggttca ccctaatact gagaacttgg atatagctca  10080
gccagcgtgc tttgcgttca agcttaccag agctgttgta tgcctgttaa gcagggcata  10140
cagtcatgag gctcttgaaa aatcttaaca gacaaagggc aatggaaaat cggagttaag  10200
ggatggtagg gataaaatgc atagaaaag gtaccacaat tttgattttt gcccataatgc  10260 ctctctgcgt ggttcctcaa ttttctact tcattcctca tctcctcaga gcattccttt   10320
ccctcatgct tgaaacacag atgaaagact gtgaattcta actgagatga aaacatccac  10380
aaccacacaa cctctggtgt ggagtcacat tctgtgaagg caaaaactag gccacgtaat  10440
ctatgcgtgc aagctacgcg taagctatgt gtgtgacagg acaatgtgag gaacatacta  10500
tgtgcacaag gactgcagaa taaacaggag caaagttttt gaagaaaaca gagtaaaatc  10560 ctgtttttcct cttttgttac attctttaca tatatctcaa atttcctctt tggttagaag  10620
caagtaatat ttatgtttct tggtactgtt tgggttgaag accattctgg gataagagaa  10680
attccagtgg ttcttcccct aatcataaaa tgtcaggttt agttttttg taacacagaa   10740 atctcttcat ctttattctt ttgttgtgat tcttgataga gagagaaaca agacttactg  10800
acaatagcag caagaaaatc aatcttggaa gaacaagatt gcaattgcaa aaacaaacca  10860
atgtccttgc ccctacatcc tcttccccat aaattctaca ttctctatct accttgtgct  10920
```

```
tgccaacatg atatacgtaa actctctttt cctattcatt cttaaaggaa ttatcagaaa    10980
tgtccttcag ccaagctccg tggattctca aactgcaatg gttctggtta atgccattgt    11040
cttcaaagga ctgtgggaga aagcatttaa ggatgaagac acacaagcaa tgcctttcag    11100
agtgactgag gtatatgggc ataccttaga gatgtaatct agaatttatg aagagagtag    11160
acatgttgtt atatgaacac tgcattagcg tatctgctca tttgtctgca tctctttcag    11220
acactgtgtt aaaagcaggg aattttcctt atgtctctct cgtcacaata ttcctgacat    11280
tgcaaagctc ctgagaaata acttcagatt ccacttttcc taggaaggct tctggatgag    11340
aactaatcat cttaactgta actagacatt tctgcatcca agaataatct ttgttaaaac    11400
tatattctct ctctcttttt tttttttttt tggttctcca gcaagaaagc aaacctgtgc    11460
agatgatgta ccagattggt ttatttagag tggcatcaat ggcttctgag aaaatgaaga    11520
tcctggagct tccatttgcc agtgggacaa tgagcatgtt ggtgctgttg cctgatgaag    11580
tctcaggcct tgagcaggta tggccctaga agttggcttc agaatattaa aaacacatgg    11640
aaatttagct gttgtaaagc tcttttcaac acagttatcc taaaacattt aaccagcaca    11700
aatttcatca tgattcaata tgtgattgtt gcatagaagt gtagatttgt cccactgggt    11760
cctgcaatag cccatgctga gcatggcttg ctgaaagaac tgctttagag ggtgaaaagt    11820
ttgacacagc agacaagatg attctcacct aagcagctgt tactgtagtg gcttgaactc    11880
taaaggtctt gtatctccat tcctgtgcac tgaggagctt cttggaaagt tcatataagg    11940
tttactagtt ctaactatta tctcatttgg tggcactcaa tgtgctttgt tcacgtcttc    12000
ataaattaat ctatctaaaa attggatgtg gttaaagcaa tttcagaaat aacatgtaca    12060
taatgtacaa ttattgatat gaacagaaca caggcatagc atattgtaat taggaggact    12120
gtagttattt tgaataggaa acacaatgta ataatgaga attcattgaa atgttagtat    12180
gctaactcaa tctaaattat aaagataaag aggcatttaa tcacagctag atttccatca    12240
cttgtgacag acaggcatat gaatgattat gtacagctct aggaaaaaaa gtatgtagga    12300
aaactagtac atttttgatta gaaagtctga aaatgaggtg ccttgatcaa agagaatacg    12360
tgtgtttgag aaaaaaaaag tttggataga ggtggtaaga gagaatatat tgaaatggtg    12420
tttctacaaa ctgccatggc cagatttgtg taagagacat tcagtaagta ggcaaggaaa    12480
gaaatattac taggtacaaa gcaacatcag taataccaaa agaaaccaat tattccagat    12540
gccaatctcg taatagggtt aagagatttc caccccctcta gtggtcacca gtgcaaccag    12600
taactttgct aatttacatt ttcttttttt aaatggcaga tatagctttg aactgagtga    12660
tcatgaactg gtactgtgta atagatgaag acatacttga cgactaaact tctgattttt    12720
aaaaactcaa attctcttga aagatcagtt cccagtctag taacagctga tagttttaagt    12780
atcagtaatt ggctaccatt aacaactggc tcctgagagg tcttaaatgt agagacagct    12840
ttaaactcaa aagcacagag tgattttttag aatagatttc ccaagcaaag aaaataaaca    12900
gggaggagct ttaagggagt agccatctca ttattattat tatttaaaga aatggcagca    12960
agcctacaaa agaaaaataa gacagagcag agaagaaaga gtcatggtat gcttttctat    13020
cttagcaaaa ttaatctcta catgcctagg aaaaagccat gacaagagca atcagttcaa    13080
aaggtgtatg caaaaaacca cataatagta actagtactg cattgccagg aaggaagtta    13140
tgtcgccatt ccatggatct cattctcatt tccttgcagc ttgagagtat aatcaacttt    13200
gaaaaactga ctgaatggac cagttctaat gttatggaag agaggaagat caaagtgtac    13260
ttacctcgca tgaagatgga ggaaaaatac aacctcacat ctgtcttaat ggctatgggc    13320
```

```
attactgacg tgtttagctc ttcagccaat ctgtctggca tctcctcagc agagagcctg    13380
aagatatctc aagctgtcca tgcagcacat gcagaaatca atgaagcagg cagagaggtg    13440
gtagggtcag cagaggctgg agtggatgct gcaagcgtct ctgaagaatt tagggctgac    13500
catccattcc tcttctgtat caagcacatc gcaaccaacg ccgttctctt ctttggcaga    13560
tgtgtttccc cttaaaaaga agaaagctga aaaactctgt cccttccaac aagacccaga    13620
gcactgtagt atcaggggta aaatgaaaag tatgttatct gctgcatcca gacttcataa    13680
aagctggagc ttaatctaga aaaaaaatca gaaagaaatt acactgtgag aacaggtgca    13740
attcactttt cctttacaca gagtaatact ggtaactcat ggatgaaggc ttaagggaat    13800
gaaattggac tcacagtact gagtcatcac actgaaaaat gcaacctgat acatcagcag    13860
aaggtttatg ggggaaaaat gcagccttcc aattaagcca gatatctgta tgaccaagct    13920
gctccagaat tagtcactca aaatctctca gattaaatta tcaactgtca ccaaccattc    13980
ctatgctgac aaggcaattg cttgttctct gtgttcctga tactacaagg ctcttcctga    14040
cttcctaaag atgcattata aaaatcttat aattcacatt tctccctaaa cttgactca    14100 atcatggtat gttggcaaat atggtatatt actattcaaa ttgtttcctt gtacccata    14160 tgtaatgggt cttgtgaatg tgctcttttg ttcctttaat cataataaa acatgtttaa    14220 gcaaacactt ttcacttgta gtatttgaag tacagcaagg ttgtgtagca gggaaagaat    14280
gacatgcaga ggaataagta tggacacaca ggctagcagc gactgtagaa caagtactag    14340
tgggtgagaa gttgaacaag agtcccctac aagcaactta atctaataag ctagtggtct    14400
acatcagcta aaagagcata gtgagggatg aaattggttc tcctttctaa gcatcacctg    14460
ggacaactca tctggagcag tgtgtccaat ctgccgctgc cctgatctcg gctggggtga    14520
tgggacagac cttggctgcc actgagacat ctgagacact gagatctgtc tcaactcaga    14580
tttacccaag aacagctcat tgccaacaga acaaaatctc aaacttatgg ctagtgatga    14640
cagcagtcag ttgtcccatc tgtgacccac caaggctggc atgctggaat gagcaggctt    14700
tggtggcatg tagttactgg acagcaccac tgacatgggc aggggaaaaa ctgagcatgg    14760
tgtaaatcac tgcctcaaag ccacttctct gtgcctgcac catgcttgaa agctcttcta    14820
caggagctgg gtttgttcaa gaaagcttct gtttctccca tctgcttctt gtaccttcac    14880
agggacagag ttagaagggt acagccatgg ctggaagggg ctgactttca aatgtgccta    14940
attttccttt ggttgctgct gcagctgcag aagaaggggt tcagaagcca agagctttga    15000
gataaggatg cctaacctat gttgaagaca tttgtgctga cacctcaggc cccaggatag    15060
gacaactgct ggattgtggc taacccacta gctacagaac ctaatttata ttaccagatt    15120
aggaagagca aaagaacatg tatttataac aggaggtctt ctgtgcttct ctactaaaag    15180
gtgctgtgaa ggagcccaca gtgcagcagt gtatgaggcc tgaaagaggc cgcagcacac    15240
gaagagccct ggtaggagca gcacacagag gggcaggagg gctgggggaa ctgccaccca    15300
tggggacctg tgtgaagcag tgcactcctg agggtggac tgcgtgggaa aggaaaagaa    15360
agcaaacaga cctgtgatga actgtcacac agactgcaga gtgacagagg agggcacgag    15420
gcagtgcgcc cactgcaggg agtggcgctc cttcctcaca gcagcgctaa cagcttggca    15480
ccaatattca gtagtctgtg gtgatacttt ttccagtttc accacacagc atttcgcttg    15540
ttctacttgt tttagctttc cccctccaca agataacaca tactttgcca gtcagtccct    15600
aagaccttaa cttaacagtt agcaaacagg atcttgcaaa agaaggaaga taacatgaca    15660
ccaccttcac tggtgtataa atagttcaaa tactttcctt cactttcccg taaattagtt    15720
```

```
gattgcaggt caggagataa caggggaact tactgcaaga gagaaaatga tgtttaatat    15780
tgtcttggac tttctggtgg tctgggcatg aaaatgggt  actcaaaatc ctcgggacgt    15840 ttattttca  cctgatttat tcccaaactg cactatttct aggccattgg agttcttatc    15900
aattaaatta ctttggct   ctctgctatc tcactccctt tcatcttcag catcactttc    15960
agcacaatta caggagaaga cttagactca gagctttagg actcatcata agaggctttc    16020
attgctctgt caccacaccc catatagatc t                                   16051

<210> SEQ ID NO 23
<211> LENGTH: 7334
<212> TYPE: DNA
<213> ORGANISM: Artificial Sequence
<220> FEATURE:
<223> OTHER INFORMATION: pBS-OM-4.4 Vector

<400> SEQUENCE: 23
atcaagctta tcgataccgt cgacctcgag ggggggcccg gtacccagct tttgttccct      60
ttagtgaggg ttaatttcga gcttggcgta atcatggtca tagctgtttc ctgtgtgaaa     120
ttgttatccg ctcacaattc cacacaacat acgagccgga agcataaagt gtaaagcctg     180
gggtgcctaa tgagtgagct aactcacatt aattgcgttg cgctcactgc ccgctttcca     240
gtcgggaaac ctgtcgtgcc agctgcatta atgaatcggc caacgcgcgg ggagaggcgg     300
tttgcgtatt gggcgctctt ccgcttcctc gctcactgac tcgctgcgct cggtcgttcg     360
gctgcggcga gcggtatcag ctcactcaaa ggcggtaata cggttatcca cagaatcagg     420
ggataacgca ggaaagaaca tgtgagcaaa aggccagcaa aaggccagga accgtaaaaa     480
ggccgcgttg ctggcgtttt tccataggct ccgcccccct gacgagcatc acaaaaatcg     540
acgctcaagt cagaggtggc gaaacccgac aggactataa agataccagg cgtttccccc     600
tggaagctcc ctcgtgcgct ctcctgttcc gaccctgccg cttaccggat acctgtccgc     660
ctttctccct tcgggaagcg tggcgctttc tcatagctca cgctgtaggt atctcagttc     720
ggtgtaggtc gttcgctcca agctgggctg tgtgcacgaa ccccccgttc agcccgaccg     780
ctgcgcctta tccggtaact atcgtcttga gtccaacccg gtaagacacg acttatcgcc     840
actggcagca gccactggta acaggattag cagagcgagg tatgtaggcg gtgctacaga     900
gttcttgaag tggtggccta actacggcta cactagaagg acagtatttg gtatctgcgc     960
tctgctgaag ccagttacct tcggaaaaag agttggtagc tcttgatccg gcaaacaaac    1020
caccgctggt agcggtggtt tttttgtttg caagcagcag attacgcgca gaaaaaaagg    1080
atctcaagaa gatcctttga tcttttctac ggggtctgac gctcagtgga acgaaaactc    1140
acgttaaggg attttggtca tgagattatc aaaaaggatc ttcacctaga tccttttaaa    1200
ttaaaaatga agttttaaat caatctaaag tatatatgag taaacttggt ctgacagtta    1260
ccaatgctta atcagtgagg cacctatctc agcgatctgt ctatttcgtt catccatagt    1320
tgcctgactc cccgtcgtgt agataactac gatacgggag ggcttaccat ctggccccag    1380
tgctgcaatg ataccgcgag acccacgctc accggctcca gatttatcag caataaacca    1440
gccagccgga agggccgagc gcagaagtgg tcctgcaact ttatccgcct ccatccagtc    1500
tattaattgt tgccgggaag ctagagtaag tagttcgcca gttaatagtt tgcgcaacgt    1560
tgttgccatt gctacaggca tcgtggtgtc acgctcgtcg tttggtatgg cttcattcag    1620
ctccggttcc caacgatcaa ggcgagttac atgatccccc atgttgtgca aaaaagcggt    1680
tagctccttc ggtcctccga tcgttgtcag aagtaagttg gccgcagtgt tatcactcat    1740
```

```
ggttatggca gcactgcata attctcttac tgtcatgcca tccgtaagat gcttttctgt   1800
gactggtgag tactcaacca agtcattctg agaatagtgt atgcggcgac cgagttgctc   1860
ttgcccggcg tcaatacggg ataataccgc gccacatagc agaactttaa aagtgctcat   1920
cattggaaaa cgttcttcgg ggcgaaaact ctcaaggatc ttaccgctgt tgagatccag   1980
ttcgatgtaa cccactcgtg cacccaactg atcttcagca tcttttactt tcaccagcgt   2040
ttctgggtga gcaaaaacag gaaggcaaaa tgccgcaaaa aagggaataa gggcgacacg   2100
gaaatgttga atactcatac tcttcctttt tcaatattat tgaagcattt atcagggtta   2160
ttgtctcatg agcggataca tatttgaatg tatttagaaa aataaacaaa tagggggttcc  2220 gcgcacattt ccccgaaaag tgccacctaa attgtaagcg ttaatatttt gttaaaattc   2280
gcgttaaatt tttgttaaat cagctcattt tttaaccaat aggccgaaat cggcaaaatc   2340
ccttataaat caaaagaata gaccgagata gggttgagtg ttgttccagt ttggaacaag   2400
agtccactat taaagaacgt ggactccaac gtcaaagggc gaaaaaccgt ctatcagggc   2460
gatggcccac tacgtgaacc atcaccctaa tcaagttttt tggggtcgag gtgccgtaaa   2520
gcactaaatc ggaaccctaa agggagcccc cgatttagag cttgacgggg aaagccggcg   2580
aacgtggcga gaaaggaagg gaagaaagcg aaaggagcgg gcgctagggc gctggcaagt   2640
gtagcggtca cgctgcgcgt aaccaccaca cccgccgcgc ttaatgcgcc gctacagggc   2700
gcgtcccatt cgccattcag gctgcgcaac tgttgggaag ggcgatcggt gcgggcctct   2760
tcgctattac gccagctggc gaaaggggga tgtgctgcaa ggcgattaag ttgggtaacg   2820
ccagggtttt cccagtcacg acgttgtaaa acgacggcca gtgaattgta atacgactca   2880
ctatagggcg aattggagct ccaccgcggt ggcggccgct ctagaactag tggatccttc   2940
ttaaaaagca gaccatcatt cactgcaaac ccagagcttc atgcctctcc ttccacaacc   3000
gaaaacagcc ggcttcattt gtctttttta aatgctgttt tccaggtgaa ttttggccag   3060
cgtgttggct gagatccagg agcacgtgtc agctttctgc tctcattgct cctgttctgc   3120
attgcctctt tctgggtttt ccaagagggg gggagacttt gcgcggggat gagataatgc   3180 ccccttttctt agggtggctg ctgggcagca gagtggctct gggtcactgt ggcaccaatg   3240
ggaggcacca gtgggggtgt gttttgtgca gggggggaagc attcacagaa tggggctgat   3300
cctgaagctt gcagtccaag gctttgtctg tgtacccagt gaaatccttc ctctgttaca   3360
taaagcccag ataggactca gaaatgtagt cattccagcc cccctcttcc tcagatctgg   3420
agcagcactt gtttgcagcc agtcctcccc aaaatgcaca gacctcgccg agtggaggga   3480
gatgtaaaca gcgaaggtta attacctcct tgtcaaaaac actttgtggt ccatagatgt   3540
ttctgtcaat cttacaaaac agaaccgaga ggcagcgagc actgaagagc gtgttcccat   3600
gctgagttaa tgagacttgg cagctcgctg tgcagagatg atccctgtgc ttcatgggag   3660
gctgtaacct gtctccccat cgccttcaca ccgcagtgct gtcctggaca cctcaccctc   3720
cataagctgt aggatgcagc tgcccaggga tcaagagact tttcctaagg ctcttaggac   3780
tcatctttgc cgctcagtag cgtgcagcaa ttactcatcc caactatact gaatgggttt   3840
ctgccagctc tgcttgtttg tcaataagca tttcttcatt ttgcctctaa gtttctctca   3900
gcagcaccgc tctgggtgac ctgagtggcc acctggaacc cgaggggcac agccaccacc   3960
tccctgttgc tgctgctcca gggactcatg tgctgctgga tgggggaag catgaagttc   4020 ctcacccaga cacctgggtt gcaatggctg cagcgtgctc ttcttggtat gcagattgtt   4080
tccagccatt acttgtagaa atgtgctgtg gaagcccttt gtatctcttt ctgtggccct   4140
```

```
tcagcaaaag ctgtgggaaa gctctgaggc tgctttcttg ggtcgtggag gaattgtatg    4200
ttccttcttt aacaaaaatt atccttagga gagagcactg tgcaagcatt gtgcacataa    4260
aacaattcag gttgaaaggg ctctctggag gttttccagcc tgactactgc tcgaagcaag   4320
gccaggttca aagatggctc aggatgctgt gtgccttcct gattatctgt gccaccaatg    4380
gaggagattc acagccactc tgcttcccgt gccactcatg gagaggaata ttcccttata    4440
ttcagataga atgttatcct ttagctcagc cttccctata accccatgag ggagctgcag    4500
atccccatac tctccccttc tctggggtga aggccgtgtc ccccagcccc ccttcccacc    4560
ctgtgcccta agcagcccgc tggcctctgc tggatgtgtg cctatatgtc aatgcctgtc    4620
cttgcagtcc agcctgggac atttaattca tcaccagggt aatgtggaac tgtgtcatct    4680 tccccctgcag ggtacaaagt tctgcacggg gtccttccgg ttcaggaaaa ccttcactgg    4740
tgctacctga atcaagctct atttaataag ttcataagca catggatgtg ttttcctaga    4800
gatacgtttt aatggtatca gtgattttta tttgctttgt tgcttacttc aaacagtgcc    4860
tttgggcagg aggtgaggga cgggtctgcc gttggctctg cagtgatttc tccaggcgtg    4920
tggctcaggt cagatagtgg tcactctgtg gccagaagaa ggacaaagat ggaaattgca    4980
gattgagtca cgttaagcag gcatcttgga gtgatttgag gcagtttcat gaaagagcta    5040
cgaccactta ttgttgtttt ccccttttac aacagaagtt ttcatcaaaa taacgtggca    5100
aagcccagga atgtttggga aaagtgtagt taaatgtttt gtaattcatt tgtcggagtg    5160
ctaccagcta agaaaaaagt cctacctttg gtatggtagt cctgcagaga atacaacatc    5220
aatattagtt tggaaaaaaa caccaccacc accagaaact gtaatggaaa atgtaaacca    5280
agaaattcct tgggtaagag agaaaggatg tcgtatactg gccaagtcct gcccagctgt    5340
cagcctgctg accctctgca gttcaggacc atgaaacgtg gcactgtaag acgtgtcccc    5400
tgcctttgct tgcccacaga tctctgccct tgtgctgact cctgcacaca agagcatttc    5460
cctgtagcca aacagcgatt agccataagc tgcacctgac tttgaggatt aagagtttgc    5520
aattaagtgg attgcagcag gagatcagtg gcagggttgc agatgaaatc cttttctagg    5580
ggtagctaag ggctgagcaa cctgtcctac agcacaagcc aaaccagcca agggttttcc    5640
tgtgctgttc acagaggcag ggccagctgg agctggagga ggttgtgctg ggaccctct    5700 ccctgtgctg agaatggagt gatttctggg tgctgttcct gtggcttgca ctgagcagct    5760
caagggagat cggtgctcct catgcagtgc caaaactcgt gtttgatgca gaaagatgga    5820
tgtgcacctc cctcctgcta atgcagccgt gagcttatga aggcaatgag ccctcagtgc    5880
agcaggagct gtagtgcact cctgtaggtg ctagggaaaa tctctggttc ccagggatgc    5940
attcataagg gcaatatatc ttgaggctgc gccaaatctt tctgaaatat tcatgcgtgt    6000
tcccttaatt tatagaaaca aacacagcag aataattatt ccaatgcctc ccctcgaagg    6060
aaacccatat ttccatgtag aaatgtaacc tatatacaca cagccatgct gcatccttca    6120
gaacgtgcca gtgctcatct cccatggcaa aatactacag gtattctcac tatgttggac    6180
ctgtgaaagg aaccatggta agaaacttcg gttaaggta tggctgcaaa actactcata    6240
ccaaaacagc agagctccag acctcctctt aggaaagagc cacttggaga gggatggtgt    6300
gaaggctgga ggtgagagac agagcctgtc ccagttttcc tgtctctatt ttctgaaacg    6360
tttgcaggag gaaaggacaa ctgtactttc aggcatagct ggtgccctca cgtaaataag    6420
ttccccgaac ttctgtgtca tttgttctta agatgctttg gcagaacact ttgagtcaat    6480
tcgcttaact gtgactaggt ctgtaaataa gtgctccctg ctgataaggt tcaagtgaca    6540
```

```
tttttagtgg tatttgacag catttacctt gctttcaagt cttctaccaa gctcttctat    6600
acttaagcag tgaaaccgcc aagaaaccct tccttttatc aagctagtgc taaataccat    6660
taacttcata ggttagatac ggtgctgcca gcttcacctg gcagtggttg gtcagttctg    6720
ctggtgacaa agcctccctg gcctgtgctt ttacctagag gtgaatatcc aagaatgcag    6780
aactgcatgg aaagcagagc tgcaggcacg atggtgctga gccttagctg cttcctgctg    6840
ggagatgtgg atgcagagac gaatgaagga cctgtccctt actcccctca gcattctgtg    6900
ctatttaggg ttctaccaga gtccttaaga ggtttttttt tttttggtc caaaagtctg    6960 tttgtttggt tttgaccact gagagcatgt gacacttgtc tcaagctatt aaccaagtgt    7020
ccagccaaaa tcaattgcct gggagacgca gaccattacc tggaggtcag gacctcaata    7080
aatattacca gcctcattgt gccgctgaca gattcagctg gctgctccgt gttccagtcc    7140
aacagttcgg acgccacgtt tgtatatatt tgcaggcagc ctcgggggga ccatctcagg    7200
agcagagcac cggcagccgc ctgcagagcc gggcagtacc tcaccatggc catggcaggt    7260
gtcttcgtgc tgttctcttt cgtgctttgt ggcttcctcc caggtgagta actcccagag    7320
tgctgcagaa gctt                                                     7334

<210> SEQ ID NO 24
<211> LENGTH: 4327
<212> TYPE: DNA
<213> ORGANISM: Artificial Sequence
<220> FEATURE:
<223> OTHER INFORMATION: pAVIJCR-A137.91.1.2 Vector

<400> SEQUENCE: 24
gccaatgtgg tacttcccac attgtataag aaatttggca agtttagagc aatgtttgaa      60
gtgttgggaa atttctgtat actcaagagg gcgttttga caactgtaga acagaggaat     120
caaaaggggg tgggaggaag ttaaaagaag aggcaggtgc aagagagctt gcagtcccgc     180
tgtgtgtacg acactggcac catggctttg acctttgcct tactggtggc tctcctggtg     240
ctgagctgca agagcagctg ctctgtgggc tgcgatctgc ctcagaccca cagcctgggc     300
agcaggagga ccctgatgct gctggctcag atgaggagaa tcagcctgtt tagctgcctg     360
aaggataggc acgattttgg cttctcctca gaggagtttg gcaaccagtt tcagaaggct     420
gagaccatcc ctgtgctgca cgagatgatc cagcagatct ttaacctgtt tagcaccaag     480
gatagcagcg ctgcttggga tgagaccctg ctggataagt tttacaccga gctgtaccag     540
cagctgaacg atctggaggc ttgcgtgatc cagggcgtgg gcgtgaccga gacccctctg     600
atgaaggagg atagcatcct ggctgtgagg aagtactttc agaggatcac cctgtacctg     660
aaggagaaga gtacagcccc ctgcgcttgg aagtcgtga gggctgagat catgaggagc     720
tttagcctga gcaccaacct gcaagagagc ttgaggtcta aggagtaaaa agtctagagt     780
cggggcggcc ggccgcttcg agcagacatg ataagataca ttgatgagtt tggacaaacc     840
acaactagaa tgcagtgaaa aaaatgcttt atttgtgaaa tttgtgatgc tattgcttta     900
tttgtaacca ttataagctg caataaacaa gttaacaaca acaattgcat tcatttatg     960 tttcaggttc agggggaggt gtgggaggtt ttttaaagca agtaaaacct ctacaaatgt    1020
ggtaaaatcg ataaggatcc gtcgaccgat gcccttgaga gccttcaacc cagtcagctc    1080
cttccggtgg gcgcggggca tgactatcgt cgccgcactt atgactgtct tctttatcat    1140
gcaactcgta ggacaggtgc cggcagcgct cttccgcttc ctcgctcact gactcgctgc    1200
gctcggtcgt tcggctgcgg cgagcggtat cagctcactc aaaggcggta atacggttat    1260
```

```
ccacagaatc agggggataac gcaggaaaga acatgtgagc aaaaggccag caaaaggcca   1320
ggaaccgtaa aaaggccgcg ttgctggcgt ttttccatag gctccgcccc cctgacgagc   1380
atcacaaaaa tcgacgctca agtcagaggt ggcgaaaccc gacaggacta taaagatacc   1440
aggcgtttcc ccctggaagc tccctcgtgc gctctcctgt tccgaccctg ccgcttaccg   1500
gatacctgtc cgcctttctc ccttcgggaa gcgtggcgct ttctcaatgc tcacgctgta   1560
ggtatctcag ttcggtgtag gtcgttcgct ccaagctggg ctgtgtgcac gaaccccccg   1620
ttcagcccga ccgctgcgcc ttatccggta actatcgtct tgagtccaac ccggtaagac   1680
acgacttatc gccactggca gcagccactg gtaacaggat tagcagagcg aggtatgtag   1740
gcggtgctac agagttcttg aagtggtggc ctaactacgg ctacactaga aggacagtat   1800
ttggtatctg cgctctgctg aagccagtta ccttcggaaa aagagttggt agctcttgat   1860
ccggcaaaca aaccaccgct ggtagcggtg gtttttttgt ttgcaagcag cagattacgc   1920
gcagaaaaaa aggatctcaa gaagatcctt tgatcttttc tacggggtct gacgctcagt   1980
ggaacgaaaa ctcacgttaa gggattttgg tcatgagatt atcaaaaagg atcttcacct   2040
agatcctttt aaattaaaaa tgaagtttta aatcaatcta agtatatat gagtaaactt   2100 ggtctgacag ttaccaatgc ttaatcagtg aggcacctat ctcagcgatc tgtctatttc   2160
gttcatccat agttgcctga ctccccgtcg tgtagataac tacgatacgg gagggcttac   2220
catctggccc cagtgctgca atgataccgc gagacccacg ctcaccggct ccagatttat   2280
cagcaataaa ccagccagcc ggaagggccg agcgcagaag tggtcctgca actttatccg   2340
cctccatcca gtctattaat tgttgccggg aagctagagt aagtagttcg ccagttaata   2400
gtttgcgcaa cgttgttgcc attgctacag gcatcgtggt gtcacgctcg tcgtttggta   2460
tggcttcatt cagctccggt tcccaacgat caaggcgagt tacatgatcc cccatgttgt   2520
gcaaaaaagc ggttagctcc ttcggtcctc cgatcgttgt cagaagtaag ttggccgcag   2580
tgttatcact catggttatg gcagcactgc ataattctct tactgtcatg ccatccgtaa   2640
gatgcttttc tgtgactggt gagtactcaa ccaagtcatt ctgagaatag tgtatgcggc   2700
gaccgagttg ctcttgcccg gcgtcaatac gggataatac cgcgccacat agcagaactt   2760
taaaagtgct catcattgga aaacgttctt cggggcgaaa actctcaagg atcttaccgc   2820
tgttgagatc cagttcgatg taacccactc gtgcacccaa ctgatcttca gcatctttta   2880
ctttcaccag cgtttctggg tgagcaaaaa caggaaggca aaatgccgca aaaagggaa   2940 taagggcgac acggaaatgt tgaatactca tactcttcct ttttcaatat tattgaagca   3000
tttatcaggg ttattgtctc atgagcggat acatatttga atgtatttag aaaaataaac   3060
aaataggggt tccgcgcaca tttccccgaa aagtgccacc tgacgcgccc tgtagcggcg   3120
cattaagcgc ggcgggtgtg gtggttacgc gcagcgtgac cgctacactt gccagcgccc   3180
tagcgcccgc tcctttcgct ttcttccctt cctttctcgc cacgttcgcc ggctttcccc   3240
gtcaagctct aaatcggggg ctccctttag ggttccgatt tagtgcttta cggcacctcg   3300
accccaaaaa acttgattag ggtgatggtt cacgtagtgg gccatcgccc tgatagacgg   3360 ttttttcgccc tttgacgttg gagtccacgt tctttaatag tggactcttg ttccaaactg   3420
gaacaacact caaccctatc tcggtctatt cttttgattt ataagggatt ttgccgattt   3480
cggcctattg gttaaaaaat gagctgattt aacaaaaatt taacgcgaat tttaacaaaa   3540
tattaacgtt tacaatttcc cattcgccat tcaggctgcg caactgttgg gaagggcgat   3600
cggtgcgggc ctcttcgcta ttacgccagc ccaagctacc atgataagta agtaatatta   3660
```

-continued

```
aggtacggga ggtacttgga gcggccgcaa taaaatatct ttattttcat tacatctgtg    3720
tgttggtttt ttgtgtgaat cgatagtact aacatacgct ctccatcaaa acaaaacgaa    3780
acaaaacaaa ctagcaaaat aggctgtccc cagtgcaagt gcaggtgcca gaacatttct    3840
ctatcgatag gtaccgagct cttacgcgtg ctagccccga tgtacgggcc agatatacgc    3900
gttgacattg attattgact agttattaat agtaatcaat tacggggtca ttagttcata    3960
gcccatatat ggagttccgc gttacataac ttacggtaaa tggcccgcct ggctgaccgc    4020
ccaacgaccc ccgcccattg acgtcaataa tgacgtatgt tcccatagta acgccaatag    4080
ggactttcca ttgacgtcaa tgggtggact atttacggta aactgcccac ttggcagtac    4140
atcaagtgta tcatatgcca gtacgcccc ctattgacgt caatgacggt aaatggcccg    4200
cctggcatta tgcccagtac atgaccttat gggactttcc tacttggcag tacatctacg    4260
tattagtcat cgctattacc atgcatggct ttgacctttg ccttactggt ggctctcctg    4320
gtgctta                                                              4327
```

<210> SEQ ID NO 25
<211> LENGTH: 244
<212> TYPE: DNA
<213> ORGANISM: Artificial Sequence
<220> FEATURE:
<223> OTHER INFORMATION: The RRE (rev responsive element) sequence

<400> SEQUENCE: 25

```
aattgaggag ctttgttcct tgggttcttg ggagcagcag gaagcactat gggcgcagcg     60
tcaatgacgc tgacggtaca ggccagacaa ttattgtctg gtatagtgca gcagcagaac    120
aatttgctga gggctattga ggcgcaacag catctgttgc aactcacagt ctggggcatc    180
aagcagctcc aggcaagaat cctggctgtg gaaagatacc taaaggatca acagctcctg    240
gtac                                                                 244
```

<210> SEQ ID NO 26
<211> LENGTH: 158
<212> TYPE: DNA
<213> ORGANISM: Artificial Sequence
<220> FEATURE:
<223> OTHER INFORMATION: The ALV CTE (constitutive transport element)
      sequence

<400> SEQUENCE: 26

```
aatgtgggga gggcaaggct tgcgaatcgg gttgtaacgg gcaaggcttg actgagggga     60
caatagcatg tttaggcgaa aagcggggct tcggttgtac gcggttagga gtcccctcag    120
gatatagtag tttcgctttt gcatagggag ggggaaat                            158
```

<210> SEQ ID NO 27
<211> LENGTH: 55
<212> TYPE: DNA
<213> ORGANISM: Artificial Sequence
<220> FEATURE:
<223> OTHER INFORMATION: p10.0-OM-IFN-1 Primer

<400> SEQUENCE: 27

```
ggcgtcgacg gatccgttaa ccctagaact agtggatctc tgcccttgtg ctgac          55
```

<210> SEQ ID NO 28
<211> LENGTH: 31
<212> TYPE: DNA
<213> ORGANISM: Artificial Sequence
<220> FEATURE:
<223> OTHER INFORMATION: p10.0-OM-IFN-2

```
<400> SEQUENCE: 28
ggcctcgagc ctagactttt tactccttag a                                    31

<210> SEQ ID NO 29
<211> LENGTH: 346
<212> TYPE: DNA
<213> ORGANISM: Artificial Sequence
<220> FEATURE:
<223> OTHER INFORMATION: ALV vector 5' LTR sequence

<400> SEQUENCE: 29
aatgtagtct tatgcaatac tcttgtagtc ttgcaacatg cttatgtaac gatgagttag     60
caacatgcct tataaggaga gaaaaagcac cgtgcatgcc gattggtggg agtaaggtgg    120
tatgatcgtg gtatgatcgt gccttgttag gaaggcaaca gacgggtcta acacggattg    180
gacgaaccac tgaattccgc attgcagaga tattgtattt aagtgcctag ctcgatacaa    240
taaacgccat ttgaccattc accacattgg tgtgcacctg ggttgatggc cggaccgttg    300
attccctgrc gactacgagc acatgcatga agcagaaggc ttcatt                  346
```